US009315837B2

(12) United States Patent
Umidjon et al.

(10) Patent No.: US 9,315,837 B2
(45) Date of Patent: Apr. 19, 2016

(54) DESATURASES OF A GREEN MICROALGA AND USES THEREOF

(71) Applicant: Ben Gurion University of the Negev Research and Development Authority, Beer Sheva (IL)

(72) Inventors: Iskandarov Umidjon, Sde-Boker (IL); Inna Khozin Goldberg, Sde-Boker (IL); Zvi Hacohen, Omer (IL)

(73) Assignee: Ben Gurion University of the Negev Research and Development Authority, Beer Sheva (IL)

( * ) Notice: Subject to any disclaimer, the term of this patent is extended or adjusted under 35 U.S.C. 154(b) by 0 days.

(21) Appl. No.: 14/804,638

(22) Filed: Jul. 21, 2015

(65) Prior Publication Data

US 2016/0060662 A1    Mar. 3, 2016

Related U.S. Application Data

(63) Continuation of application No. 13/520,607, filed as application No. PCT/IL2011/000006 on Jan. 5, 2011, now abandoned.

(60) Provisional application No. 61/292,185, filed on Jan. 5, 2010.

(51) Int. Cl.
  *C12N 1/20* (2006.01)
  *C12P 7/64* (2006.01)
  *C12N 9/02* (2006.01)
  *C12N 15/82* (2006.01)

(52) U.S. Cl.
  CPC ............. *C12P 7/6427* (2013.01); *C12N 9/0071* (2013.01); *C12N 15/8247* (2013.01); *C12Y 114/19* (2013.01)

(58) Field of Classification Search
  CPC ......................................................... C12N 1/20
  USPC ...................................................... 435/252.3
  See application file for complete search history.

(56) References Cited

PUBLICATIONS

Accession No. D3K944; Submitted Name Delta 12 desaturase (2010).
Accession No. D3K945; Submitted Name Delta 6 desaturase (2010).
Accession No. D3K946; Submitted Name Delta 5 desaturase (Delta-5 fatty acid desaturase) (2010).
Kajikawa M et al: "Isolation and characterization of Δ6-desaturase, and ELO-like enzyme and Δ5-desaturase from the liverwort Marchantia polymorpha and production of arachidonic and eicosapentaenoic acids in the methylotrophic yeast Pichia pastoris", Plant Molecular Biology, Springer, Dordrecht, NL, vol. 54, No. 3, Feb. 1, 2004, pp. 335-352.
Domergue F et al.: "Cloning and functional 1-14 characterization of Phaeodactylum tricornutum from-end desaturases involved in eicosapentaenoic acid biosynthesis", European Journal of Biochemistry, Published by Springer-Verlag on Behalf of the Federation of European Biochemical Societies, vol. 269, No. 16, Aug. 1, 2002, pp. 4015-4113.
Sakuradani E et al.: "Identification of delta 12-fatty acid desaturase from arachidonic acid-producing mortierella fungus by heterologous expression in the yeast saccharomyces cerevisiae and the fungus aspergillus oryzae". European Journal of Biochemistry, Published by Springer-Verlag on Behalf of the Federation of European Biochemical Societies, vol. 261, No. 3, Jan. 1, 1999, pp. 812-820.
Los D A et al.: "Structure and expression of fatty acid desaturases", Biochimica Et Biophysica Acta, Elsevier NL, vol. 1394, No. 1, Jan. 1, 1998, pp. 3-15.
Database Geneseq [Online] Nov. 12, 2009, "Chlorella vulgaris protein, SEQ ID 4893.", accession No. GSP:AWW70226, Database accession No. AWW70226.
Database Geneseq [Online] Mar. 20, 2008, "Tetraselmis suecica delta 6 desaturase (TsD6D)-2 enzyme.",accession No. GSP:AQY10389, Database accession No. AQY10389.
Database UniProt [Online] May 26, 2009, "Micromonas pusilla (strain CCMP1545) (Picoplanktonic green alga).",accession No. UNIPROT:C1MH08 Database accession No. C1MH08.
Bigogno C et al.: "Lipid and fatty acid compsotion of the green oleaginous alga Parietochloris incisa, the richest plant source of arachidonic acid", Phytochemistry, Pergamon Press, GB, vol. 60, No. 5, Jul. 1, 2002, pp. 497-503.
Iskandarov et al.. Identification and Characterization of Δ12, Δ6, and Δ5 Desaturases from the Green Microalga Parietochloris incisa, Lipids (2010) 45:519-530.
Iskandarov et al. "Identification and Characterization of Δ12, Δ 6, and Δ5 Desaturases from the Green Microalga Parietochloris incisa", Lipids (2010) 45: 519-530.
Koushirou Suga et al., "Two Low-temperature-inducible Chlorella Genes for [Delta] 12 and [omega] −3 Fatty Acid Desaturase (FAD): Isolation of [Delta] 12 and [omega] −3 fad cDNA Clones, . . . ", Bioscience Biotechnology Biochemistry, vol. 66, No. 6, Jan. 22, 2002, pp. 1314-1327, XP055245563, Tokyo, Japan, ISSN: 0916-8451, DOI: 10.1271/bbb.66.1314.
Communication and Examination Report from a counterpart foreign application—European Application No. 11731732.1—, mailed Feb. 12, 2016; five (5) pages.

*Primary Examiner* — Tekchand Saidha
(74) *Attorney, Agent, or Firm* — Roach Brown McCarthy & Gruber, P.C.; Kevin D. McCarthy

(57) ABSTRACT

Isolated proteins which are at least partially encoded by polynucleotide sequences encoding novel desaturases are provided together with a composition which includes these isolated proteins. A transgenic plant, a transgenic alga, or a transgenic seed transformed by the polynucleotides encoding proteins which are at least partially encoded by novel desaturases are also provided. The invention also includes a process for making a very long-chain polyunsaturated fatty acid in a transformed cell, a transgenic alga, or a transgenic plant expressing the isolated protein or proteins which are at least partially encoded by the polynucleotide sequences encoding novel Δ5, Δ6, or Δ12 desaturases.

13 Claims, 16 Drawing Sheets

Figure 1A

```
P.incisa        ----MGKGGCYQAGPPSAKKWE---SRVPTAKPEFTIGTLRKAIPVHCFERSIPRSFAYL   53  SEQ. ID NO. 1
C.vulgaris      ----------MAATRRAPSAEGWT---RQPVNTKPAFSVSTLRKAIPAHCWQRSLPRSCAYL 49  SEQ. ID NO. 41
C.reinhardtii   MTVTRRKGVNIQADATDSAGEK---QRYPAAPTFESLGDIRKAIPAHCFEKSALRSFAHL   57  SEQ. ID NO. 42
G.hirsutum      ------MGAGGRMSVPPSQRKQESGSMKRVPISKPPFTLSEIKKAIPPHCFQRSLIRSFSYL 56  SEQ. ID NO. 43
O.europaea      ------MGAGGRLSVPATKAEEKKNPLKRVPYLKPPFTVGDIKKTIPPHCFKRSLLRSFSYV 56  SEQ. ID NO. 44
S.oleracea      ------MGAGGR-SIPPSARKEKSDALNRVPYEKPPFTLGQIKKAIPPHCFKRSVLRSFSYV 55  SEQ. ID NO. 45
                          *    ::  ..  ::*:  ** :::  *:   : :  :*

P.incisa        AADLAAIAVMYLSTFIDHPVVPRVLAWGLIWPAYWYFQGAVATGVWVIAHECGHQAFSP   113
C.vulgaris      AADLLALALVWASTFIDAAPVPAAVRWLALWPAYWYLAGAVATGIWVIAHECGHQAFSD   109
C.reinhardtii   AVDVTVCAWLWYGSTFIDHPAVPRYLAWFVLWPLYWFWQGAFMTGIWVIAHECGHGAFSN  117
G.hirsutum      VYDFILVSIFYYVATTYFH-NLPQPLSF-VAWPIYWTLQGSVLTGVWVIAHECGHHAFSD  114
O.europaea      VYDLFLVFLFYYIATSYFH-LLPSPFSY-LGWSVYWILQGCVCTGVWVIAHECGHHAFSD  114
S.oleracea      VYDFTIAFLLYYVATNYIH-LLPKPFNY-LAWPVYGFVQGCVLTGVWVIAHECGHHAFSD  113
                 .   .      ::: :.   .. ::  ..* :  :*  .* *:***::.**.

P.incisa        YQWLNDAVGLIVHSCLLVPYYSWKHSHRRHSNTGSTTKDEVFVPREAAMVESDFSLMQT   173
C.vulgaris      YQAVNDGVGLIVHSLLLLIVPYYSWKHSHRRHSNTGNVVKDEVFVPPTREEVSDKWELEQA 169
C.reinhardtii   SEALNDGVGLVMHSLLIVPYYSWKHSHRRHQNTGSTAKDEVFVPAVKPAGTKAPWYHRN   177
G.hirsutum      YQWIDDTVGLIIEHSSLLVPYFSWKYSHRRHSNTGSLERDEVFVPKKRSSIRWAKYLNN  174
O.europaea      YQWVDDTVGLIIHSTLLVPYFSWKYSHRRHSNTGSLERDEVFVPKPKSKLSWFTKYLNN  174
S.oleracea      YQWLDDTVGLVHSFLIVPYFSWKYSHRRHSNTGSMEKDEVFVPQRKENMSWFSKYLSN  173
                    :* **::*  ::.*:::**:  .   :******   .   .

P.incisa        APARFLVIFVSLTAGWPAYLFANASGRKYGK-WANHFDPYSPIFTKRERSEIVVSDVALT   232
C.vulgaris      WPIRLVKLFITETEGWPLYLAGWPLYLLENVASRPYEKSWVNHFDPWSPIFSKRELVEVAVSDAALV 229
C.reinhardtii   PVYRLGHILFQQLLGWPLYLLFQQLIGWPLYLIENVSGHEYPR-WANHFDPFSPIFTKRERIEVLVSDIALA 236
G.hirsutum      PPGRFVTVTIQLTEGWPLYLLAFNVAGRPYEG-LACHYNPYGPIYNDRERLQIYISDVGVL 233
O.europaea      PPGRVMTLVITLTLGWPLYLALNVSGRPYDR-FACHYDPHGPIYNDRERLQIYISDVCVI 233
S.oleracea      PPGRILTLVVTLTLGWPLYLLFNVSGRKYER-FACHYDPSSPIYSDRERLQIFISDVGIS 232
                       :  *  :***.* .    .   :     :.* . :.  : *:**. :
```

Figure 1B

```
P.incisa        VVIAGLYSLGKAFGWAMLVKEYVIPYPITKLLITKLMLPHHPITKLMLPHYADKEWDWL  292
C.vulgaris      AVLCGLRQLAASFGWAMLVKTWLVPYLVVNFWLVTITMLQHS---HPELPHYGEDEWDWL  286
C.reinhardtii   VVVAGLAAISRTWGFMFLLKTYLIPYLVVNHWLVMITFLQHT----HPKLPHYGDGEWDWL  293
G.hirsutum      AVTYGLYRLVLAKGLAWVICVYGVPLLIVNAFLVMITYLQHT----HPALPHYDSSEWDWL  290
O.europaea      ATSYILYRVALAQGLVWLTCVYGVPLLIVNGFLVLITYLQHT----HPPLPHYDSSEWDWL  290
S.oleracea      IVAFGLYHLAAAKGISWVLCVYGGPLLVVNGFLVLITFLQHT----HPSLPHYDTSEWDWL  289
                  *   *   :  * * : *   *      *     * * * .    *    * ******

P.incisa        RGALATCDRSYG-MPDHLHHHIADTHVAHHLFSTMPHYHAQEATEAIKPILGKYYKQDKR  351
C.vulgaris      RGALTTVDRDYGWLINSLHHHIADTHVAHHLFSQMPHYHAQEATEALKPVLGDYYRSDSR  346
C.reinhardtii   RGAMATVDRSYG-VLDHVFHHIADTHVAHHLFSYMPHYHAEEATEAIKKVLGDYYAYDSR  352
G.hirsutum      RGALATVDRDYG-ILNKVFHNITDTHVAHHLFSTMPHYHAMEATKAIKPILGEYYSFDGT  349
O.europaea      RGALATVDRDYG-VLNNVFHNITDTHVAHHLFSTMPHYHAMEATKAIKPLLGEYYQSDGT  349
S.oleracea      RGALATADRDYG-ILNKVFHNITDTHVAHHLISTMPHYHAMEATKAIKPILGKYYRLDST  348
                ***:   ::* *  :: : :*:*  **:* **** *.*::.**   .

P.incisa        NVWAALWEDFSLCRYVAPDT--AG-SGILWFRA--  381
C.vulgaris      PLLQAIWQDFGSCRYVAPDT--PG-DGVLWFRK--  376
C.reinhardtii   NVFERALWDEVGGCAVVAPDT--NGPEQVYWYHR--  383
G.hirsutum      PVVYKAIFREAKECIYVEPDEGEQSSKGVFWFRNKI  384
O.europaea      PFYKAMWREAKECLYVEPDE---PNKGVFWYKNKF  381
S.oleracea      PVFKAMWREAKECMYVEADE-DDQNKGVLWYRNKL  382
                  . *::*  :     * ..      . * *     
```

Figure 1C

```
P.incisa       MCQGQA------VQGLRRRSSFLKLTGDAINGAVAAIPDFNKLPAATPVFARRSLSDSALQ  55  SEQ. ID NO. 2
M.polymorpha   MASSTT------TAVKQSSGGLMSKWGTGSNLSFVSRKEQQQQQQSSPEASTPAAQQEKS   55  SEQ. ID NO. 46
P.tricornutum  MGKGGD------ARASKGSTAARKIS-----------------------------------  20  SEQ. ID NO. 47
T.pseudonana   MGKGGD------AAAATKRSGALKLAEKPQ-------------------------------  24  SEQ. ID NO. 48
M.squamata     MCPPKE------STRKNAGGPLTRGKLSADL------------------------------  25  SEQ. ID NO. 49
O.tauri        MCVETENNDGIPTVEIAFDGEREREAEANVKLS----------------------------  32  SEQ. ID NO. 50
               *:

P.incisa       QRDGPPRSKQQVTLEELAQHNTPEDCWLVIKNKVYDVSGWGPQHPSGHVIY---TYAGKDA  112
M.polymorpha   ISRESIPEGFLTVEEVSKHDNPSDCWIVINDKVYDVSGDVSAFGKTHPSGPVIF---TQAGRDA  112
P.tricornutum  ------------WQEVKTHASPEDAWIIHSNKVYDVSNW-HEHPSGAVIF---THAGDDM  64
T.pseudonana   ------------KYTWQEVKKHITPDDAWVHQNKVYDVSNW-YDHPSGAVVF---THAGDDM  71
M.squamata     ------------AKLEPHKLAQTFDTRWVRVGDVEYDVTNF--KHPSGSVIFYMLSNTGADA  73
O.tauri        ------------AEKMEPAALAKTFARRYVVIEGVEYDVTDF--KHPSGTVIFYALSNTGADA  81
                             :        :                   * *  * .*:*

P.incisa       TDVFACFHAQTTWSQLRPFCIGDIV------EEEPMPALLKDFRELRTRLQQQGLFRSNK  166
M.polymorpha   TDSFKVFHSAKAWQFLQDLYIGDLY------NAEPVSELVKDYRDLRTAFMRSQLFKSSK  166
P.tricornutum  TDIFAAFHAPGSQSIMKKFYIGELLPETTG-KEPQQIAFEKGYRDLRSKLIMMGMFKSNK  123
T.pseudonana   TDIFAAFHAQGSQAMMKKFYIGDLIPESVEHKDQRQLDFEKGYRDLRAKLVMMGMFKSSK  131
M.squamata     TEAFNEFHMRSPKAWKMLKALPNRPAETPR-SQDPDGPMLEDFAKWRAQLEKEGFFKPSI  132
O.tauri        TEAFKEFHHRSRKARKALAALPSRPAKTAK-VDDAE--MLQDFAKWRKELERDGFFKPSP  138
               *: * *  .     .                         :          :

P.incisa       LYYLYKVASTLSLLAAALAVLITQRDSWLGLVGGAFLLGLFWQQSGWLADFLSHQVFTD   226
M.polymorpha   MYYVTKCVTNFAILAASLAVIAWS-QTYLAVLCSSFLLALFWQQCGWLSDFLSHQVTEN   225
P.tricornutum  WFYVYKCLSNMAIWAAACALVFYS-DRFWVHLASAVMLGTFFQQSGWLADFLSHQVFTK   182
T.pseudonana   MYYAYKCSFNMCMWLVAVAMVYYS-DSLAMHIGSALLLGLFWQQCGWLADFLSHQVFKQ   190
               : *          . .            :     :  :  :      *.*
```

Figure 1D

```
M.squamata      AHVAYRIAELAAMFALGCYIMSLG-----YPVVASIVFGAFFGARCGWVQHFTHNSLTGN 188
O.tauri         AHVAYRFAELAAMYALGTYLMYAR-----YVVSSVLVYACFFGARCGWVQHFXHSSLTGN 194
                **** ** * ***  *  *      * *  * *   *********.*  ****

P.incisa        RQWNNVMG-YFLGNVCQGFSTDWWKSKFYFHAVPN-ELDSDKAARDPIDTLPLLAWS 284
M.polymorpha    RSLNTYFGGLFWGNFAQGYSVGWWKTKYNYFHAATN-ECD-DKYQPIDPDIDTVPLLAWS 283
P.tricornutum   RKHGDLGG-LFWGNLMQGYSVQNWKNKINCHAVPNLHCSSAVAQDGDPDIDTMPLLAWS 241
T.pseudonana    RKYGDLVG-IFWGDIMQGFSMQWWKNKINCHAVPNLHNSSLDSQDGDPDIDTMPLLAWS 249
M.squamata      IWLDKRIQAATCG-FGLSTSGDMWNQMEKHHATPQ------KVRHDMDLDTTPAVAFF 240
O.tauri         IWWDKRIQAFTAG-FGLAGSGDMWNSMKHHATPQ------KVRHDMDLDTTPAVAFF 246
                                            *  .: **: * .***

P.incisa        SEMLDS------------------MSNSGARLFVRMQHYFFFPILLFARMSWCQQSVAHASDLSRTSKAG 336
M.polymorpha    KEILAT-------------------VDDQFFRSIISVQHLLFFFLPLLFLARFSWLHSSWAHASNFEMPRYMR 335
P.tricornutum   VQQAQSYQELQADGKDSGLVKFMIRNQSYFYFPILLLARLSWLNESFKCAFGLGAASENA 301
T.pseudonana    LKQAQSFREINK-GKDSTFVKYAIKFQAFTYFPILLLARISWLNESFKTAFGLGAASENA 308
M.squamata      KTAVED-----------------NRPRGFSRAWSRAQAWTEVFVTSGLLVQMFWIYVLHPQVARKKNYE 293
O.tauri         NTAVED-----------------NRPRGFSKYWLRLQAWTFIPVTSG-LVLLFWMFFLHPSKALKGGKYE 298
                 .                          .                       *

P.incisa        -----------VYELAYLALHYAWF--LGAAFSVLPPLKAVVFALLSQMFSGFLLSIVF 382
M.polymorpha    ------------WAEKASLLGHYGAS--IGAAFYIILPIPQAICWLFLSQLFCGALLSIVF 381
P.tricornutum   ALELKAKGLQYPLLEKAGILLHYAWMLTVSSGFGRFSFAYTAFYFLTATASCGFLLAIVF 361
T.pseudonana    KLELEKRGLQYPLLEKLGITLHYTWMFVLSSGFGRWSLPYSIMYFFTATCSSGLFLALVF 368
M.squamata      -----------EASWMILSHVLRTATIKYAGGYSWPVAYLWFSFGNWIAYMYLFAHF 339
O.tauri         -----------ELVWMLAAHVIRTWTIKAVTGFTAMQSYGLFLATSWVSGCYLFAHF 344
                                  .                        *

P.incisa        VQSHNGMEVYSDTK--DFVTAQIVSTRDILS-----NVWNDWFTGGLNYXEHHLFPTLP 435
M.polymorpha    VISHNGMDVYNDPR--DFVTAQVTSTRNIEG-----NFFNDWFTGGLNRQFHHHLFPSLP 434
```

Figure 1E

```
P.tricornutum   GLGHNGMATYNADARPDFWKLQVTTRNVTGGHGFPQAFVDWFCGGLQYGVDHHLFPSLP 421
T.pseudonana    GLGHNGMSVYDATTRPDFWQLQVTTRNIIGGHGIPQFFVDWFCGGLQYGVDHHLFPMMP 428
M.squamata      STSHTHLEVVPSDKHISWVNYAVDHTVDIDP----SKGYVNWLMGYLNCQV-HHLFPDMP 395
O.tauri         STSHTHLDVVPADEHLSWVRYAVDHTIDIDP----SQGWVNWLMGYLNCQV-HHLFPSMP 400
                 *:   :   *. :** :* ::*  *:   :     . .::: :  ***.:*

P.incisa        RHNLGKVQKSIMELCHKHGILVYENCGMATGTYRVLQRLADVAAFA------------ 480
M.polymorpha    RHNLAKVAPHVKALCARHGLHYEELSLGTGVCRVFNRIVEVAYAAKV------------ 481
P.tricornutum   RHNLAKTHALIVESFCKEWGVQYHEADLVDGTMEVLHHIGSVAGEFVVDFVRDGPAM--- 477
T.pseudonana    RNNIAKCHKLVESFCKEWGVKYHEADMWDGTVEVLQHLSKVSDDFLVEMVKDFPAM--- 484
M.squamata      QFRQPEVSRRFVAFAKKWNLNYKVLTYYGAWKATFTNLDTVGQHYYKHGKAHAH----- 449
O.tauri         QFRQPEVSRRFVAFAKKWNLNYKVMTYAGAWKATLGNLDNVGKHYYVHGQHSGKTA    456
                ..::.: :  ::  .::..:  *:  :  *                *

P.incisa        -MMAVTEGAGGVTAEVGLHKRSSQPRPA------APRSKLFTLDEVAKHDSPTDCWVVIR   53
M.squamata      -MPPRETTTPSVDHPVMDRITSLTGGAG------AGVPRKYTTADVEKHSTPDDCWLIVH   53
O.tauri         -MGTTARDAGAVTTRARRRGTGATSEASRVHAVDADARTYTAAEVATHARADDCWVIVR   59
M.polymorpha    -MPPHAPDSTGLGPEVFRLPDDAIPAQDR-----RSTQKKYSLSDVSKHNTPNDCWLVIW   54
D.discoideum    MMETNNENK--------------------------EKIKLYTWDEVSKHNQKNDLMIIVD   34
M.alpina        -MGTD----------------------------------KGKTFTWEELAAHNTEGDLLLAIR   28
P.tricornutum   -MAPDADKLRQRQTTAVAKHN-------------AATISTQERLCSLSSLKGEEVCID   44
                 *

P.incisa        RRVYDVTAWVPQHPCSNLIFVKAGRDCTQLFDSYHPLS--ARAVLDKFYIGEVDVRPGD  110
M.squamata      GKVYDVTSFVPRHPCSNMIWVKAGGDCTQLFDSYHPIK--TQAVLDKYYIGEVQRVSGD  110
O.tauri         GGVYDVTAFVPRHPCSNMIYVKAGGECTALFDSYHPEK--ARGVLEKYRIGDLTREEGS  116
M.polymorpha    GKVYDVTSWVKVHPCS-SLIFVKAGQDSTQLFDSYHPLY--VRKLLAQFCIGELQTSAGD  111
D.discoideum    GKVYNITKWVPLHPCSEDILLLSAGRDATNLFESYHPMTDKHYSLIKQYEIGYISSYEHP   94
M.alpina        GNVYDVTKFLSRHPCSTDTLLLGAGRDVTPVFEMYHEFG--AADAIMKKYYVGTIVSNELP   87
P.tricornutum   GIIYDLQSFD---IPCS-ETIKMFGGNDVTVQYKMIHPYH-TEKHLEKMKRVGKVTDFVCE  100
                   *                                
```

```
P.incisa        :*:::  ..    ****  .  :    *    : ..    **** .          :*:  ..
M.squamata      EQF---LVAFE-EDTEEGQFYTVLKKRVEKYFRGEQAQPRATGAMYAKSITILAGLALSFY      167
O.tauri         EKK---IIEYN-DDMKKGKFYMDCKVAVEKYFKDTKQDPRVHVEMYVKTFVILAGVAVCHY      167
M.polymorpha    AADGDIVEYAKDDLKDGAFFADCKAGAAKYFKENKLDPRVHWEMYAKTAAILVGIVVGHY      176
D.discoideum    EKFK-SSTLEYAGEEHEVFYHTLKQRVETYFRKQINPRYHPQMLVKSAVIIGTLLLCYY      170
M.alpina        KYVE--------KSEFYSTLKQRVRKHFQTSSQDPKVSVGVETRMVLIYLFFVTYY         143
P.tricornutum   IFPE--------PTVFHKTIKTRVEGYFKDRNKDPKNRPEIWGRYALIFGSLIASYY        136
                YKFD--------TEFEREIKREVFKIVRRGK----DFGTLGWFFRAFCYIAIFFY          143
                                                                       .*

P.incisa        GTFFAF---SSAPASLLSAVLLGICMAEVGVSIMHDANHGAFARNTWASHALGATLDIVG      224
M.squamata      CSFFLT---SSFLVSAVFAALHGMWKAEVGVSIQHDANHGAYGKSRGFLHAMQLTLDVVG      224
O.tauri         YSFFAPG--VSFGAALAFAALHGTCKAEVGVSIQHDANHGAYGNSRTWLHAMQLTLDVVG      234
M.polymorpha    FGFFWS---QNVLLSMELASIMGFCTAEVGMSIMHDCNHGSYTQSTLLGYVMGATLDLVG      227
D.discoideum    LSQFS---TDRFWLNCIFAVLYGVANSLFGLHTMHDCHTAITHNPMTWKILGATFDLFA     200
M.alpina        AQLFVPFVVERTWLQVVFAIIMGFACAQVGLNPLHDASFSVTHNPTVWKILGATHDFFN     196
P.tricornutum   LQYHWVT---TGTSWLLAVAYGISQAMIGMNVQHDANHGATSKRPWVNDMLGLGADFIG      199
                                                  ** :                 :

P.incisa        -ASSFMWRQHVYGHHAYTNVDGQDPDLRVK-DPDVR--RVTKFQPQQSYQAYQHIYLAF      280
M.squamata      -ASSFMWRQHVYGHHAYTNVEGVDPDIRCAPEKDIR--RVNEHQPHESYHPLQHVYLFF      281
O.tauri         -ASSFMWKQHVACHHAYTNVEGIDPDIRCS-EKDIR--RVNEHQPHEPYHVFQHVYLAF      290
M.polymorpha    -ASSFMWRQHVAGHHSFTNIDHYDPDIRVK-DPDLR--RVTSQQPRRWFHEYQHIYLGV      283
D.discoideum    GASFYAWCHOHVT-CHHLYTNVRNADPDLGQG-EIDFR--RVTPYQARSWYHKYQHIYAPI    257
M.alpina        GASYLVWMYCHMLGHHPYTNIAGADPDVSTS-EPDVR--RIKPNQKWFVNHHNQHMFVPF     253
P.tricornutum   -GSKWLWQEGHWT--HHAYTNHAEMDPDSFGAEPMLLFNDYPLDHFARTWLHRFQAFFYMP    257
                     *         **  *  *: .   :  :       ****                      ::

P.incisa        LYGLLAIKSVLLDDFMALSSGAIGSVKVAK------LTPGEKLVFWGGKALWLGYFVLLPV     335
M.squamata      AYGLLSFKSCFADDFNAWASGRIGWVKVAK------FTRGEAVSFWGSKVLWAFYYLYLPA     336
O.tauri         MYGLLSLKSCFVDDFNAYFSGRIGWVKVMK------FTRGEAIAFWGTKLLWAAYYLALPL     345
M.polymorpha    LYGVLALKSVLIDDFSAFFSGAIGPVKIAQ------MTPLEMGVFWGGKVVYALYMFLLPM     338
D.discoideum    LYGVYALKYRIQDHEIFT-KKSNGAIRYSP------ISTIDTAIFILGKLVFIISRFILPL    311
M.alpina        LYGLL AFKVRIQDINLYFVKTNDAIRVNP------ISTWHTVMFWGGKAFFAWYRLIVPL     308
                . .:              . :                                 :
```

Figure 1F

```
                 VLAGYWLSAVENPQILDLQQRGALSVGIRLDNAFIHSRRKYAVFWRAVYIAVNVLAPFYT  317
P.tricornutum
                                                                    *

P.incisa         VKSRHSWPLLAACWLLSEFVTGWMLAFMFQVAHVTSDVSYLEADKTG--------KVPR  386
M.squamata       TYSPHSGLRIVALVTITEVITGWLLAFMFQVAHVVGDVRFFKLSEEG--------KLNL  387
O.tauri          KMSHRPLGELLALWAVTEFVTGWLLAFMFQVAHVGEVHFFTLDAKN---------RVNL  396
M.polymorpha     MYGQYNILTFIGLYILSQLVAGWTLALFFQVAHVVDDAVFPVAETDGG-------KAKIPS 392
D.discoideum     IYN-HSFSHLICFFLISELVLGWYLAISFQVSHVVEDLQFMATPEIFDGADHPLPTTFNQ 370
M.alpina         QY--LSLSKVLLLFTVADMVSSYWLALTFQANHVVEEVQWPLPDE----------NGIIQK 357
P.tricornutum    NSGEWSWRVFGNIMLMGVAESLALAVLFSLSHNFESADRDPTAPLKK--------TGEPV 370
                                   *                                *

P.incisa         GWAAAQAATTADFAHGSWFWTQISGGLNYQVYHHLFPGICHLHYPAIAPIVLDTCKEFNV 446
M.squamata       GWGESQLYSSADFAHGSKFWMHFSGGLNYQVAHHLFPGVCHCHYPAIAPIIMKVAKEYGL 447
O.tauri          GWGEAQLMSSADFAHGSKFWTHFSGGLNYQVVHHLFPGVCHVHYPALAPIIKAAAEKHGL 456
M.polymorpha     GWAEMQVRTTTNFSSRSMFWTHISGGLNHQIEHHLFPGVCHVHYPSIQPIVKATCDEFNV 452
D.discoideum     DWAILQVKTTQDYAQDSVLSTFFSGGLNLQVIHHCFPTIAQDYYPQIVPILKEVCKEYNV 430
M.alpina         DWAAMQVETTQDYAHDSHLWTSITGSLNYQAVHHLFPNVSQHHYPDILALIKDTCSEYKV 417
P.tricornutum    DWFKTQVETSCTYG--GFLSGCFTGGLNFQVEHHLFPRMSSAWYPYIAPKVREICAKHGV 428
                  *    *                   * * ***               *

P.incisa         PYHVYPTFVRALAAHFKHLKDMGAPTAIPSLATVG--------- 481
M.squamata       EYAVYPTFWSALSAHFTHLKNVGQKTYVPSLQTIG--------- 482
O.tauri          HYQIYPTFWSALRAHFRHLANVGRAAYVPSLQTVG--------- 491
M.polymorpha     PYTSYPTFWAALRAHFQHLKNVG---LQDGLRLDG--------- 484
D.discoideum     TYHYKPTFTEAIKSHINYLYKMGNDPDYVRKPVNKND------- 467
M.alpina         PYLVKDTFWQAFASHLEHLRVLGLRP----------KEE----- 446
P.tricornutum    HYAYYPWIHQNFLSTVRYMHAAGTGANWRQMARENPLTGRA    469
                   *   ::   :   :          ::  *
```

```
PiELO1  ------------------------------------------MA-------LTAAWHKYDAIVSRFVFDG  21   SEQ. ID NO. 7
OtELO1  ---------------------------------MSGLRAPNFLHRFWTKWDYAISKVVFTC          28   SEQ. ID NO. 57
MpELO2  ----------------------------------------MEAYEMVDSFVSKTVFET            18   SEQ. ID NO. 58
PpELO1  ----------------------------------------MEVERFYGELDGKVSQG             18   SEQ. ID NO. 59
MpELO2  MATKSGSGLLEWIAVAAKMQARSSPEGETVGGNRMGSGNGAEWTTSLIHAFLNATNGKS            60   SEQ. ID NO. 60
ThrELO1 --------------------------------------MDVVEQQWRRFVDAVDNGIVEF          22   SEQ. ID NO. 61

PiELO1  LRR-----------VGLQEIQGHPSVITAHLPFIASPTPQVTFVLAYLLIVV                    62
OtELO1  AD------------SFQWDIGPVSSSTAHLPAIESPTPLVTSLLFYLVTVF                    67
MpFiLO2 -----LQRLRG--GVVLTES-AITKGLPCVDSPTPIVAGLSSYLTFVF                       58
PpELO1  -----VNALLGSFGVELTDT-PTTKGLPLVDSPTPIVLGVSVYLTIVI                       60
MpELO2  GGASKVRPLEERIGEAVFRVLEDVVGVDIRKPNPVTKDLPMVESPVFVLACISLYLLVVW           120
ThrELO1 ------MEHEEPNKLNEGK-LSTSTEEMMALIVGYLAFVV                              55

PiELO1  CGVAALRTRKSSAPREDPAWLRLAVQAHNIVLISLSAYMSSAACYYAWKYGYRFWGTNYS           122
OtELO1  LWYGRL-TRSSEKKIREPTWLRREPAILNLFVIFHNFVCFALSLYMCLGCVAQAYQNGYTLWGNEFK    126
MpELO2  LGLIVIKSLDLKPRSKEPAILNLFVIFHNFVCFALSLYMCVGIVRQAILNRYSLWGNAYN          118
PpELO1  GGILWIKARDLKPRASEPFLLQALVLVHNLFCFALSLYMCVGIAYQAITWRYSLWGNAYN          120
MpELO2  LWSSHIKASGQKPRKEDPLALRCSVIAHNLFLCCLSLSFMCVGLIAAARHYGYSVWGNYYR         180
ThrELO1 LGSAFMKAFVDK------PFELKFEKLVHNIFLTGLSMYMATECARQAYLGGYKLFGNPME         110

PiELO1  P-----KERDMGGLIYTF...LIMLLKGKVECVSF...STIWWAIAY                        178
OtELO1  A-----TETQLALYIYIF...YIMLLKNNLRQVS...SFIWWIIAR                         182
MpELO2  P-----KEVQMGHLLYLF...VIMILKRNTRQ...SFIWWIIAY                           174
PpELO1  P-----KEKEMAILVYLF...VIMILKRSTRQ...SLIWWAIAH                           176
MpELO2  E-----REPAMNLLIYVF...AIMLFRRNLR...AMIWWIICY                            236
ThrELO1 KGTESHAPGMANIIYIF...VFMILGKKWKQ...SFIWGIIAR                            170

PiELO1  VAPGGDAWYCCF...LLATLIGKDAKARRKYLWWGRYI...VTMM                          238
OtELO1  RAPGGDAYFSAALNS...LLSTLIGKEDPKRSNYLWWGRHL...FFNV                       242
MpELO2  HAPGGEAYFSAALNS...LLAATLGKNEKARRKYLWWCKYI...VLNM                       234
PpELO1  HAPGGEAYWSAALNS...FLAACLRSSPKLKNKYLFWGRYI...EMLNL                      236
MpELO2  RFPGADSYFSAAMSG...LLAATVARDEKRRRKYLFWGKYI...LSFI                       296
ThrELO1 FAPGGDAYFSTI...ASTTLGYTFMRPLR----PYI...NAMV                           224
```

```
PiElO1    LEAAYTWA-YSPYPKFLSKLLFFYMITLLALFANFYAQKHGSS-----RAAKQKLQ  288
OtElO1    LQALYCAS-FSTYPKFLSKILLVYMMSLLGLFGHFYYSKHIAA-----AKLQKKQQ  292
MpElO1    IQAYYDIKNNSPYPQFLIQILFYYMISLLALFGNFYVHKYVSAPAKPAKIKSKKAE  290
PpElO1    VQAYYDMKTNAPYPQWLIKILFYYMISLLFLFGNFYVQKYIKP--SDGKQKGAKTE  290
MpElO2    GQAIYAMWKFEYYPKGFGRMLFFYSVSLLAFFGNFFVKKKYSNA-----SQPKTVKVE  348
ThrElO1   VQSVYDYYNPCDYPQPLVKLLFWYMLTMLGLFGNFFVQQYLKP-----KAPKKQKTI  276
          : :   *      *  : : ::  *: ::::*: ..* :             *

Figure 5B
```

DESATURASES OF A GREEN MICROALGA AND USES THEREOF

REFERENCE TO CO-PENDING APPLICATIONS

Priority is claimed as a continuation of U.S. patent application Ser. No. 13/520,607; filed on Sep. 20, 2012 now abandoned; which is a 371 of international application number PCT/IL2011/000006, filed on Jan. 5, 2011; which claims priority to U.S. provisional patent application Ser. No. 61/292,185, filed on Jan. 5, 2010.

FIELD OF INVENTION

This invention is directed to, inter alia, proteins having Δ12, Δ6, or Δ5 desaturase activity, isolated DNA molecules encoding the same, and methods of making and utilizing the same.

BACKGROUND OF THE INVENTION

Very long-chain polyunsaturated fatty acids (VLC-PUFA) of 20 or 22 carbon atoms are indispensable components of human nutrition. They are necessary for normal life-long physiology and benefit the well-being of the human body. Nutritionally important VLC-PUFAs include the ω3-fatty acids, eicosapentaenoic acid (EPA, 20:5ω3) and docosahexaenoic acid (DHA, 22:6ω3) and the ω6-fatty acid, arachidonic acid (ARA, 20:4ω6) and dihomo-y-linolenic acid (DGLA, 20:3ω6) which are the major components of membrane phospholipids of the retina, brain and testis. ARA and DHA are the predominant fatty acids in the human brain and breast milk. ARA is necessary for normal fetal growth, and cognitive development in infants. Many studies highly suggested supplementation of infant formula with DHA and ARA. Besides the structural function in membranes, ARA is the primary substrate in eicosanoids biosynthesis which regulates many physiological processes such as homeostasis, reproduction, immune and inflammatory responses.

Microalgae are the most efficient producers and one of the richest sources of VLC-PUFAs. Furthermore, algae can be used as sources of genes for the implementation of VLC-PUFA biosynthesis in genetically engineered oil crops. The genetic information on enzymes involved in the biosynthesis of VLC-PUFA in some algae led to in vivo applications of VLC-PUFA production in seed oil. The gene pool of the green freshwater microalga *Parietochloris incisa* (Trebouxiophyceae) is of special interest since it is the only known microalga able to accumulate extraordinary high amounts of ARA-rich triacylglycerols (TAG). When *P. incisa* is cultivated under nitrogen starvation, the condition triggering storage oil accumulation, ARA constitutes about 60 percent of total fatty acids (TFA) and over 95 percent of cellular ARA is deposited in TAG in cytoplasmic lipid bodies.

The biosynthesis of VLC-PUFA in microalgae follows two major pathways, designated as ω6 and ω3. In these pathways, linoleic acid (LA; 18:2ω6) and α-linolenic acid (ALA; 18:3ω3) go through sequential, Δ6 desaturation, Δ6 elongation and Δ5 desaturation, yielding ARA and EPA, respectively. E.g., in the red microalga *Porphyridium cruentum* and the green microalga *P. incisa*, oleic acid (18:1) is first desaturated to LA and .gamma.-linolenic acid (GLA, 18:3ω6) through Δ12 and Δ6 desaturations, followed by elongation to 20:3ω6 and Δ5 desaturation to yield ARA via the ω6 pathway. In *P. incisa*, the extraplastidial lipids, phosphatidylcholine (PC) and the betaine lipid, diacylglyceroltrimethylhomoserine (DGTS), are involved in the Δ12 and, subsequently, the Δ6 desaturations, whereas phosphatidylethanolamine (PE) along with PC are the suggested major substrates for the Δ5 desaturation of 20:3ω6 to 20:4ω6. The same enzymes are involved in the biosynthesis of VLC-PUFA through the ω3 pathway in the green microalga *Ostreococcus tauri*.

VLC-PUFAs may also be generated by an alternative Δ8 desaturation pathway. E.g., in the marine haptophyte *Isocrysis galbana* and in the fresh water euglenophyte *Euglena gracilis*, where LA and ALA are first elongated by C18 Δ9-specific fatty acid elongase followed by sequential Δ8 and Δ5 desaturations to ARA, DGLA or EPA. The extraplastidial Δ12 desaturase is an integral ER-bound protein which is responsible for the desaturation of oleic acid and production of LA, mainly on phosphatidylcholine (PC). Δ5 and Δ6 desaturases contain a fused cytochrome b5 domain in their N-terminus, serving as an electron donor, and introduce a double bond at a site closer to the carboxyl group than any of the pre-existing double bonds in the substrate fatty acid, thereby called 'front-end' desaturases. Desaturases with Δ6 or Δ5 activity have been isolated from various organisms, e.g., the nematode *C. elegans*, the fungus *Mortierella alpina*, the moss *Physcomitrella patens*, the liverwort *Marchantia polymorpha* and the algae *Phaeodactylum tricornutum*, *Thalassiosira pseudonana* and *Ostreococcus tauri*. Some of these desaturases have been introduced together with PUFA-specific elongases into constructs for transformation of yeast and oil seed plants to reconstitute VLC-PUFA biosynthesis in the heterologous organisms.

SUMMARY OF THE INVENTION

In one embodiment, the present invention provides an isolated protein comprising, an amino acid sequence set forth in SEQ ID NO: 1.

In another embodiment, the present invention further provides an isolated protein comprising, an amino acid sequence set forth in SEQ ID NO: 2.

In another embodiment, the present invention further provides an isolated protein comprising, an amino acid sequence set forth in SEQ ID NO: 3.

In another embodiment, the present invention further provides a composition comprising a protein comprising, an amino acid sequence set forth in SEQ ID NO: 1, a composition comprising a protein comprising, an amino acid sequence set forth in SEQ ID NO: 2, a composition comprising a protein comprising, an amino acid sequence set forth in SEQ ID NO: 3, or a composition comprising any combination thereof.

In another embodiment, the present invention further provides a transgenic plant, a transgenic seed, a transformed cell, or a transgenic alga transformed by a polynucleotide encoding: (1) a protein comprising, an amino acid sequence set forth in SEQ ID NO: 1, (2) a protein comprising, an amino acid sequence set forth in SEQ ID NO: 2, (3) a protein comprising, an amino acid sequence set forth in SEQ ID NO: 3, or a transgenic plant, a transgenic seed, or a transgenic alga transformed by any combination of the polynucleotides (1), (2), and (3).

In another embodiment, the present invention further provides a method of producing very long-chain polyunsaturated fatty acid (VLC-PUFA) in a plant, a plant cell, or an alga comprising the step of transforming a plant, an alga, or a plant cell with a polynucleotide encoding: (1) a protein comprising, an amino acid sequence set forth in SEQ ID NO: 1, (2) a protein comprising, an amino acid sequence set forth in SEQ ID NO: 2, (3) a protein comprising, an amino acid sequence set forth in SEQ ID NO: 3, or transforming a plant, a plant cell, or an alga with any combination of the polynucleotides (1), (2), and (3), thereby producing a VLC-PUFA in a plant, a plant cell, or an alga.

BRIEF DESCRIPTION OF THE DRAWINGS

FIGS. 1A through 1G depict the deduced amino acid sequences of *P. incisa* PiDes12 (A), PiDes6 (B), and PiDes5 (C) are aligned with their closest homologs using CLUSTAL W (1.83) multiple sequence alignment program (default). Conserved motifs characteristic of each desaturase sequence are highlighted. GeneBank accession numbers for the sequences are: A) *C. reinhardtii* (XP_001691669); *C. vulgaris* (BAB78716), *G. hirsutum* (AAL37484), *S. oleracea* (BAC22091), *O. europaea* (AAW63040). B) *M. polymorpha* (AAT85661), *P. tricornutum* (AAL92563), *T. pseudonana* (AAX14505), *O. tauri* (AAW70159), *M. squamata* (CAQ30479). C) *O. tauri* (CAL57370), *M. squamata* (CAQ30478), *M. polymorpha* (AAT85663), *D. discoideum* (BAΔ37090), *M. alpina* (AAC72755), *P. tricornutum* (AY082392); and FIGS. 1A-1G are collectively referred to as just FIG. 1.

FIGS. 5A and B depict the amino acid sequence of *P. incisa* PiELO1 aligned with its closest homologs using CLUSTAL W (1.83) multiple sequence alignment program (default). Conserved motifs characteristic of PUFA elongase sequences are highlighted. GeneBank accession numbers for the sequences are OtELO1 (*O. tauri*, AAV67797), MpELO1 (*M. polymorpha*, AAT85662), PpELO1 (*P. patens*, AAL84174), MpELO2 (*M. polymorpha*, BAE71129), and ThrELO1 *Thraustochytrium* sp. FIN-10, ABC18313); since FIGS. 5A and 5B are the same figure, they will be collectively referred to as FIG. 5.

DETAILED DESCRIPTION OF THE INVENTION

Figure 2:
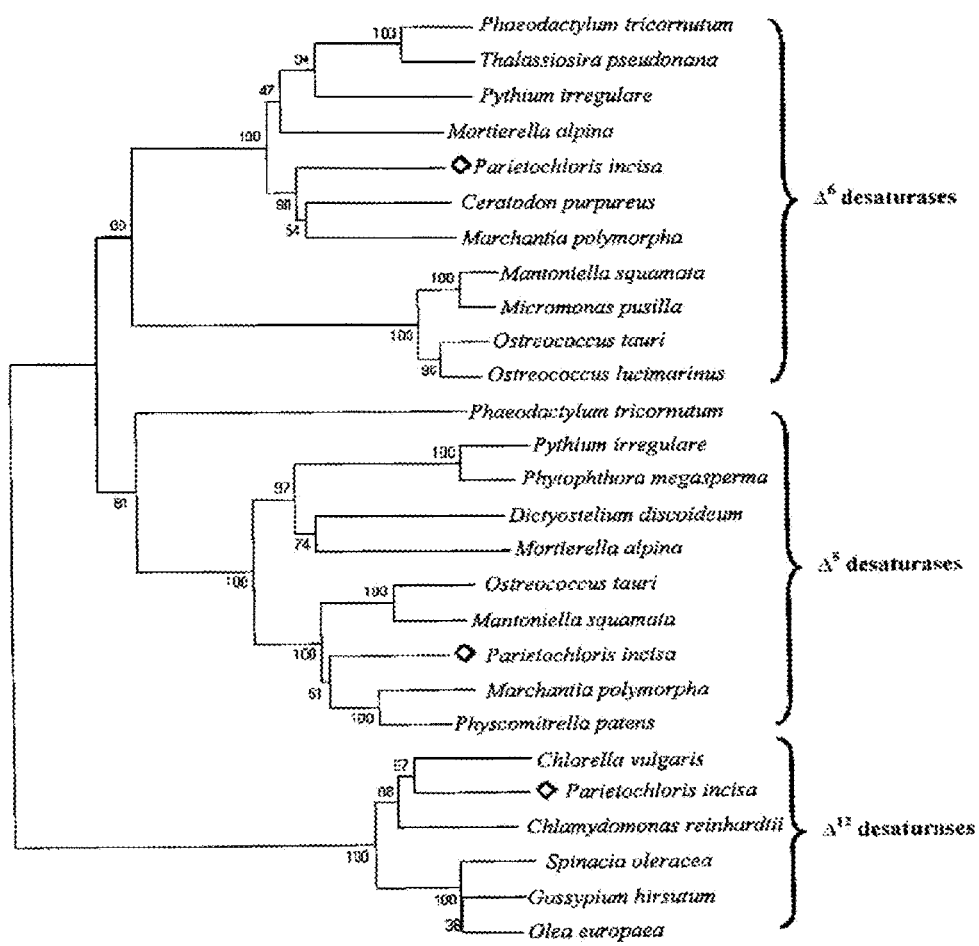
FIG. 2 is an unrooted phylogram of PiDes12, PiDes6, PiDes5 and some functionally characterized Δ12, Δ6 and Δ5 desaturases (vertebrate and invertebrate desaturases are not included). The alignment was generated by the CLUSTAL W program and the unrooted phylogram was constructed in the neighbor-joining method using the MEGA4 software [47]. GeneBank sources of the sequences are: BAB78716 (Δ12, *Chlorella vulgaris*), XP_001691669 (Δ12, *C. reinhardtii*), BAC22091 (Δ12, *Spinacia oleracea*), AAL37484 (Δ12, *Gossypium hirsutum*), AAW63040 (Δ12, *Olea europaea*), CAB94993 (Δ6, *Ceratodon purpureus*), AAT85661 (Δ6, *M. polymorpha*), BAΔ85588 (Δ6, *M. alpina*), AAL92563 (Δ6, *P. tricornutum*), AAX14505 (Δ6, *T. pseudonana*), (Δ6, *Pythium irregulare*), CAL57370 (Δ5, *O. tauri*), AAT85663 (Δ5, *M. polymorpha*), AAL13311 (Δ5, *P. irregulare*), CAD53323 (Δ5, *Phytophthora megasperma*), BAΔ37090 (Δ5, *Dictyostelium discoideum*), AAC72755 (Δ5, *M. alpina*), CAQ30478 (Δ5, *M. squamata*), CAQ30479 (Δ6, *M. squamata*), AAW70159 (M, *O. tauri*), CS020055 (Δ5, *P. patens*).

In one embodiment, the present invention provides an isolated protein. In another embodiment, the present invention provides that the isolated protein is a polypeptide. In another embodiment, the present invention provides that the isolated protein is an enzyme. In another embodiment, the present invention provides that the isolated protein is a desaturase. In another embodiment, the present invention provides that the isolated protein is an algal desaturase. In another embodiment, the present invention provides that the isolated protein is a microalgae desaturase. In another embodiment, the present invention provides that the isolated protein is a Δ12 desaturase. In another embodiment, the present invention provides that the isolated protein is a Δ6 desaturase. In another embodiment, the present invention provides that the isolated protein is a Δ5 desaturase. In another embodiment, the present invention provides that the isolated protein is a microalgae desaturase produced in a plant cell. In another embodiment, the present invention provides that the isolated protein is a microalgae desaturase produced in an algal cell.

In another embodiment, the present invention provides a Δ12 desaturase comprising the amino acid sequence:

(SEQ ID NO: 1)
MGKGGCYQAGPPSAKKWESRVPTAKPEFTIGTLRKAIPVHCFERSIPRSF

AYLAADLAAIAVMYYLSTFIDHPAVPRVLAWGLLWPAYWYFQGAVATGVW

VIAHECGHQAFSPYQWLNDAVGLVLHSCLLVPYYSWKHSHRRHHSNTGST

TKDEVFVPREAAMVESDFSLMQTAPARFLVIFVSLTAGWPAYLFANASGR

KYGKWANHFDPYSPIFTKRERSEIVVSDVALTVVIAGLYSLGKAFGWAWL

VKEYVIPYLIVNMWLVMITLLQHTHPELPHYADKEWDWLRGALATCDRSY

GGMPDHLHHHIADTHVAHHLFSTMPHYHAQEATEAIKPILGKYYKQDKRN

VWAALWEDFSLCRYVAPDTAGSGILWFRA.

In another embodiment, the present invention provides a Δ6 desaturase comprising the amino acid sequence:

```
                                                (SEQ ID NO: 2)
MCQGQAVQGLRRRSSFLKLTGDAIKGAVAAISDFNKLPAATPVFARRSLS

DSALQQRDGPRSKQQVTLEELAQHNTPEDCWLVIKNKVYDVSGWGPQHPG

GHVIYTYAGKDATDVFACFHAQTTWSQLRPFCIGDIVEEEPMPALLKDFR

ELRTRLQQQGLFRSNKLYYLYKVASTLSLLAAALAVLITQRDSWLGLVGG

AFLLGLFWQQSGWLAHDFLHHQVFTDRQWNNVMGYFLGNVCQGFSTDWWK

SKHNVHHAVPNELDSDSKAARDPDIDTLPLLAWSSEMLDSMSNSGARLFV

RMQHYFFFPILLFARMSWCQQSVAHASDLSRTSKAGVYELAYLALHYAWF

LGAAFSVLPPLKAVVFALLSQMFSGFLLSIVFVQSHNGMEVYSDTKDFVT

AQIVSTRDILSNVWNDWFTGGLNYQIEHHLFPTLPRHNLGKVQKSIMELC

HKHGLVYENCGMATGTYRVLQRLANVAAEA
```

In another embodiment, the present invention provides a AS desaturase comprising the amino acid sequence:

```
                                                (SEQ ID NO: 3)
MMAVTEGAGGVTAEVGLHKRSSQPRPAAPRSKLFTLDEVAKHDSPTDCWV

VIRRRVYDVTAWVPQHPGGNLIFVKAGRDCTQLFDSYHPLSARAVLDKFY

IGEVDVRPGDEQFLVAFEEDTEEGQFYTVLKKRVEKYFRENKLNPRATGA

MYAKSLTILAGLALSFYGTFFAFSSAPASLLSAVLLGICMAEVGVSIMHD

ANHGAFARNTWASHALGATLDIVGASSFMWRQQHVVGHHAYTNVDGQDPD

LRVKDPDVRRVTKFQPQQSYQAYQHIYLAFLYGLLAIKSVLLDDFMALSS

GAIGSVKVAKLTPGEKLVFWGGKALWLGYFVLLPVVKSRHSWPLLAACWL

LSEFVTGWMLAFMFQVAHVTSDVSYLEADKTGKVPRGWAAAQAATTADFA

HGSWFWTQISGGLNYQVVHHLFPGICHLHYPAIAPIVLDTCKEFNVPYHV

YPTFVRALAAHFKHLKDMGAPTAIPSLATVG
```

In another embodiment, the desaturase of the present invention comprises an amino acid sequence that is at least 60% homologous to the amino acid sequence of SEQ ID NO: 1, SEQ ID NO: 2, or SEQ ID NO: 3. In another embodiment, the desaturase comprises an amino acid sequence that is at least 70% homologous to the amino acid sequence of SEQ ID NO: 1, SEQ NO: 2, or SEQ ID NO: 3. In another embodiment, the desaturase comprises an amino acid sequence that is at least 75% homologous to the amino acid sequence of SEQ ID NO: 1, SEQ ID NO: 2, or SEQ ID NO: 3. In another embodiment, the desaturase comprises an amino acid sequence that is at least 80% homologous to the amino acid sequence of SEQ ID NO: 1, SEQ ID NO: 2, or SEQ ID NO: 3. In another embodiment, the desaturase comprises an amino acid sequence that is at least 85% homologous to the amino acid sequence of SEQ ID NO: 1, SEQ ID NO: 2, or SEQ ID NO: 3. In another embodiment, the desaturase comprises an amino acid sequence that is at least 90% homologous to the amino acid sequence of SEQ ID NO: 1, SEQ ID NO: 2, or SEQ ID NO: 3. In another embodiment, the desaturase comprises an amino acid sequence that is at least 95% homologous to the amino acid sequence of SEQ ID NO: 1, SEQ ID NO: 2, or SEQ ID NO: 3. In another embodiment, the desaturase comprises an amino acid sequence that is at least 98% homologous to the amino acid sequence of SEQ ID NO: 1, SEQ ID NO: 2, or SEQ ID NO: 3.

In another embodiment, the desaturase of the present invention comprises an amino acid sequence that is at least 60% identical to the amino acid sequence of SEQ ID NO: 1, SEQ ID NO: 2, or SEQ ID NO: 3. In another embodiment, the desaturase comprises an amino acid sequence that is at least 70% identical to the amino acid sequence of SEQ ID NO: 1, SEQ ID NO: 2, or SEQ ID NO: 3. In another embodiment, the desaturase comprises an amino acid sequence that is at least 75% identical to the amino acid sequence of SEQ ID NO: 1, SEQ ID NO: 2, or SEQ ID NO: 3. In another embodiment, the desaturase comprises an amino acid sequence that is at least 80% identical to the amino acid sequence of SEQ ID NO: 1, SEQ ID NO: 2, or SEQ ID NO: 3. In another embodiment, the desaturase comprises an amino acid sequence that is at least 85% identical to the amino acid sequence of SEQ ID NO: 1, SEQ ID NO: 2, or SEQ ID NO: 3. In another embodiment, the desaturase comprises an amino acid sequence that is at least 90% identical to the amino acid sequence of SEQ ID NO: 1, SEQ ID NO: 2, or SEQ ID NO: 3. In another embodiment, the desaturase comprises an amino acid sequence that is at least 95% identical to the amino acid sequence of SEQ ID NO: 1, SEQ ID NO: 2, or SEQ ID NO: 3. In another embodiment, the desaturase comprises an amino acid sequence that is at least 98% identical to the amino acid sequence of SEQ ID NO: 1, SEQ ID NO: 2, or SEQ ID NO: 3.

In another embodiment, the desaturase as described herein comprises at least a portion of the amino acid shown in SEQ ID. NO: 1, SEQ ID NO: 2, or SEQ ID NO: 3. In another embodiment, the desaturase as described herein is a variant of SEQ ID. NO: 1, SEQ ID NO: 2, or SEQ ID NO: 3. In another embodiment, the term "variant" in relation to a certain sequence means a protein or a polypeptide which is derived from the sequence through the insertion or deletion of one or more amino acid residues or the substitution of one or more amino acid residues with amino acid residues having similar properties, e.g., the replacement of a polar amino acid residue with another polar amino acid residue, or the replacement of a non-polar amino acid residue with another non-polar amino acid residue. In all cases, variants must have a desaturase function as defined herein.

In another embodiment, the desaturase as described herein further comprises a leader peptide. In another embodiment, the leader peptide allows the polypeptide to be specifically located or targeted to a target organelle within the cell. In another embodiment, the desaturase as described herein further comprises a sequence motif responsible for microsomal localization. In another embodiment, a desaturase as described herein further comprises chemical modification such as glycosylation that increases its stability. In another embodiment, a desaturase as described herein further comprises a peptide unrelated to desaturase which increases its stability.

In another embodiment, the present invention provides an isolated PUFA desaturase. In another embodiment, the present invention provides an isolated polypeptide comprising a functional long chain polyunsaturated fatty acid (PUFA) desaturase. In another embodiment, the present invention provides that the polypeptide has the function of desaturating a chain longer than 18 carbons fatty acid. In another embodiment, the present invention provides that the polypeptide has the function of desaturating a chain longer than 20 carbons fatty acid.

In another embodiment, the present invention provides an isolated PUFA desaturase comprising a fused N-terminal cytochrome b5 domain. In another embodiment, the present invention provides an isolated PUFA desaturase which desaturates ω6 substrates. In another embodiment, the present invention provides an isolated PUFA desaturase which desaturates both ω3 substrates. In another embodiment, the present invention provides an isolated PUFA desaturase which desaturates both ω3 and ω6 substrates. In another embodiment, the present invention provides an isolated PUFA desaturase encoded by SEQ ID NO: 1 (PiDes12 or Δ12). In another embodiment, the present invention provides an isolated PUFA desaturase encoded by SEQ ID NO: 2 (PiDes6 or Δ6). In another embodiment, the present invention provides an isolated PUFA desaturase encoded by SEQ ID NO: 3 (PiDes5 or Δ5). In another embodiment, the substrate for the present invention isolated PUFA desaturase is 18:2ω6, 20:3ω6, 20:4ω3, and 20:3ω3

In another embodiment, the present invention provides an isolated PUFA desaturase which desaturates 20:3ω3 to a non-methylene-interrupted 20:4$^{Δ5}$. In another embodiment, the present invention provides that PiDes5 desaturates 20:3ω3 to a non-methylene-interrupted 20:4$^{Δ5}$. In another embodiment, the present invention provides that PiDes5 converts 20:4ω3 into the respective Δ5 product, 20:5ω3 (EPA) as well as the added 18:1 into the non-methylene-interrupted 18:2$^{Δ5,9}$.

In another embodiment, the present invention provides a protein comprising a desaturase activity. In another embodiment, the present invention provides a protein consisting a desaturase activity. In another embodiment, the present invention provides that the protein of the invention is a recombinant desaturase. In another embodiment, the present invention provides that the desaturase is a polyunsaturated fatty acid (PUFA)-specific desaturase. In another embodiment, the present invention provides that the desaturase desaturates precursors of arachidonic acid. In another embodiment, the present invention provides that the desaturase desaturates precursors of EPA. In another embodiment, the present invention provides that the desaturase desaturates immediate precursors of arachidonic acid (ARA). In another embodiment, the present invention provides that the protein as described herein is used to elevate PUFA levels in animals, thereby providing a ready source of PUFAs.

In another embodiment, the expression and/or transcription of the desaturase as described herein is up-regulated during nitrogen starvation. In another embodiment, the expression and/or transcription of the desaturase as described herein is up-regulated under oleogenic conditions. In another embodiment, oleogenic conditions comprise the presence of a Δ6 substrate for Δ6 or Δ5 fatty acid desaturase. In another embodiment, oleogenic conditions comprise 18:2ω6 and 20:3ω6. In another embodiment, oleogenic conditions comprise nitrogen starvation. In another embodiment, the expression and/or transcription level of the desaturases as described herein correlates with the production of ARA precursors. In another embodiment, oleogenic conditions comprise nitrogen starvation. In another embodiment, the expression and/or transcription level of the desaturases as described herein correlates with the production of DGLA precursors, EPA precursors, DHA precursors, ARA precursors, or any combination thereof.

In another embodiment, the present invention provides an isolated polynucleotide encoding the protein as described herein. In another embodiment, an isolated polynucleotide is an isolated DNA molecule. In another embodiment, an isolated polynucleotide is an isolated cDNA molecule. In another embodiment, the isolated polynucleotide comprises a sequence encoding the protein as described herein. In another embodiment, the isolated polynucleotide comprises a DNA sequence encoding a desaturase as described herein. In another embodiment, the isolated polynucleotide comprises a DNA sequence encoding a polypeptide comprising a desaturase activity. In another embodiment, the isolated polynucleotide comprises a DNA sequence encoding a polypeptide consisting a desaturase activity.

In another embodiment, the isolated polynucleotide comprises a DNA sequence comprising the sequence:

```
                                    (SEQ ID NO: 4, PiDes12)
atggggaaaggaggctgttaccaggccgggcctcctagcgcaaagaaatg ggagagtagggtgcccactgccaaacccgagttcacgatcggaaccctcc gcaaagctataccggtccactgcttcgaaccggtccatccctcggtcattg cctaccttgcggcagacctggcggctattgcggtcatgtactacctgagc actttcatcgatcatcccgccgtgccgcgggtcctggcctggggtttgct gtggcctgcctactggtacttccaaggtgctgtggcgacaggcgtctggg tgattgctcacgagtgcggccaccaggcgttctcgccctaccagtggctc aacgacgctgtggggcttgtgctgcactcctgcttgctggtgccctatta ctcctggaagcactcacacagacggcaccactccaacaccggaagcacca ccaaggatgaggtgtttgtccccccgggaagcagccatggtggagtcggac ttctccttgatgcagacagctcccgcgcggttcctggtcatcttcgtctc gctgaccgctggctggcctgcctacctgtttgccaatgcatctggccgca agtatggcaagtgggccaaccactttgacccctactcacccatcttcacc aagcgcgagcgcagcgagatcgttgtcagcgatgtcgcgctgacggtggt catcgcggggctctactcgctgggcaaggcgtttggctgggcctggctgg tcaaggagtatgtgatcccctacctcatcgtcaacatgtggctggtcatg atcacgctgctgcagcacacgcaccccgagctgccgcactacgccgacaa ggagtgggactggctgcgcggcgcgctggccacctgcgatcgcagctacg gcggcatgccggaccacctgcaccaccacatcgccgacacgcacgtcgct caccacctgttctccaccatgccgcactaccatgcgcaggaggcgactga ggcgatcaagcccatcctgggcaagtactacaagcaggacaagcgcaacg tctgggcagcgctctgggaggatttcagcctgtgccgctatgtggcgcct gacacagcaggctcgggcatcctgtggttccgcgcttga
```

In another embodiment, SEQ ID NO: 4 encodes the amino acid sequence of SEQ ID NO: 1.

In another embodiment, the isolated polynucleotide comprises a DNA sequence comprising the sequence:

```
                                    (SEQ ID NO: 5, PiDes6)
atgtgccagggacaggcagtccagggtctgaggcgccggagttcattatg aagctcaccggggacgctatcaaaggggccgttgccgcaatatcagactt caacaagctcccggccgcaacgccagtgttcgccaggcggtcactttccg acagcgctctgcagcagcgagatggcccgcgcagcaagcagcaggtcacc ctggaagagctagcgcagcataatacgcctgaggattgctggctggtcat caagaacaaggtgtacgacgtcagcggttggggaccgcagcaccccggtg ggcacgtgatctatacgtatgctggcaaagacgccacggacgttttgcc tgatccatgcccagaccacttggtcgcagttgagacccttctgcatcggg gacattgtggaggaggagccaatgccggcgctgctcaaagacttccgcga gctgcgcacccggctgcagcagcagggcctgtttcgcagcaacaagagta
```

-continued
```
ctacagtacaaggtggccagcacgctgagcctactggcggccgcgctggc agtgctgatcacgcagcgcgactcctggctgggtctcgtcggcggcgcgt tcctgctgggcctcttaggcagcagtcgggctggctggcgcacgacttcc tgcaccaccaggtcttcaccgaccgccagtggaacaacgtgatgggctac ttcctgggcaacgtctgccagggatcagcacggactggtggaagagcaag cacaacgtgcaccacgcggtgcccaacgagctcgacagcgacagcaaggc ggcgcgggaccccgacatcgacacgctgcccctgctggcctggagctcgg agatgctggacagcatgagcaactcgggcgcgcgcctgtttgtgcgcatg cagcactacttcttcttccccatcctgctcttcgcgcgcatgtcctggtg ccagcagtctgtcgcgcacgcctcggacctgtccaggacctcaaaggcgg gcgtgtatgagctggcgtatcttgcgctgcattatgcctggttcctgggc gcggccttcagcgtgctcccgcccctcaaggcggtcgtgttcgcgctgct cagccagatgttttccggcttcctgctctccatcgtctttgtgcagagcc acaacggcatggaggtgtacagcgacacaaaggactttgtgacggcccag attgtgtccacgcgcgacatattgtcaaacgtctggaacgactggttcac aggcgggctgaactaccagatcgagcaccacctgttcccccacgctgccgc gccacaacctgggcaaggtccagaagtccatcatggagctgtgccacaag catgcctggtgtacgaaaactgcggcatggctactggcacctatcgtgt gctgcagcgcctggcaaacgtggcagctgaggcctag
```

In another embodiment. SEQ ID NO; 5 encodes the amino acid sequence of SEQ ID NO: 2.

In another embodiment, the isolated polynucleotide comprises a DNA sequence comprising the sequence:

```
                                    (SEQ ID NO: 6, PiDes5)
atgatggctgtaacagagggcgctgggggtgtaacggccgaggttggttt gcacaaacgcagttctcagccgcgtcccgcagctccccgcagcaagctgt tcacgttggatgaggttgcaaagcacgacagcccgactgactgctgggtg gtcattcggcggagggtttacgacgtgacgcgtgggtgccgcagcatcct ggcggaaacctgatctttgtgaaagctggccgcgactgtaccagctgtt cgattcctaccaccccttaagtgccagggctgtgctagacaagttctaca tcggtgaagtcgatgtaaggcctggggacgagcagttccttgtggctttc gaagaggacacagaggagggtcagttctacacggtcctcaagaagcgtgt ggagaagtacttcagggagaacaagctcaacccgcggcaacaggcgccat gtacgccaagtcgctgaccatcctggcgggcctggcgttgagcttctatg gtacgttctttgccttcagcagcgcaccggcctcgctgctcagcgctgtg ctgctcggcatttgcatggcggaggtgggcgtgtccatcatgcacgatgc caaccacggcgcatttgcccgcaacacgtgggcctcgcatgccctgggcg ccacgctggacatcgtgggggcatcctccttcatgtggcgccagcagcat gtcgtgggccaccatgcataccaacgtggacggtcaggacccagacct gcgagttaaggaccccgacgttcgccgcgtgaccaagttccagcccagc agtcgtaccaggcgtaccagcacatctacctggccttcctgtacggcctg
```

```
ctggccatcaagagcgtgctgctggacgactttatggccctcagctccgg cgccatcggctccgtgaaagtggccaagctgacgcccggcgagaagctcg tgttctggggcggcaaggcgctctggctcggctactttgtgctgctgccg gtggtgaagagccgccactcctggccgctgctggcggcctgctggctgct gagcgagtttgtcacgggctggatgctggccttcatgttccaggtggcgc acgtgaccagcgatgtgagctacctggaggctgacaagacaggcaaggtc ccgaggggctgggctgccgcacaggccgccaccaccgccgactttgcgca tggctcctggttctggacccaaatttctggcggccttaactaccaggtgg tgcaccatctgtcccgggcatctgccatctgcactaccggccatcgcc ccatcgtgctggacacctgcaaggagtttaacgtgccctaccatgtgtac cccacgtttgtcagggcactcgccgcacacttcaagcatctcaaggacat gggcgccccaactgccatcccttcgctggccaccgtgggatag
```

In another embodiment, SEQ ID NO: 6 encodes the amino acid sequence of SEQ ID NO: 3.

In another embodiment, the isolated polynucleotide comprises a DNA sequence that is at least 60% homologous to the nucleic acid sequence of SEQ ID NO: 4, SEQ ID NO: 5, SEQ ID NO: 6, or SEQ ID NO: 8. In another embodiment, the isolated polynucleotide comprises a DNA sequence that is at least 70% homologous to the nucleic acid sequence of SEQ ID NO: 4, SEQ ID NO: 5, SEQ ID NO: 6, or SEQ ID NO: 8. In another embodiment, the isolated polynucleotide comprises a DNA sequence that is at least 75% homologous to the nucleic acid sequence of SEQ ID NO: 4, SEQ ID NO: 5, SEQ ID NO: 6, or SEQ ID NO: 8. In another embodiment, the isolated polynucleotide comprises a DNA sequence that is at least 80% homologous to the nucleic acid sequence of SEQ ID NO: 4, SEQ ID NO: 5, SEQ ID NO: 6, or SEQ ID NO: 8. In another embodiment, the isolated polynucleotide comprises a DNA sequence that is at least 85% homologous to the nucleic acid sequence of SEQ ID NO: 4, SEQ ID NO: 5, SEQ ID NO: 6, or SEQ ID NO: 8. In another embodiment, the isolated polynucleotide comprises a DNA sequence that is at least 90% homologous to the nucleic acid sequence of SEQ ID NO: 4, SEQ ID NO: 5, SEQ ID NO: 6, or SEQ ID NO: 8. In another embodiment, the isolated polynucleotide comprises a DNA sequence that is at least 95% homologous to the nucleic acid sequence of SEQ ID NO: 4, SEQ ID NO: 5, SEQ ID NO: 6, or SEQ ID NO: 8. In another embodiment, the isolated polynucleotide comprises a DNA sequence that is at least 98% homologous to the nucleic acid sequence of SEQ ID NO: 4, SEQ ID NO: 5, SEQ ID NO: 6, or SEQ ID NO: 8.

In another embodiment, the isolated polynucleotide comprises a DNA sequence that is at least 60% identical to the nucleic acid sequence of SEQ ID NO: 4, SEQ ID NO: 5, SEQ ID NO: 6, or SEQ ID NO: 8. In another embodiment, the isolated polynucleotide comprises a DNA sequence that is at least 70% identical to the nucleic acid sequence of SEQ ID NO: 4, SEQ ID NO: 5, SEQ ID NO: 6, or SEQ ID NO: 8. In another embodiment, the isolated polynucleotide comprises a DNA sequence that is at least 75% identical to the nucleic acid sequence of SEQ ID NO: 4, SEQ ID NO: 5, SEQ ID NO: 6, or SEQ ID NO: 8. In another embodiment, the isolated polynucleotide comprises a DNA sequence that is at least 80% identical to the nucleic acid sequence of SEQ ID NO: 4, SEQ ID NO: 5, SEQ ID NO: 6, or SEQ ID NO: 8. In another embodiment, the isolated polynucleotide comprises a DNA sequence that is at least 85% identical to the nucleic acid sequence of SEQ ID NO: 4, SEQ ID NO: 5, SEQ ID NO: 6, or SEQ ID NO: 8. In another embodiment, the isolated polynucleotide comprises a DNA sequence that is at least 90% identical to the nucleic acid sequence of SEQ ID NO: 4, SEQ ID NO: 5, SEQ ID NO: 6, or SEQ ID NO: 8. In another embodiment, the isolated polynucleotide comprises a DNA sequence that is at least 95% identical to the nucleic acid sequence of SEQ ID NO: 4, SEQ ID NO: 5, SEQ ID NO: 6, or SEQ ID NO: 8. In another embodiment, the isolated polynucleotide comprises a DNA sequence that is at least 98% identical to the nucleic acid sequence of SEQ ID NO: 4, SEQ ID NO: 5, SEQ NO: 6, or SEQ ID NO: 8.

In another embodiment, the present invention comprises a desaturase or a nucleic acid molecule encoding the same combined with additional proteins and/or enzymes and/or substrates that are involved in the biosynthesis of VLC-PUFA. In another embodiment, the present invention comprises a composition comprising a desaturase or a nucleic acid molecule encoding the same combined with additional proteins and/or enzymes and/or substrates that are involved in the biosynthesis of VLC-PUFA. In another embodiment, the present invention comprises a transgenic plant comprising a desaturase or a nucleic acid molecule encoding the same combined with additional proteins and/or enzymes and/or substrates that are involved in the biosynthesis of VLC-PUFA. In another embodiment, the present invention comprises a transgenic alga comprising a desaturase or a nucleic acid molecule encoding the same combined with additional proteins and/or enzymes and/or substrates that are involved in the biosynthesis of VLC-PUFA. In another embodiment, the present invention comprises a transfected or a transformed cell comprising a desaturase or a nucleic acid molecule encoding the same combined with additional proteins and/or enzymes and/or substrates that are involved in the biosynthesis of VLC-PUFA.

In another embodiment, the present invention comprises a desaturase or a nucleic acid molecule encoding the same combined with additional proteins and/or enzymes and/or substrates that are involved in the biosynthesis of VLC-PUFA. In another embodiment, the present invention comprises an algal desaturase or a nucleic acid molecule encoding the same combined with additional algal proteins and/or enzymes and/or substrates that are involved in the biosynthesis of VLC-PUFA. In another embodiment, the present invention provides that the alga is a microalga. In another embodiment, the present invention comprises a microalgae desaturase or a nucleic acid molecule encoding the same combined with additional microalgae proteins and/or enzymes and/or substrates that are involved in the biosynthesis of VLC-PUFA.

In another embodiment, the present invention provides that algae proteins comprise an elongase. In another embodiment an elongase is described in PCT/IL2009/001117 which is hereby incorporated in its entirety by reference. In another embodiment, the present invention provides that microalgae proteins comprise the *P. incisa* PiELO1 gene product. In another embodiment, the present invention provides that elongase as described herein comprises the amino acid sequence:

(SEQ ID NO: 7)
MALTAAWHKYDAIVSRFVFDGLRRVGLQEIQGHPSVITAHLPFIASPTPQ

VTFVLAYLLIVVCGVAALRTRKSSAPREDPAWLRLLVQAHNLVLISLSAY

MSSAACYYAWKYGYRFWGTNYSPKERDMGGLIYTFYVSKLYEFVDTLIML

-continued
LKGKVEQVSFLHVYHHASISTIWWAIAYVAPGGDAWYCCFLNSLVHVLMY

TYYLLATLLGKDAKARRKYLWWGRYLTQFQMFQFVTMMLEAAYTWAYSPY

PKFLSKLLFFYMITLLALFANFYAQKHGSSRAAKQKLQ

In another embodiment, the elongase as described herein id encoded by a polynucleotide comprising a DNA sequence comprising the sequence:

(SEQ ID NO: 8)
atggcattgacggcggcctggcacaagtacgacgctatcgttagtcgctt tgttttcgatggcttgcgcagggttggcctgcaagagattcaaggccacc cctcggtgatcaccgcccaccttcccttcatagcctcccaacgccacaa gtgacgttcgtgctggcctatctgctgattgttgtctgcggggttgccgc tctgcgtacgagaaagtcgtccgcacctcgcgaggatccggcgtggctgc gactgcttgtgcaagcgcacaacttggtgctaatcagccttagcgcctac atgtcctctgccgcctgctactatgcttggaaatacggctataggttttg gggcacaaactatagccccaaggagcgggacatgggagggctcatctata cctttacgtgtccaagctgtacgagtttgtggatacgctgatcatgctg ctcaagggcaaggtggagcaggtttcttttttgcacgtctaccaccacgc ttccatatccacgatctggtgggcaatcgcatacgtcgcacctggtggtg acgcctggtactgctgcttcctgaactcgctggtccacgtactcatgtac acatactacctgcttgcgacgctgctgggaaaggacgccaaggcgcggcg caagtatttgtggtggggacgctacctcactcagttccagatgttccagt ttgtgacgatgatgctcgaggcagcgtacacttgggcctactctccctac cccaagttttttatcaaagctgctgttatttaCatgatcactctgttggcc ctgtttgcaaacttctatgcacagaagcatggcagcagccgggcagccaa gcaaaagctgcagtaa In another embodiment, the present invention provides a composition comprising a desaturase as described herein. In another embodiment, the present invention provides a composition comprising the desaturase as described herein and a VLC-PUFA elongase. In another embodiment, the present invention provides a composition comprising a protein as described herein. In another embodiment, the present invention provides a composition comprising the polynucleotide as described herein. In another embodiment, the present invention provides a composition comprising a polynucleotide encoding an elongase and the polynucleotide as described herein. In another embodiment, the present invention provides a composition comprising a vector comprising the polynucleotide as described herein. In another embodiment, the present invention provides a composition comprising a vector comprising a polynucleotide encoding an elongase and a polynucleotide as described herein. In another embodiment, the present invention provides a composition comprising a combination of vectors which comprise polynucleotides encoding an elongase and polynucleotides encoding desaturases. In another embodiment, a composition such as described herein comprises a carrier. In another embodiment, a carrier stabilizes a protein or a nucleic acid molecule of the invention. In another embodiment, one of skill in the art will readily identify a known suitable carrier to be used with the composition as described herein. In another embodiment, a carrier is a buffer such as but not limited to a phosphate buffer.

In another embodiment, one of skill in the art is able to prepare a composition comprising a desaturase as described herein. In another embodiment, one of skill in the art is able to prepare a composition comprising a combination of elongases and desaturases as described herein. In another embodiment, one of skill in the art is able to prepare a composition comprising a polynucleotide as described herein. In another embodiment, one of skill in the art is able to prepare a composition comprising a combination of polynucleotides, plasmids, vectors etc. as described herein. In another embodiment, the present invention provides a composition comprising the protein as described herein to be used in foodstuffs, dietary supplements or pharmaceutical compositions. In another embodiment, the present invention provides a composition comprising the protein as described herein to be used in industrial applications for the manufacturing of VLC-PUFAs. In another embodiment, the present invention provides a composition comprising the VLC-PUFAs, the products of the enzymes of the present invention. In another embodiment, a composition comprising VLC-PUFAs is used in foodstuffs, dietary supplements or pharmaceutical compositions.

In another embodiment, the invention includes a combination of Δ5, Δ6, and/or Δ12 desaturases. In another embodiment, the invention includes a composition comprising the combination of Δ5, Δ6, and/or Δ12 desaturases. In another embodiment, the invention includes a composition comprising the combination of Δ5, Δ6, and/or Δ12 desaturases and either ω3 or ω6 C18 substrates. In another embodiment, the invention provides that a composition comprising the combination of Δ5, Δ6, and/or Δ12 desaturases and either ω3 or ω6 C18 substrates yields DGLA, ARA, DHA and/or EPA.

In another embodiment, the invention provides conjunction of P. incisa Δ12, Δ6, and Δ5 desaturases, which are set of P. incisa genes involved in the biosynthesis of ARA. In another embodiment, the invention provides conjunction of P. incisa Δ12, Δ6, and Δ5 desaturase and Δ6 specific PUFA elongase (as described herein), which are set of P. incisa genes involved in the biosynthesis of DGLA, ARA, DHA, EPA, or any combination thereof.

In another embodiment, a desaturase as described herein comprises three histidine rich motifs (his-boxes). In another embodiment, Δ6 (PiDes6) and Δ5 (PiDes5) desaturases comprise fused cytochrome b5 at their N-terminus, supporting their microsomal localization. In another embodiment, Δ6 (PiDes6) and Δ5 (PiDes5) desaturases comprise a HPGG quartet along with four amino acids conserved in all cytochrome b5 fusion desaturases (FIG. 1).

In another embodiment, transforming a plant with an algal-derived gene such as described herein produces better results in comparison to fungal genes. In another embodiment, transforming a plant with an algal-derived gene such as described herein in combination with additional genes that encode proteins that are involved in the biosynthesis of VLC-PUFA produces better results in comparison to fungal or wild-type genes. In another embodiment, transforming a plant with an algal-derived gene such as described herein (desaturase) in combination with an elongase as described herein produces better results in comparison to fungal or wild-type genes. In another embodiment, transforming a plant with a combination of algal-derived genes such as described herein produces better results (such as ARA production) in comparison to fungal or wild-type genes. In another embodiment, transforming a plant with a combination of algal-derived desaturase genes such as described herein produces better results (such as ARA production) in comparison to fungal or wild-type genes. In another embodiment, P. incisa is the richest plant source of ARA. In another embodiment, P. incisa is the richest algal source of ARA. In another embodiment, algal-derived genes such as described herein are more effective alone or in combination than those of other sources.

In another embodiment, algae as described herein are eukaryotic organisms. In another embodiment, algae as described herein are photoautotrophic. In another embodiment, algae as described herein are mixotrophic. In another embodiment, algae as described herein are unicellular. In another embodiment, algae as described herein are multicellular. In another embodiment, algae as described herein are Excavata algae. In another embodiment, algae as described herein are Rhizaria algae. In another embodiment, algae as described herein are Chromista algae. In another embodiment, algae as described herein are Alveolata algae.

In another embodiment, an algal gene and protein of the present invention is superior when compared to its homologues with respect to efficient production of PUFAs. In another embodiment, transforming a first alga with an algal gene derived from a second alga such as described herein produces better results in comparison to fungal genes. In another embodiment, a second algal gene is a gene as described herein. In another embodiment, a first and a second algal are of different species. In another embodiment, transforming a first alga with an algal gene derived from a second alga such as described herein in combination with additional genes that encode proteins that are involved in the biosynthesis of VLC-PUFA produces better results in comparison to fungal or wild-type genes. In another embodiment, transforming an alga with an algal gene (such as desaturase) derived from a second alga such as described herein in combination with an elongase as described herein produces better results in comparison to fungal or wild-type genes. In another embodiment, transforming a first alga with a combination of algal genes derived from a second alga, a third alga, etc., such as described herein produces better results (such as ARA production) in comparison to fungal or wild-type genes. In another embodiment, transforming a first alga with a combination of algal desaturase genes derived from a second alga such as described herein produces better results (such as ARA production) in comparison to fungal or wild-type genes. In another embodiment, P. incisa is the second alga. In another embodiment, P. incisa is the source of choice for genes that are involved in the biosynthesis of VLC-PUFA. In another embodiment, P. incisa is the source of choice for genes that are involved in the biosynthesis of ARA, DHA, EPA, DGLA, or any combination thereof. In another embodiment, P. incisa-derived genes such as described herein are more effective alone or in combination than those of other sources.

In another embodiment, a DNA sequence as described herein such as but not limited to SEQ ID NO: 4-6 is used to engineer a transgenic organism. In another embodiment, DNA sequences as described herein such as but not limited to SEQ ID NO: 4-6 are used to engineer a transgenic organism or transform a cell. In another embodiment, DNA sequences as described herein such as but not limited to SEQ ID NO: 4-6 and 8 are used to engineer a transgenic organism or transform a cell. In another embodiment, the DNA sequences comprise the sequences provided in SEQ ID NO: 4-6 and 8 or variants of these sequences due, for example: base substitutions, deletions, and/or additions.

In another embodiment, the present invention provides transgenic plant oils enriched with VLC-PUFA. In another embodiment, the present invention provides transgenic alga oils enriched with VLC-PUFA. In another embodiment, the present invention provides the reconstitution of C20-VLC-PUFA biosynthesis in oil-synthesizing seeds of higher plants.

In another embodiment, the present invention provides expanded use by enhancement of the levels of ARA, DGLA, DHA, EPA, or a combination thereof in the transgenic plants.

In another embodiment, the present invention provides an expression vector comprising the polynucleotide as described herein. In another embodiment, the present invention provides a combination of expression vectors each comprising a polynucleotide as described herein. In another embodiment, the present invention provides an expression vector comprising a combination of polynucleotides as described herein. In another embodiment, the present invention provides a plant specific expression vector comprising the polynucleotide or combination of polynucleotides as described herein. In another embodiment, the present invention provides an algal specific expression vector comprising the polynucleotide or combination of polynucleotides as described herein. In another embodiment, the present invention provides a cell comprising the expression vector/s as described herein. In another embodiment, the expression vector/s is contained within an *agrobacterium*. In another embodiment, a cell is a plant cell or an algal cell. In another embodiment, a plant is an oil crop. In another embodiment, the transformed plant is an oil crop.

In another embodiment, the present invention provides a transgenic plant, a transgenic seed, or a transgenic alga transformed by a polynucleotide as described herein. In another embodiment, the present invention provides a transgenic plant, a transgenic seed, or a transgenic alga transformed by any combination of polynucleotides as described herein. In another embodiment, the present invention provides that the transgenic plant is a true-breeding for the polynucleotide/s as described herein. In another embodiment, the present invention provides a transgenic seed, produced by a transgenic plant transformed by the polynucleotide/s as described herein. In another embodiment, a transgenic plant, a transgenic seed, or a transgenic alga as described herein produces very long-chain polyunsaturated fatty acid (VLC-PUFA). In another embodiment, a transgenic plant, a transgenic seed, or a transgenic alga as described herein produces arachidonic acid. In another embodiment, a transgenic plant or a transgenic seed as described herein produces DHA. In another embodiment, a transgenic plant, a transgenic seed, or a transgenic alga as described herein produces DGLA.

In another embodiment, the present invention provides a method of producing very long-chain polyunsaturated fatty acid (VLC-PUFA) in a plant, a plant cell, or an alga comprising the step of transforming a plant, a plant cell, or an alga with a polynucleotide as described herein. In another embodiment, the present invention unexpectedly provides an utmost efficient method of producing very long-chain polyunsaturated fatty acid (VLC-PUFA) in a plant, a plant cell, or an alga comprising the step of transforming a plant, a plant cell, or an alga with a polynucleotide as described herein. In another embodiment, a VLC-PUFA is produced from .gamma.-linolenic acid (GLA).

In another embodiment, a VLC-PUFA is produced from stearidonic acid (SDA). In another embodiment, a VLC-PUFA is produced from GLA, SDA, or their combination. In another embodiment, a VLC-PUFA comprises 20 carbons. In another embodiment, a VLC-PUFA is $20:3\omega6$ or $20:4\omega3$. In another embodiment, a VLC-PUFA is produced by the protein/s as described herein in a cell or a plant, a plant cell, or an alga. In another embodiment, a VLC-PUFA is produced by the protein/s as described herein in a cell, a plant, a plant cell, or an alga under oleogenic conditions. In another embodiment, an unexpected amount of VLC-PUFA is produced by the protein/s as described herein in a cell, an alga, or a plant under nitrogen starvation conditions.

In another embodiment, a cell is a eukaryotic cell. In another embodiment, a cell is a prokaryotic cell. In another embodiment, a cell is a plant cell. In another embodiment, a cell is an algal cell. In another embodiment, a cell is a transfected cell. In another embodiment, a cell is transiently transfected with a polynucleotide or a combination of polynucleotides as described herein. In another embodiment, a cell is stably transfected with a polynucleotide or a combination of polynucleotides as described herein. In another embodiment, the present invention provides a method of enhancing oil storage, EPA accumulation, DHA accumulation, ARA accumulation, DGLA accumulation, or a combination thereof in a cell, comprising the step of transforming a cell with a polynucleotide as described herein. In another embodiment, the present invention provides a method of enhancing oil storage, EPA accumulation, DHA accumulation, ARA accumulation, DGLA accumulation, or a combination thereof in a cell, comprising the step of transfecting a cell with a polynucleotide as described herein. In another embodiment, the present invention provides a method of enhancing oil storage, EPA accumulation, DHA accumulation, DGLA accumulation, ARA accumulation, or a combination thereof in a cell, comprising the step of transforming a cell with a combination of polynucleotides as described herein. In another embodiment, the present invention provides a method of enhancing oil storage, EPA accumulation, DHA accumulation, ARA accumulation, DGLA accumulation, or a combination thereof in a cell or a multicellular organism, comprising the step of transforming a cell or a multicellular organism with a polynucleotide as described herein. In another embodiment, the present invention provides a method of enhancing oil storage, EPA accumulation, DGLA accumulation, DHA accumulation, ARA accumulation, or a combination thereof in a multicellular organism, comprising the step of transforming a multicellular organism with a combination of polynucleotides as described herein. In another embodiment, the multicellular organism or cell is grown under nitrogen starvation conditions, oleogenic conditions, or a combination thereof.

In another embodiment, transformation as used herein comprises "transduction". In another embodiment, transformation as used herein comprises transfection. In another embodiment, transformation as used herein comprises "conjugation". In another embodiment, transformation as used herein applies to eukaryotic and prokaryotic cells. In another embodiment, transformation as used herein comprises the insertion of new genetic material into nonbacterial cells including animal and plant cells.

In another embodiment, the present invention provides a method of enhancing oil storage, EPA accumulation, DHA accumulation, DGLA accumulation, ARA accumulation, or a combination thereof in a plant cell, comprising the step of transforming a plant cell with a polynucleotide as described herein. In another embodiment, the present invention provides a method of enhancing oil storage, EPA accumulation, DHA accumulation, ARA accumulation, DGLA accumulation, or a combination thereof in a plant cell, comprising the step of transforming a plant cell with a combination of polynucleotides as described herein. In another embodiment, the present invention provides a method of enhancing oil storage, EPA accumulation, DHA accumulation, ARA accumulation, DGLA accumulation, or a combination thereof in a plant, comprising the step of transforming a plant with a polynucleotide as described herein. In another embodiment, the present invention provides a method of enhancing oil storage, EPA accumulation, DHA accumulation, ARA accumulation, DGLA accumulation, or a combination thereof in a plant, comprising the step of transforming a plant with a combination of polynucleotides as described herein. In another embodiment, the plant or plant cell is grown under nitrogen starvation conditions, oleogenic conditions, or a combination thereof.

In another embodiment, the invention further provides an engineered organism, such as a transgenic plant. In another embodiment, the invention further provides an engineered organism, such as a transgenic seed. In another embodiment, the invention further provides an engineered organism, such as a transgenic alga. In another embodiment, the invention further provides an engineered organism, such as a transgenic animal. In another embodiment, an engineered organism is engineered to express a protein as described herein. In another embodiment, an engineered organism is engineered to express a combination of proteins as described herein. In another embodiment, an engineered organism is engineered to express elevated levels of the protein or a combination of proteins. In another embodiment, an engineered plant as described herein is used for manufacturing desired PUFAs such as but not limited to ARA. In another embodiment, an engineered plant as described herein is used for manufacturing desired PUFAs such as ARA at a reduced cost.

In another embodiment, an engineered organism comprises a synthetic pathway for the production of a protein. In another embodiment, an engineered organism comprising a synthetic pathway for the production of the protein allows greater control over the production of PUFAs by the pathway by an organism. In another embodiment, the pathway includes but is not limited to N-fatty acid desaturase, and/or N-fatty acid desaturase.

In another embodiment, an engineered cell, plant or seed comprises an oligonucleotide as described herein. In another embodiment, an engineered plant or seed produces a protein as described herein and comprises an oligonucleotide as described herein. In another embodiment, an engineered plant or seed produces proteins as described herein and comprises oligonucleotides as described herein.

In another embodiment, the invention provides a method of producing very long-chain polyunsaturated fatty acid (VLC-PUFA) in a cell, a plant, a plant cell, or an alga, comprising the step of transforming a plant, a plant cell, or an alga with a polynucleotide as described herein, thereby producing a VLC-PUFA in a plant, a plant cell, or an alga. In another embodiment, the invention provides a method of producing very long-chain polyunsaturated fatty acid (VLC-PUFA) in a cell, a plant, a plant cell, or an alga, comprising the step of transforming a plant, a plant cell, or an alga with an exogenous polynucleotide as described herein, thereby producing a VLC-PUFA in a cell, a plant, a plant cell, or an alga. In another embodiment, the invention provides a method of producing very long-chain polyunsaturated fatty acid (VLC-PUFA) in a cell, a plant, a plant cell, or an alga, comprising the step of transforming a plant, a plant cell, or an alga with a vector comprising an exogenous polynucleotide as described herein, thereby producing a VLC-PUFA in a cell; a plant, a plant cell, or an alga. In another embodiment, the invention provides a method of producing very long-chain polyunsaturated fatty acid (VLC-PUFA) in a cell, a plant, a plant cell, or an alga, comprising the step of transforming a plant, a plant cell, or an alga with a combination of vectors comprising a combination of exogenous polynucleotides as described herein, thereby producing a VLC-PUFA in a cell, a plant, a plant cell, or an alga. In another embodiment, the invention provides a method of producing very long-chain polyunsaturated fatty acid (VLC-PUFA) in a cell, a plant, a plant cell, or an alga, comprising the step of transforming a cell, a plant, a plant cell, or an alga with a combination of exogenous polynucleotides as described herein, thereby producing a VLC-PUFA in a cell, a plant, a plant cell, or an alga.

In another embodiment, the invention provides that a plant, a cell, a plant cell, or an alga as described herein is treated or supplemented with linoleic acid (LA; 18:2ω6), α-linolenic acid (ALA; 18:3ω3), oleic acid (18:1), dihomo-gamma-linolenic acid (20:3ω6), phosphatidylcholine (PC), diacylglyceroltrimethylhomoserine (DGTS), phosphatidylethanolamine (PE), or any combination thereof, before transformation, after transformation, during transformation or a combination thereof.

In another embodiment, the invention provides that the VLC-PUFA is eicosapentaenoic acid (EPA, 20:5ω3). In another embodiment, the invention provides that the VLC-PUFA is docosahexaenoic acid (DHA, 22:6ω3). In another embodiment, the invention provides that the VLC-PUFA is arachidonic acid (ARA, 20:4ω6). In another embodiment, the invention provides that a cell, a plant, or an alga transformed by a polynucleotide or a combination of polynucleotides as described herein, is grown under oleogenic conditions. In another embodiment, the invention provides that a cell, a plant, or an alga transformed by a polynucleotide or a combination of polynucleotides as described herein, is grown under nitrogen starvation conditions.

In another embodiment, the invention provides that producing very long-chain polyunsaturated fatty acid (VLC-PUFA) is enhancing oil storage, arachidonic acid accumulation, eicosapentaenoic acid accumulation, docosahexaenoic acid accumulation, or a combination thereof that a cell, a plant, or an alga transformed by a polynucleotide or a combination of polynucleotides as described herein In another embodiment, a PUFA is di-homo-gamma-linolenic acid, arachidonic acid, eicosapentaenoic acid, docosatrienoic acid, docosatetraenoic acid, docosapentaenoic acid or docosahexaenoic acid. In another embodiment, a PUFA is a 24 carbon fatty acid with at least 4 double bonds.

In another embodiment, expression of the protein/s of the invention in plants or seed requires subcloning an ORF/s sequence encoding the protein/s into a plant expression vector, which may comprise a viral 35S promoter, and a Nos terminator. In another embodiment, a cassette or promoter/coding sequence/terminator is then be subcloned into the plant binary transformation vector, and the resulting plasmid introduced into *Agrobacterium*. In another embodiment, the *Agrobacterium* strain transforms the plant. In another embodiment, the. *Agrobacterium* strain transforms the plant by the vacuum-infiltration of inflorescences, and the seeds harvested and plated onto selective media containing an antibiotic. In another embodiment, the plasmid confers resistance to an antibiotic, thus only transformed plant material will grow in the presence of an antibiotic. In another embodiment, resistant lines are identified and self-fertilized to produce homozygous material. In another embodiment, leaf material is analyzed for expression of the protein comprising desaturase activity. In another embodiment, leaf material is analyzed for expression of a combination of protein comprising desaturase and elongase activities.

In some embodiments, the terms "protein", "desaturase", or "polypeptide" are used interchangeably. In some embodiments, "protein", "desaturase", or "polypeptide" as used herein encompasses native polypeptides (either degradation products, synthetically synthesized polypeptides or recombinant polypeptides) and peptidomimetics (typically, synthetically synthesized polypeptides), as well as peptoids and semipeptoids which are polypeptide analogs, which have, in some embodiments, modifications rendering the polypeptides/proteins even more stable while in a body or more capable of penetrating into cells.

In some embodiments, modifications include, but are not limited to N terminus modification, C terminus modification, polypeptide bond modification, including, but not limited to, CH2-NH, CH2-S, CH2-S=O, O=C—NH, CH2-O, CH2-CH2, S=C—NH, CH=CH or CF=CH, backbone modifications, and residue modification. Methods for preparing peptidomimetic compounds are well known in the art and are specified, for example, in Quantitative Drug Design, C. A. Ramsden Gd., Chapter 17.2, F. Choplin Pergamon Press (1992), which is incorporated by reference as if fully set forth herein. Further details in this respect are provided hereinunder.

In some embodiments, polypeptide bonds (—CO—NH—) within the polypeptide are substituted. In some embodiments, the polypeptide bonds are substituted by N-methylated bonds (—N(CH$_3$)—CO—). In some embodiments, the polypeptide bonds are substituted by ester bonds (—C(R)H—C—O—O—C(R)—N—). In some embodiments, the polypeptide bonds are substituted by ketomethylene bonds (—CO—CH$_2$—). In some embodiments, the polypeptide bonds are substituted by α-aza bonds (—NH—N(R)—CO—), wherein R is any alkyl, e.g., methyl, carbo bonds (—CH$_2$—NH—). In some embodiments, the polypeptide bonds are substituted by hydroxyethylene bonds (—CH(OH)—CH$_2$—). In some embodiments, the polypeptide bonds are substituted by thioamide bonds (—CS—NH—). In some embodiments, the polypeptide bonds are substituted by olefinic double bonds (—CH=CH—). In some embodiments, the polypeptide bonds are substituted by retro amide bonds (—NH—CO—). In some embodiments, the polypeptide bonds are substituted by polypeptide derivatives (—N(R)—CH$_2$—CO—), wherein R is the "normal" side chain, naturally presented on the carbon atom. In some embodiments, these modifications occur at any of the bonds along the polypeptide chain and even at several (2-3 bonds) at the same time.

In some embodiments, natural aromatic amino acids of the polypeptide such as Trp, Tyr and Phe, be substituted for synthetic non-natural acid such as Phenylglycine, TIC, naphthylelanine (Nol), ring-methylated derivatives of Phe, halogenated derivatives of Phe or o-methyl-Tyr. In some embodiments, the polypeptides of the present invention include one or more modified amino acid or one or more non-amino acid monomers (e.g., fatty acid, complex carbohydrates, etc.).

In one embodiment, "amino acid" or "amino acids" is understood to include the 20 naturally occurring amino acid; those amino acid often modified post-translationally in vivo, including, for example, hydroxyproline, phosphoserine and phosphothreonine; and other unusual amino acid including, but not limited to, 2-aminoadipic acid, hydroxylysine, isodesmosine, nor-valine, nor-leucine and ornithine. In one embodiment, "amino acid" includes both D- and L-amino acid.

In some embodiments, the polypeptides or proteins of the present invention are utilized in a soluble form. In some embodiments, the polypeptides or proteins of the present invention include one or more non-natural or natural polar amino acid, including but not limited to serine and threonine which are capable of increasing polypeptide or protein solubility due to their hydroxyl-containing side chain.

In some embodiments, the polypeptides or proteins of the present invention are utilized in a linear form, although it will be appreciated by one skilled in the art that in cases where cyclization does not severely interfere with polypeptide characteristics, cyclic forms of the polypeptide can also be utilized.

In some embodiments, the polypeptides or proteins of present invention are biochemically synthesized such as by using standard solid phase techniques. In some embodiments, these biochemical methods include exclusive solid phase synthesis, partial solid phase synthesis, fragment condensation, or classical solution synthesis. In some embodiments, these methods are used when the polypeptide is relatively short (about 5-15 kDa) and/or when it cannot be produced by recombinant techniques (i.e., not encoded by a nucleic acid sequence) and therefore involves different chemistry.

In some embodiments, solid phase polypeptide or protein synthesis procedures are well known to one skilled in the art and further described by John Morrow Stewart and Janis Dillaha Young, Solid Phase Polypeptide Syntheses (2nd Ed., Pierce Chemical Company, 1984). In some embodiments, synthetic polypeptides or proteins are purified by preparative high performance liquid chromatography [Creighton T. (1983) Proteins, structures and molecular principles. WH Freeman and Co. N.Y.], and the composition of which can be confirmed via amino acid sequencing by methods known to one skilled in the art.

In some embodiments, recombinant protein techniques are used to generate the polypeptides of the present invention. In some embodiments, recombinant protein techniques are used for generation of relatively long polypeptides (e.g., longer than 18-25 amino acid). In some embodiments, recombinant protein techniques are used for the generation of large amounts of the polypeptide of the present invention. In some embodiments, recombinant techniques are described by Bitter et al., (1987) Methods in Enzymol. 153:516-544, Studier et al. (1990) Methods in Enzymol. 185:60-89, Brisson et al. (1984) Nature 310:511-514, Takamatsu et al. (1987) EMBO J. 6:307-311, Coruzzi et al. (1984) EMBO J. 3:1671-1680 and Brogli et al, (1984) Science 224:838-843, Gurley et al. (1986) Mol. Cell. Biol. 6:559-565 and Weissbach & Weissbach, 1988, Methods for Plant Molecular Biology, Academic Press, NY, Section VIII, pp 421-463.

In one embodiment, a polypeptide or protein of the present invention is synthesized using a polynucleotide encoding a polypeptide or protein of the present invention. In some embodiments, the polynucleotide encoding a polypeptide of the present invention is ligated into an expression vector, comprising a transcriptional control of a cis-regulatory sequence (e.g., promoter sequence). In some embodiments, the cis-regulatory sequence is suitable for directing constitutive expression of the polypeptide of the present invention. In some embodiments, the cis-regulatory sequence is suitable for directing tissue specific expression of the polypeptide of the present invention. In some embodiments, the cis-regulatory sequence is suitable for directing inducible expression of the polypeptide of the present invention. In another embodiment, a polypeptide is a protein comprising a desaturase as described herein.

In another embodiment, the polynucleotide comprises a genomic polynucleotide sequence. In another embodiment, the polynucleotide comprises a composite polynucleotide sequence.

In one embodiment, the phrase "a polynucleotide" refers to a single or double stranded nucleic acid sequence which be isolated and provided in the form of an RNA sequence, a complementary polynucleotide sequence (cDNA), a genomic polynucleotide sequence and/or a composite polynucleotide sequences (e.g., a combination of the above).

In one embodiment, "genomic polynucleotide sequence" refers to a sequence derived (isolated) from a chromosome and thus it represents a contiguous portion of a chromosome.

In one embodiment, "composite polynucleotide sequence" refers to a sequence, which is at least partially complementary and at least partially genomic. In one embodiment, a composite sequence can include some exonal sequences required to encode the polypeptide of the present invention, as well as some intronic sequences interposing there between. In one embodiment, the intronic sequences can be of any source, including of other genes, and typically will include conserved splicing signal sequences. In one embodiment, intronic sequences include cis acting expression regulatory elements.

In one embodiment, the polynucleotides of the present invention further comprise a signal sequence encoding a signal peptide for the secretion of the polypeptides of the present invention. In one embodiment, following expression, the signal peptides are cleaved from the precursor proteins resulting in the mature proteins.

In some embodiments, polynucleotides of the present invention are prepared using PCR techniques or any other method or procedure known to one skilled in the art. In some embodiments, the procedure involves the legation of two different DNA sequences (See, for example, "Current Protocols in Molecular Biology", eds. Ausubel et al., John Wiley & Sons, 1992).

In one embodiment, polynucleotides of the present invention are inserted into expression vectors (i.e., a nucleic acid construct) to enable expression of the recombinant polypeptide. In one embodiment, the expression vector of the present invention includes additional sequences which render this vector suitable for replication and integration in prokaryotes. In one embodiment, the expression vector of the present invention includes additional sequences which render this vector suitable for replication and integration in eukaryotes. In one embodiment, the expression vector of the present invention includes a shuttle vector which renders this vector suitable for replication and integration in both prokaryotes and eukaryotes. In some embodiments, cloning vectors comprise transcription and translation initiation sequences (e.g., promoters, enhancers) and transcription and translation terminators (e.g., polyadenylation signals).

In one embodiment, a variety of prokaryotic or eukaryotic cells can be used as host-expression systems to express the polypeptides of the present invention. In some embodiments, these include, but are not limited to, microorganisms, such as bacteria transformed with a recombinant bacteriophage DNA, plasmid DNA or cosmid DNA expression vector containing the polypeptide coding sequence; yeast transformed with recombinant yeast expression vectors containing the polypeptide coding sequence; plant cell systems infected with recombinant virus expression vectors (e.g., cauliflower mosaic virus, CaMV; tobacco mosaic virus, TMV) or transformed with recombinant plasmid expression vectors, such as Ti plasmid, containing the polypeptide coding sequence.

In some embodiments, non-bacterial expression systems are used (e.g., plant expression systems) to express the polypeptide of the present invention.

In one embodiment, yeast expression systems are used. In one embodiment, algae expression systems are used. In one embodiment, plant expression systems are used. In one embodiment, a number of vectors containing constitutive or inducible promoters can be used in yeast as disclosed in U.S. Pat. No. 5,932,447 which is hereby incorporated in its entirety by reference. In another embodiment, vectors which promote integration of foreign DNA sequences into the yeast chromosome are used.

In another embodiment, expression in a host cell can be accomplished in a transient or a stable fashion. In another embodiment, a host cell is a cell as described herein. In another embodiment, transient expression is from introduced constructs which contain expression signals functional in the host cell, but which constructs do not replicate and rarely integrate in the host cell, or where the host cell is not proliferating. In another embodiment, transient expression also can be accomplished by inducing the activity of a regulatable promoter operably linked to the gene of interest.

In another embodiment, stable expression is achieved by introduction of a construct that integrates into the host genome. In another embodiment, stable expression comprises autonomously replication within the host cell. In another embodiment, stable expression of the polynucleotide of the invention is selected for through the use of a selectable marker located on or transfected with the expression construct, followed by selection for cells expressing the marker. In another embodiment, stable expression results from integration, the site of the construct's integration can occur randomly within the host genome or can be targeted through the use constructs containing regions of homology with the host genome sufficient to target recombination with the host locus. In another embodiment, constructs are targeted to an endogenous locus, all or some of the transcriptional and translational regulatory regions can be provided by the endogenous locus.

In another embodiment, an expression of a protein as described herein comprising desaturase activity includes functional transcriptional and translational initiation and termination regions that are operably, linked to the DNA encoding the protein comprising a desaturase activity. In another embodiment, an expression of proteins as described herein comprising various desaturase activities includes functional transcriptional and translational initiation and termination regions that are operably linked to the DNA encoding the proteins comprising desaturase activity. In another embodiment, an expression of proteins as described herein comprising desaturase and elongase activities includes functional transcriptional and translational initiation and termination regions that are operably linked to the DNA encoding each protein comprising a desaturase or elongase activity. In another embodiment, transcriptional and translational initiation and termination regions are derived from a variety of nonexclusive sources, including the DNA to be expressed, genes known or suspected to be capable of expression in the desired system, expression vectors, chemical synthesis, or from an endogenous locus in a host cell. In another embodiment, expression in a plant tissue and/or plant part presents certain efficiencies, particularly where the tissue or part is one which is harvested early, such as seed, leaves, fruits, flowers, roots, etc. In another embodiment, expression can be targeted to that location in a plant by utilizing specific regulatory sequences that are known to one of skill in the art. In another embodiment, the expressed protein is an enzyme which produces a product which may be incorporated, either directly or upon further modifications, into a fluid fraction from the host plant. In another embodiment, expression of a protein of the invention, or antisense thereof, alters the levels of specific PUFAs, or derivatives thereof, found in plant parts and/or plant tissues. The desaturase coding region, in some embodiments, may be expressed either by itself or with other genes such as but not limited to elongase, in order to produce cells, tissues, algae, and/or plant parts containing higher proportions of desired PUFAs or in which the PUFA composition more closely resembles that of human breast milk. In another embodiment, the termination region is derived from the 3' region of the gene from which the initiation region was obtained or from a different gene. In another embodiment, the termination region usually is selected as a matter of convenience rather than because of any particular property.

In another embodiment, a plant or plant tissue is utilized as a host or host cell, respectively, for expression of the protein of the invention which may, in turn, be utilized in the production of polyunsaturated fatty acids. In another embodiment, desired PUFAS are expressed in seed. In another embodiment, methods of isolating seed oils are known in the art. In another embodiment, seed oil components are manipulated through the expression of the protein of the invention in order to provide seed oils that can be added to nutritional compositions, pharmaceutical compositions, animal feeds and cosmetics. In another embodiment, a vector which comprises a DNA sequence encoding the protein as described herein is linked to a promoter, and is introduced into the plant tissue or plant for a time and under conditions sufficient for expression of the protein.

In another embodiment, a vector as described herein comprises additional genes that encode other enzymes, for example, elongase, Δ4-desaturase, a different Δ5-desaturase, a different Δ6-desaturase, Δ10-desaturase, a different Δ12-desaturase, Δ15-desaturase, Δ17-desaturase, Δ19-desaturase, or any combination thereof. In another embodiment, the plant tissue or plant produces the relevant substrate upon which the enzymes act or a vector encoding enzymes which produce such substrates may be introduced into the plant tissue, plant cell or plant. In another embodiment, a substrate is sprayed on plant tissues expressing the appropriate enzymes. In another embodiment, the invention is directed to a transgenic plant comprising the above-described vector, wherein expression of the nucleotide sequence of the vector results in production of a polyunsaturated fatty acid in, for example, the seeds of the transgenic plant.

In another embodiment, the regeneration, development, and cultivation of plants from single plant protoplast transformants or from various transformed explants is well known in the art (for example: Weissbach and Weissbach, In: Methods for Plant Molecular Biology, (Eds.), Academic Press, Inc. San Diego, Calif., (1988)). In another embodiment, regeneration and growth process comprises the steps of selection of transformed cells, culturing those individualized cells through the usual stages of embryonic development through the rooted plantlet stage. In another embodiment, transgenic embryos and seeds are similarly regenerated. In another embodiment, resulting transgenic rooted shoots are thereafter planted in an appropriate plant growth medium such as soil. In another embodiment, regeneration and growth process of algae are known to one of skill in the art. In another embodiment, identification, selection, of transgenic algae are known to one of skill in the art.

In another embodiment, development or regeneration of plants containing an exogenous polynucleotide as described herein encodes a protein as described herein and is well known in the art. In another embodiment, development or regeneration of algae containing an exogenous polynucleotide as described herein encodes a protein as described herein and is well known in the art. In another embodiment, the regenerated plants are self-pollinated to provide homozygous transgenic plants. In another embodiment, pollen obtained from the regenerated plants is crossed to seed-grown plants of agronomically important lines. In another embodiment, pollen from plants of these important lines is used to pollinate regenerated plants. In another embodiment, a transgenic plant of the present invention containing a desired polypeptide is cultivated using methods well known to one skilled in the art.

In another embodiment, a variety of methods can be utilized for the regeneration of plants from plant tissue. In another embodiment, the method of regeneration will depend on the starting plant tissue and the particular plant species to be regenerated. In another embodiment, methods for transforming dicots, primarily by use of Agrobacterium tumefaciens, and obtaining transgenic plants are known in the art McCabe et al., Biol. Technology 6:923 (1988), Christou et al., Plant Physiol. 87:671-674 (1988)); Cheng et al., Plant Cell Rep. 15:653657 (1996), McKently et al., Plant Cell Rep. 14:699-703 (1995)); Grant et al., Plant Cell Rep. 15:254-258, (1995).

In another embodiment, transformation of monocotyledons using electroporation, particle bombardment, and Agrobacterium are known. In another embodiment, transformation and plant regeneration are well established in the art. In another embodiment, assays for gene expression based on the transient expression of cloned nucleic acid constructs have been developed by introducing the nucleic acid molecules into plant cells by polyethylene glycol treatment, electroporation, or particle bombardment (Marcotte et al., Nature 335: 454-457 (1988); Marcotte et al., Plant Cell 1:523-532 (1989); McCarty et al., Cell 66:895-905 (1991); Hattori et al., Genes Dev. 6:609-618 (1992); Goff et al., EMBO J. 9:2517-2522 (1990)).

In another embodiment, transient expression systems are used to functionally dissect the oligonucleotides constructs. In another embodiment, practitioners are familiar with the standard resource materials which describe specific conditions and procedures for the construction, manipulation and isolation of macromolecules (e.g., DNA molecules, plasmids, etc.), generation of recombinant organisms and the screening and isolating of clones, (see for example: Sambrook et al., Molecular Cloning: A Laboratory Manual, Cold Spring Harbor Press (1989); Maliga et al., Methods in Plant Molecular Biology, Cold Spring Harbor Press (1995); Birren et al., Genome Analysis: Detecting Genes, 1, Cold Spring Harbor, N.Y. (1998); Birren et al., Genome Analysis: Analyzing DNA, 2, Cold Spring Harbor, N.Y. (1998); Plant Molecular Biology: A Laboratory Manual, eds. Clark, Springer, N.Y. (1997)).

In one embodiment, the expression vector of the present invention can further include additional polynucleotide sequences that allow, for example, the translation of several proteins from a single mRNA such as an internal ribosome entry site (IBES) and sequences for genomic integration of the promoter-chimeric polypeptide.

In some embodiments, expression vectors containing regulatory elements from eukaryotic viruses such as retroviruses are used by the present invention. In some embodiments, recombinant viral vectors are useful for in vivo expression of the polypeptides of the present invention since they offer advantages such as lateral infection and targeting specificity. In one embodiment, lateral infection is inherent in the life cycle of, for example, retrovirus, and is the process by which a single infected cell produces many progeny virions that bud off and infect neighboring cells. In one embodiment, the result is that a large area becomes rapidly infected, most of which was not initially infected by the original viral particles. In one embodiment, viral vectors are produced that are unable to spread laterally. In one embodiment, this characteristic can be useful if the desired purpose is to introduce a specified gene into only a localized number of targeted cells.

In one embodiment, various methods can be used to introduce the expression vector of the present invention into cells. Such methods are generally described in Sambrook et al., Molecular Cloning: A Laboratory Manual, Cold Springs Harbor Laboratory, New York (1989, 1992), in Ausubel et al., Current Protocols in Molecular Biology, John Wiley and Sons, Baltimore, Md. (1989), Chang et al., Somatic Gene Therapy, CRC Press, Ann Arbor, Mich. (1995), Vega et al., Gene Targeting, CRC Press, Ann Arbor Mich. (1995), Vectors: A Survey of Molecular Cloning Vectors and Their Uses, Butterworths, Boston Mass. (1988) and Gilboa et al. [Biotechniques 4 (6): 504-512, 1986] and include, for example, stable or transient transfection, lipofection, electroporation and infection with recombinant viral vectors. In addition, see U.S. Pat. Nos. 5,464,764 and 5,487,992 for positive-negative selection methods.

In one embodiment, plant expression vectors are used. In one embodiment, the expression of a polypeptide coding sequence is driven by a number of promoters. In some embodiments, viral promoters such as the 35S RNA and 19S RNA promoters of CaMV [Brisson et al., Nature 310:511-514 (1984)], or the coat protein promoter to TMV [Takamatsu et al., EMBO J. 6:307-311 (1987)] are used. In another embodiment, plant promoters are used such as, for example, the small subunit of RUBISCO [Coruzzi et al., EMBO J. 3:1671-1680 (1984); and Brogli et al., Science 224:838-843 (1984)] or heat shock promoters, e.g., soybean hsp17.5-E or hsp17.3-B [Gurley et al., Mol. Cell. Biol. 6:559-565 (1986)]. In one embodiment, constructs are introduced into plant cells using Ti plasmid, Ri plasmid, plant viral vectors, direct DNA transformation, microinjection, electroporation and other techniques well known to the skilled artisan. See, for example, Weissbach & Weissbach [Methods for Plant Molecular Biology, Academic Press, NY, Section VIII, pp 421-463(1988)]. Other expression systems such as insects and mammalian host cell systems, which are well known in the art, can also be used by the present invention.

It will be appreciated that other than containing the necessary elements for the transcription and translation of the inserted coding sequence (encoding the polypeptide or protein), the expression construct of the present invention can also include sequences engineered to optimize stability, production, purification, yield or activity of the expressed polypeptide or protein.

In some embodiments, transformed cells are cultured under effective conditions, which allow for the expression of high amounts of recombinant polypeptide or protein. In some embodiments, effective culture conditions include, but are not limited to, effective media, bioreactor, temperature, pH and oxygen conditions that permit protein production. In one embodiment, an effective medium refers to any medium in which a cell is cultured to produce the recombinant polypeptide or protein of the present invention. In some embodiments, a medium typically includes an aqueous solution having assimilable carbon, nitrogen and phosphate sources, and appropriate salts, minerals, metals and other nutrients, such as vitamins. In some embodiments, cells of the present invention can be cultured in conventional fermentation bioreactors, shake flasks, test tubes, microtiter dishes and petri plates. In some embodiments, culturing is carried out at a temperature, pH and oxygen content appropriate for a recombinant cell. In some embodiments, culturing conditions are within the expertise of one of ordinary skill in the art.

In some embodiments, depending on the vector and host system used for production, resultant polypeptides or proteins of the present invention either remain within the recombinant cell, secreted into the fermentation medium, secreted into a space between two cellular membranes, or retained on the outer surface of a cell or viral membrane.

In one embodiment, following a predetermined time in culture, recovery of the recombinant polypeptide or protein is effected.

In one embodiment, the phrase "recovering the recombinant polypeptide or protein" used herein refers to collecting the whole fermentation medium containing the polypeptide or protein and need not imply additional steps of separation or purification.

In one embodiment, polypeptides or proteins of the present invention are purified using a variety of standard protein purification techniques, such as, but not limited to, affinity chromatography, ion exchange chromatography, filtration, electrophoresis, hydrophobic interaction chromatography, gel filtration chromatography, reverse phase chromatography, concanavalin A chromatography, chromatofocusing and differential solubilization.

In one embodiment, to facilitate recovery, the expressed coding sequence can be engineered to encode the polypeptide or proteins of the present invention and fused cleavable moiety. In one embodiment, a fusion protein can be designed so that the polypeptide or protein can be readily isolated by affinity chromatography; e.g., by immobilization on a column specific for the cleavable moiety. In one embodiment, a cleavage site is engineered between the polypeptide or protein and the cleavable moiety and the polypeptide or protein can be released from the chromatographic column by treatment with an appropriate enzyme or agent that specifically cleaves the fusion protein at this site [e.g., see Booth et al., Immunol. Lett. 19:65-70 (1988); and Gardella et al., J. Biol. Chem. 265:15854-15859 (1990)].

In one embodiment, the polypeptide or protein of the present invention is retrieved in "substantially pure" form.

In one embodiment, the phrase "substantially pure" refers to a purity that allows for the effective use of the protein in the applications described herein.

In one embodiment, the polypeptide or protein of the present invention can also be synthesized using in vitro expression systems. In one embodiment, in vitro synthesis methods are well known in the art and the components of the system are commercially available.

In another embodiment, the invention comprises a process for making a very long-chain polyunsaturated fatty acid produced by the protein or combination of proteins of the invention in a cell as described herein. In another embodiment, the resulting very long-chain polyunsaturated fatty acid produced by the transgenic cell or organism as described herein is utilized as a food additive. In another embodiment, a very long-chain polyunsaturated fatty acid produced by the transgenic cell or organism as described herein is utilized as a supplement. In another embodiment, a very long-chain polyunsaturated fatty acid produced by the transgenic cell or organism as described herein is administered to a human subject. In another embodiment, a very long-chain polyunsaturated fatty acid produced by the transgenic cell or organism as described herein is administered to a baby. In another embodiment, a very long-chain polyunsaturated fatty acid produced by the transgenic cell or organism as described herein is administered to an infant. In another embodiment, a very long-chain polyunsaturated fatty acid produced by the transgenic cell or organism as described herein is administered to an animal. In another embodiment, a very long-chain polyunsaturated fatty acid produced by the transgenic cell or organism as described herein is administered to a mammal. In another embodiment, a very long-chain polyunsaturated fatty acid produced by the transgenic cell or organism as described herein is administered to a farm animal, a rodent, a pet, or a lab animal.

In another embodiment, the described pharmaceutical and nutritional compositions are utilized in connection with animals (i.e., domestic or non-domestic), as well as humans, as animals experience many of the same needs and conditions as humans. For example, the oil or acids of the present invention may be utilized in animal or aquaculture feed supplements, animal feed substitutes, animal vitamins or in animal topical ointments.

In another embodiment, a very long-chain polyunsaturated fatty acid produced by a protein or a combination of proteins of the invention is utilized in an infant formula. In another embodiment, a very long-chain polyunsaturated fatty acid produced by a protein or a combination of proteins of the invention is administered to a subject having a deficiency in very long-chain polyunsaturated fatty acid. In another embodiment, a very long-chain polyunsaturated fatty acid is a polyunsaturated C20 fatty acid.

In another embodiment, the isolated protein comprising desaturase activity is used indirectly or directly in the production of polyunsaturated fatty acids. In another embodiment, the isolated protein or a combination of isolated proteins comprising desaturase and/or desaturase/elongase activities are used indirectly or directly in the production of polyunsaturated fatty acids. In another embodiment, "Directly" is meant to encompass the situation where the enzyme directly desaturates the acid. In another embodiment, the latter of which is utilized in a composition. In another embodiment, "Indirectly" is meant to encompass the situation where an acid is converted to another acid (i.e., a pathway intermediate) by the enzyme and then the latter acid is converted to another acid by use of a non-desaturase enzyme. In another embodiment, a very long-chain polyunsaturated fatty acid produced either directly or indirectly is added to a nutritional composition, pharmaceutical compositions, cosmetics, and animal feeds, all of which are encompassed by the present invention.

In another embodiment, nutritional compositions include any food or preparation for human or animal consumption including for enteral or parenteral consumption, which when taken into the body (a) serve to nourish or build up tissues or supply energy and/or (b) maintain, restore or support adequate nutritional status or metabolic functions. In another embodiment, the nutritional composition of the present invention comprises at least one oil or acid produced directly or indirectly by use of the protein of the invention and may either be in a solid or liquid form. In another embodiment, the composition includes edible macronutrients, vitamins and minerals in amounts desired for a particular use. In another embodiment, the amount of such ingredients will vary depending on whether the composition is intended for use with normal, healthy infants, children or adults having specialized needs such as those which accompany certain metabolic conditions (e.g., metabolic disorders).

In another embodiment, the macronutrients include edible fats, carbohydrates and proteins. In another embodiment, edible fats include but are not limited to coconut oil, soy oil, and mono- and diglycerides. In another embodiment, carbohydrates include but are not limited to glucose, edible lactose and hydrolyzed search. In another embodiment, proteins which are utilized in the nutritional composition of the invention include but are not limited to soy proteins, electrodialysed whey, electrodialysed skim milk, milk whey, or the hydrolysates of these proteins.

In another embodiment, vitamins and minerals are added to the nutritional compositions of the present invention and include but are not limited to: calcium, phosphorus, potassium, sodium, chloride, magnesium, manganese, iron, copper, zinc, selenium, iodine, and Vitamins A, E, D, C, and the B complex. Other such vitamins and minerals may also be added.

In another embodiment, components utilized in the nutritional compositions of the present invention will be of semi-purified or purified origin. By semi-purified or purified is meant a material which has been prepared by purification of a natural material or by synthesis. In another embodiment, nutritional compositions of the present invention include but are not limited to infant formulas, dietary supplements, dietary substitutes, and rehydration compositions. In another embodiment, a nutritional composition of the present invention may also be added to food even when supplementation of the diet is not required. In another embodiment, a composition is added to food of any type including but not limited to margarines, modified butters, cheeses, milk, yogurt, chocolate, candy, snacks, salad oils, cooking oils, cooking fats, meats, fish and beverages.

In another embodiment, a nutritional composition is an enteral nutritional product. In another embodiment, a nutritional composition is an adult or pediatric enteral nutritional product. In another embodiment, a composition is administered to adults or children experiencing stress or having specialized needs due to chronic or acute disease states. In another embodiment, a composition comprises, in addition to polyunsaturated fatty acids produced in accordance with the present invention, macronutrients, vitamins and minerals as described above. In another embodiment, the macronutrients may be present in amounts equivalent to those present in human milk or on an energy basis, i.e., on a per calorie basis.

In another embodiment, the present invention includes an enteral formula comprising polyunsaturated fatty acids produced in accordance with the present invention. In another embodiment, an enteral formula is sterilized and subsequently utilized on a ready-to-feed basis or stored in a concentrated liquid or powder. In another embodiment, a powder is prepared by spray drying the formula prepared as indicated above, and reconstituting it by rehydrating the concentrate. In another embodiment, the present invention includes an adult and pediatric nutritional formulas. In another embodiment, adult and pediatric nutritional formulas are known in the art and are commercially available (e.g., Similac®, Ensure®, Jevity® and Alimentum® from Ross Products Division, Abbott Laboratories). In another embodiment, an oil or acid produce in accordance with the present invention may be add to any of these formulas.

In another embodiment, a nutritional formula comprises macronutrients, vitamins, and minerals, as provided herein, in addition to the PUFAs produced in accordance with the present invention. In another embodiment, the presence of additional components helps the individual ingest the minimum daily requirements of these elements. In another embodiment, an adult and pediatric nutritional formulas comprises the PUFAs as described herein and zinc, copper, folic acid and antioxidants, or any combination thereof. In another embodiment, PUFAs produced in accordance with the present invention, or derivatives thereof, are added to a dietary substitute or supplement, particularly an infant formula, for patients undergoing intravenous feeding or for preventing or treating malnutrition or other conditions or disease states. In another embodiment, PUFAs produced in accordance with the present invention are used to alter, the composition of infant formulas in order to better replicate the PUFA content of human breast milk or to alter the presence of PUFAs normally found in a non-human mammal's milk.

In another embodiment, parenteral nutritional compositions comprising from about 2 to about 30 weight percent fatty acids calculated as triglycerides are encompassed by the present invention. In another embodiment, other vitamins, particularly fat-soluble vitamins such as vitamin A, D, E and L-carnitine are also included. In another embodiment, a preservative such as alpha-tocopherol is added in an amount of about 0.05-0.5% by weight.

In another embodiment, the present invention includes a PUFA produced in accordance with the present invention or host cells containing them, used as animal food supplements to alter an animal's tissue or milk fatty acid composition to one more desirable for human or animal consumption.

In one embodiment, the polypeptides or protein of the present invention can be provided to the individual per se. In one embodiment, the polypeptides or proteins of the present invention can be provided to the individual as part of a pharmaceutical composition where it is mixed with a pharmaceutically acceptable carrier.

In one embodiment, a "pharmaceutical composition" refers to a preparation of one or more of the active ingredients described herein with other chemical components such as physiologically suitable carriers and excipients. The purpose of a pharmaceutical composition is to facilitate administration of a compound to an organism. In one embodiment, "active ingredient" refers to the polypeptide or protein sequence of interest.

In one embodiment, the present invention provides combined preparations. In one embodiment, "a combined preparation" defines especially a "kit of parts" in the sense that the combination partners as defined above can be dosed independently or by use of different fixed combinations with distinguished amounts of the combination partners i.e., simultaneously, concurrently, separately or sequentially. In some embodiments, the parts of the kit of parts can then, e.g., be administered simultaneously or chronologically staggered, that is at different time points and with equal or different time intervals for any part of the kit of parts. The ratio of the total amounts of the combination partners, in some embodiments, can be administered in the combined preparation. In one embodiment, the combined preparation can be varied, e.g., in order to cope with the needs of a patient subpopulation to be treated or the needs of the single patient which different needs can be due to a particular disease, severity of a disease, age, sex, or body weight as can be readily made by a person skilled in the art.

In one embodiment, the phrase "physiologically acceptable carrier" refers to a carrier or a diluent that does not cause significant irritation to a tissue such as a plant tissue or a cell such as a plant cell; and does not abrogate the biological activity and properties of the protein or polynucleotide of the invention. An adjuvant is included under these phrases. In one embodiment, one of the ingredients included in the physiologically acceptable carrier can be for example polyethylene glycol (PEG), a biocompatible polymer with a wide range of solubility in both organic and aqueous media (Mutter et al. (1979).

In one embodiment, "excipient" refers to an inert substance added to the composition to further facilitate administration of an active ingredient. In one embodiment, excipients include calcium carbonate, calcium phosphate, various sugars and types of starch, cellulose derivatives, gelatin, vegetable oils and polyethylene glycols.

Techniques for formulation and administration of peptide to plants or in-vitro are known to one of skill in the art.

In one embodiment, compositions of the present invention are manufactured by processes well known in the art, e.g., by means of conventional mixing, dissolving, or lyophilizing processes.

In one embodiment, compositions for use in accordance with the present invention is formulated in conventional manner using one or more physiologically acceptable carriers comprising excipients and auxiliaries, which facilitate processing of the proteins/polynucleotides into preparations. In one embodiment, formulation is dependent upon the method of administration chosen.

The compositions also comprise, in some embodiments, preservatives, such as benzalkonium chloride and thimerosal and the like; chelating agents, such as edetate sodium and others; buffers such as phosphate, citrate and acetate; tonicity agents such as sodium chloride, potassium chloride, glycerin, mannitol and others; antioxidants such as ascorbic acid, acetylcystine, sodium metabisulfote and others; aromatic agents; viscosity adjustors, such as polymers, including cellulose and derivatives thereof; and polyvinyl alcohol and acid and bases to adjust the pH of these aqueous compositions as needed. The compositions also comprise, in some embodiments, local anesthetics or other actives. The compositions can be used as sprays, mists, drops, and the like.

Additionally, suspensions of the active ingredients, in some embodiments, are prepared as appropriate oily or water based suspensions. Suitable lipophilic solvents or vehicles include, in some embodiments, fatty oils such as sesame oil, or synthetic fatty acid esters such as ethyl oleate, triglycerides or liposomes. Aqueous injection suspensions contain, in some embodiments, substances, which increase the viscosity of the suspension, such as sodium carboxymethyl cellulose, sorbitol or dextran. In another embodiment, the suspension also contains suitable stabilizers or agents, which increase the solubility of the active ingredients to allow for the preparation of highly concentrated solutions.

In another embodiment, the proteins as described herein can be delivered in a vesicle, in particular a liposome (see Langer, Science 249:1527-1533 (1990); Treat et al., in Liposomes in the Therapy of Infectious Disease and Cancer, Lopez-Berestein and Fidler (eds.), Liss, N.Y., pp. 353-365 (1989); Lopez-Berestein, ibid., pp. 317-327; see generally ibid).

In some embodiments, the protein as described herein is in powder form for constitution with a suitable vehicle, e.g., sterile, pyrogen-free water based solution, before use. In another embodiment, compositions are contained in a container with attached atomizing means.

In some embodiments, compositions suitable for use in context of the present invention include compositions wherein the proteins or oligonucleotides are contained in an amount effective to achieve the intended purpose. In one embodiment, determination of the effective amount is well within the capability of those skilled in the art.

Some examples of substances which can serve as carriers or components thereof are sugars, such as lactose, glucose and sucrose; starches, such as corn starch and potato starch; cellulose and its derivatives, such as sodium carboxymethyl cellulose, ethyl cellulose, and methyl cellulose; powdered tragacanth; malt; gelatin; talc; solid lubricants, such as stearic acid and magnesium stearate; calcium sulfate; vegetable oils, such as peanut oil, cottonseed oil, sesame oil, olive oil, corn oil and oil of theobroma; polyols such as propylene glycol, glycerine, sorbitol, mannitol, and polyethylene glycol; alginic acid; emulsifiers, such as the Tween brand emulsifiers; wetting agents, such sodium lauryl sulfate; coloring agents; flavoring agents; tableting agents, stabilizers; antioxidants; preservatives; pyrogen-free water, isotonic saline; and phosphate buffer solutions. The choice of a pharmaceutically-acceptable carrier to be used in conjunction with the compound is basically determined by the way the compound is to be administered. If the subject compound is to be injected, in one embodiment, the pharmaceutically-acceptable carrier is sterile, physiological saline, with a blood-compatible suspending agent, the pH of which has been adjusted to about 7.4.

In addition, the compositions further comprise binders (e.g., acacia, cornstarch, gelatin, carbomer, ethyl cellulose, guar gum, hydroxypropyl cellulose, hydroxypropyl methyl cellulose, povidone), disintegrating agents (e.g., cornstarch, potato starch, alginic acid, silicon dioxide, croscarmelose sodium, crospovidone, guar gum, sodium starch glycolate), buffers (e.g., Tris-HCl, acetate, phosphate) of various pH and ionic strength, additives such as albumin or gelatin to prevent absorption to surfaces, detergents (e.g., Tween 20, Tween 80, Pluronic F68, bile acid salts), protease inhibitors, surfactants (e.g., sodium lauryl sulfate), permeation enhancers, solubilizing agents (e.g., glycerol, polyethylene glycerol), anti-oxidants (e.g., ascorbic acid, sodium metabisulfite, butylated hydroxyanisole), stabilizers (e.g., hydroxypropyl cellulose, hyroxypropylmethyl cellulose), viscosity increasing agents (e.g., carbomer, colloidal silicon dioxide, ethyl cellulose, guar gum), sweeteners (e.g., aspartame, citric acid), preservatives (e.g., Thimerosal, benzyl alcohol, parabens), lubricants (e.g., stearic acid, magnesium stearate, polyethylene glycol, sodium lauryl sulfate), flow-aids (e.g., colloidal silicon dioxide), plasticizers (e.g., diethyl phthalate, triethyl citrate), emulsifiers (e.g., carbomer, hydroxypropyl cellulose, sodium lauryl sulfate), polymer coatings (e.g., poloxamers or poloxamines), coating and film forming agents (e.g., ethyl cellulose, acrylates, polymethacrylates) and/or adjuvants.

The compositions also include incorporation of the proteins or oligonucleotides of the invention into or onto particulate preparations of polymeric compounds such as polylactic acid, polglycolic acid, hydrogels, etc., or onto liposomes, microemulsions, micelles, unilamellar or multilamellar vesicles, erythrocyte ghosts, or spheroplasts.) Such compositions will influence the physical state, solubility, stability, rate of in vivo release, and rate of in vivo clearance.

Also comprehended by the invention are particulate compositions coated with polymers (e.g. poloxamers or poloxamines) and the proteins or oligonucleotides of the invention coupled to antibodies directed against tissue-specific receptors, ligands or antigens or coupled to ligands of tissue-specific receptors.

In some embodiments, the proteins or oligonucleotides of the invention modified by the covalent attachment of water-soluble polymers such as polyethylene glycol, copolymers of polyethylene, glycol and polypropylene glycol, carboxymethyl cellulose, dextran, polyvinyl alcohol, polyvinylpyrrolidone or polyproline. In another embodiment, the modified proteins or oligonucleotides of the invention exhibit substantially longer half-lives in blood following intravenous injection than do the corresponding unmodified compounds. In one embodiment, modifications also increase the proteins or oligonucleotides solubility in aqueous solution, eliminate aggregation, enhance the physical and chemical stability of the compound, and greatly reduce the immunogenicity and reactivity of the compound. In another embodiment, the desired in vivo biological activity is achieved by the administration of such polymer-compound abducts less frequently or in lower doses than with the unmodified compound.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683, 202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N.Y. (1994), Third Edition; "Current Protocols in Immunology"Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent' and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference. Other general references are provided throughout this document.

Experimental Procedures

Strains and Growth Conditions

Axenic cultures of *P. incisa* were cultivated on BG-11 nutrient medium in 250 ml Erlenmeyer glass flasks in an incubator shaker at controlled temperature (25.degree. C.) and illumination (115 .mu.mol quanta $m^2$ $S^{-1}$) under an air/$CO_2$ atmosphere (99:1, v/v) and a speed of 170 rpm. For N-starvation experiments, cells of daily-diluted cultures were collected by centrifugation, washed three times in sterile DDW and resuspended in N-free BG11 medium. To prepare N-free BG-11 medium, sodium nitrate was omitted and ferric ammonium citrate was substituted with ferric citrate. Biomass was sampled at time 0, and in 1.5, 3, 7 and 14 days from the onset of N-starvation for determination of growth parameters, and was further used for fatty acid analysis and RNA isolation. Duplicate samples were collected from 3 separate flasks for each time point and measurement.

Growth Parameters

Dry weight and chlorophyll contents were determined as previously described in A. E. Solovchenko, I. Khozin-Goldberg, Z. Cohen, M. N. Merzlyak, Carotenoid-to-chlorophyll ratio as a proxy for assay of total fatty acids and arachidonic acid content in the green micro-alga, *Parietochloris incisa*, J. Appl. Phycol. (2008) 361-366.

RNA Isolation

Aliquots of the cultures were filtered through a glass fiber filter (GF-52, Schleicher & Schuell, Germany); cells were collected by scraping and immediately flash-frozen in liquid nitrogen and stored at −80.degree. C. for further use. Total RNA was isolated by the procedure described by Bekesiova et al. (I. Bekesiova, J. P. Nap, L. Mlynarova, Isolation of high quality DNA and RNA from leaves of the carnivorous plant *Drosera rotundifolia*, Plant. Mol. Biol. Rep. 17 (1999) 269-277), with minor modifications. Three independent RNA isolations were conducted for each time point. The total RNA samples were treated with RNAase-free Baseline-ZERO™ DNAase (Epicentre Technologies, Madison, Wis., USA) before being used in cDNA synthesis for real-time PCR experiments.

Gene Cloning

Partial sequences of the Δ12, Δ6, Δ5 desaturase and actin genes were obtained by PCR (ReddyMix PCR Master Mix, Thermo Scientific, Surrey, UK) using the degenerated primers listed in the Table 1. To generate the full-length cDNAs, 3'- and 5'-rapid amplification of the cDNA ends (RACE) was performed using a BD Smart™ RACE cDNA Amplification Kit (BD Biosciences Clontech, Foster City, Calif., USA). Gene specific primers were designed (Table 1) and RACE PCR reactions were conducted using 5' and 3'-RACE-Ready cDNAs made from 1 .mu.g total RNA of N-starved cells with 50.times. BD Advantage 2 polymerase mix (Clontech Laboratories Inc., Mountain View, Calif., USA). The PCR products of the expected sizes were excised, purified from the gel (Nucleo Spin Extract II purification kit, Machery-Nagel, Duren, Germany) and ligated into a pGEM T-Easy vector (Promega, Madison, Wis., USA). The full-length cDNAs were assembled based on the sequences of the 5' and 3' RACE fragments.

TABLE 1

Primers used for obtaining partial, 5' and 3' end fragments of actin, Δ12, Δ6 and Δ5 desaturase genes of *P. incisa* followed by full-length assembly

| Gene | Forward/Reverse primer (Sequence 5' to 3') | SEQ ID NO: |
|---|---|---|
| *Primers used for partial sequence* | | |
| DesΔ12 | CAC MYC VTS THC VWG CTG CTG VWB CCC CAC (FWD) | 9 |
|  | CTG CCC GAA GTT GAC CGC GGC GTG CTG (REV) | 10 |
| DesΔ6 | TGG TGG AAR CAY AAR CAY AAY (FWD) | 11 |
|  | GCG AGG GAT CCA AGG RAA NAR RTG RTG YTC (REV) | 12 |
| DesΔ5 | ATH RAI GRI AAR GTI TAY GAY GT (FWD) | 13 |
|  | GGI AYI KWI TSD ATR TCI GGR TC (REV) | 14 |
| Actin | AGA TCT GGC ACC ACA CCT TCT TCA (FWD) | 15 |
|  | TGT TGT TGT AGA GGT CCT TGC GGA (REV) | 16 |
| *Primers used for 5' and 3' RACE amplification* | | |
| DesΔ12 | CCACATAGCGGCACAGGCTGAAATC (FWD) | 17 |
|  | GCTCTGGGAGGATTTCAGCCTGTGC (REV) | 18 |
| DesΔ6 | GACACAATCTGGGCCGTCACAAAGTC (FWD) | 19 |
|  | GGACTTTGTGACGGCCCAGATTGTGTC (REV) | 20 |
| DesΔ5 | ACTGACCCTCCTCTGTGTCCTCTTCG (FWD) | 21 |
|  | TGTACGCCAAGTCGCTGACCATCC (REV) | 22 |

| | Primers used for full-length cloning and yeast transformations | Restriction sites*/SEQ ID NO: |
|---|---|---|
| DesΔ12 | TGGAATTCAAAATGGGGAAAGGAGGCTG (FWD) | EcoRI/23 |
|  | CTGTCTAGATCAAGCGCGGAACCACAGG | XbaI/24 |
| DesΔ6 | TCGAATTCAAAATGTGCCAGGGACAGG (FWD) | EcoRI/25 |
|  | GGCTCTAGACTAGGCCTCAGCTGCCACG | XbaI/26 |
| DesΔ5 | CCAAAGCTTAAAATGATGGCTGTAACAGA (FWD) | HindIII/27 |
|  | GCTCTAGACTATCCCACGGTGGCCA | XbaI/28 |

Expression and Functional Characterization in the Yeast *Saccharomyces Cerevisiae*

The open reading frames (ORFs) encoding for the Δ2, Δ6, and Δ5 desaturases were amplified using PfuUltra II fusion HS DNA polymerase (Stratagene, La Jolla, Calif., USA) with the respective primer pairs (Table 1). The forward primers contained a restriction site (underlined) and a yeast translation consensus (double underlined) followed by ATG. The reverse primers contained a restriction site (underlined) and a stop codon (double underlined). Following restriction and ligation to the pYES2 vector (Invitrogen, Carlsbad, Calif., USA), the constructs were used to transform S. cerevisiae strain W303 by the PEG/lithium acetate method [R. D. Gietz, R. A. Woods, Yeast Transformation by the LiAc/SS Carrier DNA/PEG Method, in: W. Xiao (Ed.), Yeast Protocols, Second Edition, vol. 313, Methods in Molecular Biology, Humana Press Inc, Totowa, N. J., 2006, pp. 107-120]. The yeast cells harboring the empty pYES2 vector were used as control. Transformants were selected by uracil prototrophy on yeast synthetic medium (YSM) lacking uracil (Invitrogen, Carlsbad, Calif., USA). For functional expression, a minimal selection medium containing 2% (w/v) raffinose was inoculated with the pYPiDesΔ12, pYPiDesΔ6 or pYPiDesΔ5 transformants and grown at 27.degree. C. for 24 h in a water bath shaker. Five ml of sterile YSM, containing 1% (w/v) Tergitol-40 and 250 .mu.M of the appropriate fatty acid substrate was inoculated with raffinose-grown cultures to obtain an OD of 0.2 at 600 nm. Expression was induced by adding galactose to a final concentration of 2% (w/v) and cultures were further grown at 27.degree. C. for 48 h. Cells were harvested by centrifugation, washed twice with 0.1% $NaHCO^3$, freeze-dried and used for fatty acid analysis.

Generation of 5' and 3' End Fragments of the Putative P. Incisa PUFA Elongase

To generate the full-length cDNA of the putative PUFA elongase, 3'- and 5'-rapid amplification of the cDNA ends (RACE) was performed using a BD Smart™ RACE cDNA Amplification Kit (BD Biosciences Clontech, Foster City, Calif.) according to the manufacturer's manual. To amplify the 5'-end, the reverse gene-specific primers (GSP) 5'-CCCG-GCTGCTGCCATGCTTCTGTG (EL5R1) (SEQ ID NO: 29) 5'-TGGGGTAGGGAGAGTAGGCCCAAGT (EL5RN) (SEQ ID NO: 30) were designed using the Primer3 online software (http://frodo.wi.mit.edu). Based on the nucleotide sequence of the obtained 5'-end fragment, two forward GSPs, 5'-GCCTACATGTCCTCTGCCGCCTGCTA (EL3R1) (SEQ ID NO: 31) and the nested, 5'-GCGGGACATGG-GAGGGCTCATCTATACC (EL3R2) (SEQ ID NO: 32), were constructed to amplify the 3'-end of the target gene. RACE PCR reactions were conducted using 5' and 3'-RACE-Ready cDNAs made from 1 ug total RNA of N-starved cells with 50.times. BD Advantage 2 polymerase mix (Clontech Laboratories Inc., Mountain View, Calif.). The PCR products of the expected size were excised and purified from the gel (NucleoSpin Extract II purification kit, Machery-Nagel, Duren, Germany) and ligated into a pGEM T-Easy vector (Promega, Madison, Wis.). The full length cDNA corresponding to the P. incisa putative PUFA elongase (designated PiELO1) was assembled from the 5' and 3' RACE fragments and its ORF was further subcloned into a pYES2 vector (Invitrogen, Carlsbad, Calif.).

Expression and Functional Characterization of PiELO1 cDNA (Elongase) in the Yeast Saccharomyces Cerevisiae The ORF encoding for PiELO1 was amplified using PfuUltra II fusion HS DNA polymerase (Stratagene, La Jolla, Calif.) with the forward primer, 5'-AGGAATTCAAAATG-GCATTGACGGCGGCCT (PUFAEL5RES1) (SEQ ID NO: 33), containing a restriction site (underlined) and a yeast translation consensus followed by ATG (double underlined) and the reverse primer 5'-CATTCTAGATTACTG-CAGCTTTTGCTTGGCTGC (PUFAEL3RES2) (SEQ ID NO: 34) containing a restriction site (underlined) and a stop codon (double underlined). The amplified sequence was then restricted with EcoRI and XbaI (NEB, Ipswich, Mass.). The expected bands were gel-purified with NucleoSpin Extract II purification kit (Machery-Nagel GmbH, Duren, Germany) and ligated into a EcoRI-Xba1 cut pYES2 vector, yielding YpPiELO1. Saccharomyces cerevisiae strain W303 was transformed with YpPiELO1 by the PEG/lithium acetate method. The yeast cells harboring the empty pYES2 vector were used as control. Transformants were selected by uracil prototrophy on yeast synthetic medium (YSM) lacking uracil (Invitrogen, Carlsbad, Calif.). For functional expression, a minimal selection medium containing 2% (w/v) raffinose was inoculated with the YpPiELO1-transformants and grown at 27.degree. C. for 24 h in a water bath shaker. Five ml of sterile YSM, containing 1% (w/v) Tergitol-40 and 250 .mu.M of the appropriate fatty acid was inoculated with raffinose-grown cultures to obtain an OD of 0.2 at 600 nm. Expression was induced by adding galactose to a final concentration of 2% (w/v) and cultures were further grown at 27.degree. C. for 48 h. Cells were harvested by centrifugation, washed twice with 0.1% $NaHCO_3$, freeze-dried and used for fatty acid analysis.

Primer Design and Validation for PiELO1 (Elongase)

Real-Time Quantitative PCR primer pairs were designed for the PiELOJ and the house keeping gene 18S SSU rRNA using the PrimerQuest tool (http://test.idtdna.com/Scitools/Applications/Primerquest/). Parameters were set for a primer length of 19 to 26 bp, primer melting temperature of 60.0+−0.1.0.degree. C., and amplicon length of 90 to 150 bases. Primer pairs were validated using seven serial fifty-fold dilutions of cDNA samples and standard curves were plotted to test for linearity of the response. The primer pairs and primer concentrations with reaction efficiencies of 100+−0.10% were chosen for quantitative RT-PCR analysis of relative gene expression. The nucleotide sequences and characteristics of primers used for quantitative RT-PCR analysis are presented in Table 2.

TABLE 2

Parameters of the primers used in RTQPCR reactions

| Gene | Forward primer Reverse primer | Amplicon size (bp) | PCR efficiency (%) |
|---|---|---|---|
| PiELO1 | AAGCTGTACGAGTTTGTGGATACGCT (SEQ ID NO: 35) (FWD) GGATATGGAAGCGTGGTGGTAGA (SEQ ID NO: 36) (REV) | 95 | 92.3 |
| 18S SSU rRNA | TGAAAGACGAACTTCTGCGAAAGCA (SEQ ID NO: 37) (FWD) AGTCGGCATCGTTTATGGTTGAGA (SEQ ID NO: 38) (REV) | 120 | 96.8 |

Calculation of Gene Transcript Levels

The mean fold changes in gene expression were calculated according to the method using the average of threshold cycle (Ct) values from triplicate cDNA-primer samples. The ΔCt followed by the ΔΔCt was calculated from the average Ct values of the target and the endogenous genes. The transcript abundance of the PiELO1 gene was normalized to the endogenous control 18S SSU rRNA gene. The fold-change in gene expression was calculated using $2^{-\Delta\Delta Ct}$ to find the expression level of the target gene which was normalized to the endogenous gene, relative to the expression of the target gene at time 0.

Fatty Acid Analysis

Fatty acid methyl esters (FAMES) were obtained by transmethylation of the freeze-dried P. incisa or yeast biomass, with dry methanol containing 2% $H_2SO_4$ (v/v) and heating at 80.degree. C. for 1.5 h while stirring under an argon atmosphere. Gas chromatographic analysis of FAMES was performed on a Thermo Ultra Gas chromatograph (Thermo Scientific, Italy) equipped with PTV injector, FID detector and a fused silica capillary column (30 m.times.0.32 mm; ZB WAXplus, Phenomenex). FAMES were identified by co-chromatography with authentic standards (Sigma Chemical Co., St. Louis, Mo.; Larodan Fine Chemicals, Malmo, Sweden) and FAME of fish oil (Larodan Fine Chemicals). Each sample was analyzed in duplicates of three independent experiments. The structures of fatty acids were confirmed by GC-MS of their pyrrolidine derivatives [W. W. Christie, The analysis of fatty acids in: W. W. Christie (Ed.), Lipid analysis Isolation, separation, identification and structural analysis of lipids, vol. 15, Third edition, The Oily Press, Bridgewater, England, 2003, pp. 205-225] on HP 5890 equipped with a mass selective detector (HP 5971A) utilizing a HP-5 capillary column and a linear temperature gradient from 120 to 300.degree. C.

Lipid Analysis

The biomass of S. cerevisiae was heated with isopropanol at 80.degree. C. for 10 min and lipids were extracted by the method of Bligh-Dyer (1959) [E. G. Bligh, W. J. Dyer, A rapid method of total lipid extraction and purification, Can. J. Biochem. Physiol. 37 (1959) 911-917]. Total lipid extract was separated into neutral and polar lipids by silica Bond-Elute cartridges (Varian, Calif.) using 1% of ethanol in chloroform (v/v) and methanol to elute neutral and polar lipids, respectively [Z. Cohen, S. Didi, Y. M. Heimer, Overproduction of .gamma.-linolenic and eicosapentaenoic acids by algae, Plant Physiol. 98 (1992) 569-572].

Polar lipids were separated into individual lipids by two dimensional TLC on Silica Gel 60 glass plates (10.times.10 cm, 0.25 mm thickness (Merck, Darmstadt, Germany) according to Khozin et al. [I. Khozin, D. Adlerstein, C. Bigogno, Y. M. Heimer, Z. Cohen, Elucidation of the Biosynthesis of Eicosapentaenoic Acid in the Microalga Porphyridium cruentum (II. Studies with Radiolabeled Precursors), Plant Physiol. 114 (1997) 223-230]. Neutral lipids were resolved with petroleum ether:diethyl ether:acetic acid (70: 30:1, v/v/v). Lipids on TLC plates were visualized by brief exposure to iodine vapors, scraped from the plates and were transmethylated for the fatty acid analysis as previously described.

Real-Time Quantitative PCR

Template cDNA for real-time quantitative PCR (RTQPCR) was synthesized using 1 .mu.g of total RNA in a total volume of 20-.mu.l, using oligo dT primer (Reverse-iT™ 1$^{st}$ Strand Synthesis Kit, ABgene, Surrey, UK). Each 20-.mu.L cDNA reaction was then diluted 3-fold with PCR grade water.

Primer Design and Validation for Real-Time Quantitative PCR

Real-Time Quantitative PCR (RTQPCR) primer pairs were designed for the PiDes12, PiDes6, and PiDes5 genes and the house keeping gene actin, PiAct using the PrimerQuest tool (http://test.idtdna.com/Scitools/Applications/Primerquest/). Primer pairs were validated as described by Iskandarov et al. [U. Iskandarov, I. Khozin-Goldberg, R. Ofir, Z. Cohen, Cloning and Characterization of the Δ6 Polyunsaturated Fatty Acid Elongase from the Green Microalga Parietochloris incisa, Lipids 44 (2009) 545-554]. The nucleotide sequences of primer pairs and the amplicon sizes are presented in Table 3.

TABLE 3

Primers used in RTQPCR experiments

| Gene | Forward primer/ Reverse primer | Amplicon size (bp) |
|---|---|---|
| PiDes12 | 5'-GAAGCACCACCAAGGATGAGGT (SEQ ID NO: 39) (FWD) 5'-AGCGAGACGAAGATGACCAGGAA (SEQ BD NO: 40) (REV) | 112 |
| PiDes6 | 5'-ACTTCCTGCACCACCAGGTCTTC (SEQ ID NO: 41) (FWD) 5'-TCGTGCTTGCTCTTCCACCAGT (SEQ ID NO: 42) (REV) | 112 |
| PiDes5 | 5'-TAAGTGCCAGGGCTGTGCTAGA (SEQ ID NO: 43) (FWD) 5'-GAACTGACCCTCCTCTGTGTCCT (SEQ ID NO: 44) (REV) | 110 |
| PiAct | 5'-CGTCCAGCTCCACGATTGAGAAGA (SEQ ID NO: 45) (FWD) 5'-ATGGAGTTGAAGGCGGTCTCGT (SEQ ID NO: 46) (REV) | 154 |

Example 1

Isolation and Identification of CDNAS for Δ12, Δ6, and Δ5 Desaturase Genes of P. Incisa The partial sequences of the Δ12, Δ6 and Δ5 desaturase gene homologues were isolated using degenerate oligonucleotides (Table 1) targeting conserved amino acid motifs identified in algae, lower plants and fungi. A partial sequence of the actin gene was amplified to be used as a house keeping gene in RTQPCR experiments.

Partial sequences of 503, 558 and 636 bp, corresponding to the Δ12, Δ6, and Δ5 desaturase genes, respectively, were used for designing gene specific primers that were used to amplify the 5'- and 3'-ends of the expected genes. Assembling the 5' and 3' RACE PCR product sequences resulted in the identification of three cDNA clones with sequence homologies to known Δ12, Δ6, and Δ5 desaturase genes. The full-length cDNAs corresponding to Δ12, Δ6, and Δ5 desaturase genes were thus designated PiDes12, PiDes6, and PiDes5. The ORFs for PiDes12, PiDes6 and PiDes5 genes were 1140, 1443, and 1446 by in length, respectively, coding for the corresponding predicted proteins of 380, 481 and 482 amino acids. The predicted amino acid sequence of PiDes12 is 64% and 62% identical to that of Chlorella vulgaris (BAB78716) and Chlamydomonas reinhardtii (XP_001691669), respectively, while it shares more than 50% identity with those of higher plants. It contains three conserved histidine motifs HxxxH, HxxHII and HxxHH. The deduced amino acid sequence of PiDes6 is 52% and 51% identical to those of the Δ6 desaturases from the liverwort M. polymorpha (AAT85661) and the moss Ceratodon purpureus, respectively (CAB94993). It is also 45% identical to the M. alpina Δ6 desaturase (ABN69090). PiDes5 shares 55 and 51% identity with the Δ5 desaturase from the microalgae M. squamata (CAQ30478), and O. tauri (CAL57370), respectively, and 54% with that from M. polymorpha (AAT85663) but is only 36% identical to the M. alpina Δ5 desaturase (AAC72755). Both PiDes6 and PiDes5 contain N-terminal fused cytochrome b5 domain including the HPGG motif and the three histidine boxes found to be conserved in front-end desaturases. The three characteristically conserved histidine-rich motifs with amino acid patterns of $HD_{(E)}xxH$, HxxHH, QxxHH in Δ6 desaturases, and HDxxH, QHxxxHH, QxxHH in Δ5 desaturases are also present in PiDes6 and PiDes5, respectively (FIG. 1).

Phylogenetic Analysis

An unrooted phylogenetic tree (FIG. 2) of PiDes12, PiDes6, PiDes5 and several functionally characterized desaturases from all three groups were constructed to identify their functional and phylogenetic relationships by the neighbor joining program in MEGA4 [K. Tamura, J. Dudley, M. Nei, S. Kumar, MEGA4: Molecular evolutionary genetics analysis (MEGA) software version 4.0, Mol. Biol. Evol. 24 (2007) 1596-1599]. The deduced amino acid sequence of PiDes12 is closely related to Δ12 desaturases of green algae and very similar to those of higher plants. The sequences of PiDes6 and PiDes5 cluster with Δ6 and Δ5 desaturases, respectively, from algae, moss and fungi. PiDes6 is highly similar to the M. polymorpha (MpDEs6) and P. tricornutum (PtD6p) Δ6 desaturases, while PiDes5 appears to be closely related to the Δ5 desaturase from the moss M. polymorpha and shares more sequence similarity with the Δ5 desaturase from the chlorophytes M. squamata and O. tauri than with those of fungal origin. However, both Δ6 or Δ5 desaturases from M. squamata and O. tauri appear to be structurally more similar to each other than to any of the known desaturases from either group.

Example 2

Functional Expression of PiDes12, PiDes6, and PiDes5 in S. Cerevisiae

Figure 3A:
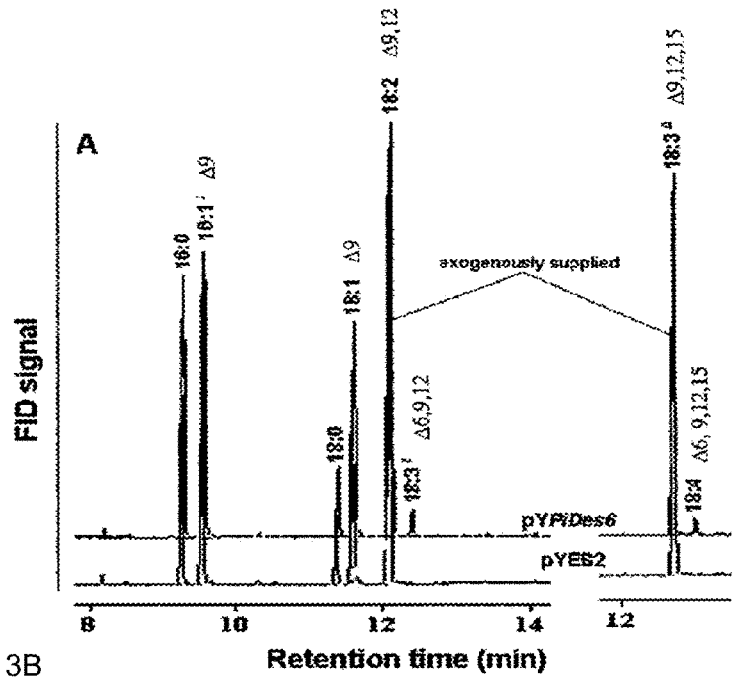
FIGS. 3A and B provide graphs representing GC FAMES of recombinant yeast harboring pYES2 (control), pY PiDes6 (A) fed with 18:2 or 18:3ω3, and pYPiDes5 (B) fed with 20:3ω6, 20:4ω3 or 18:1; and those graphs are collectively referred to as just FIG. 3.
Figure 3B:
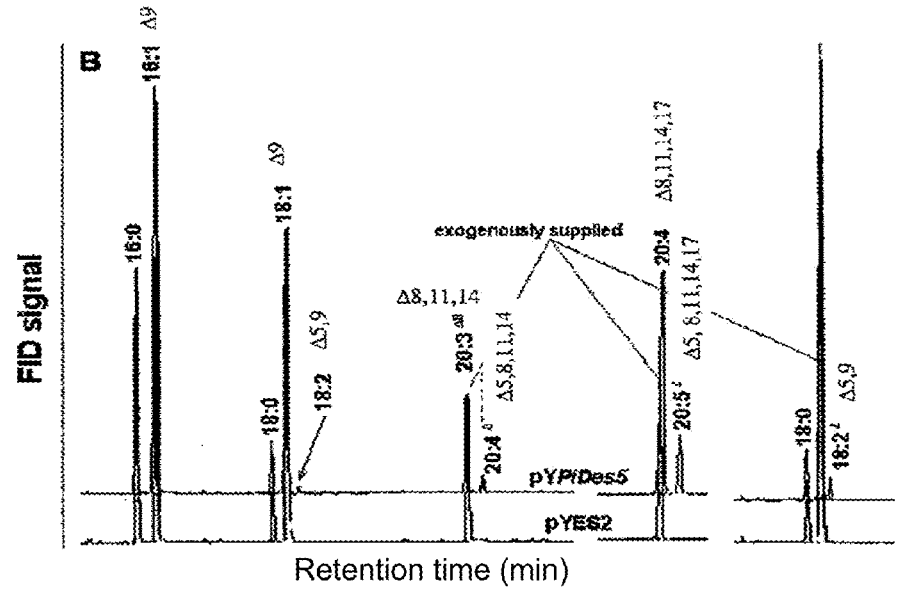

The functional activities of the proteins encoded by PiDes12, PiDes6 and PiDes5 were examined by heterologous expression in S. cerevisiae. To this aim, the pYES2 constructs pYPiDes12, pYPiDes6 and pYPiDes5 containing the ORFs for PiDes12, PiDes6, and PiDes5, respectively, were transformed into S. cerevisiae. GC analysis of the FAMEs of the yeast transformed with pYPiDes12, revealed an appearance of a small peak corresponding to 18:2 (0.3% of TFA; not shown). An attempt to improve the expression of the recombinant protein and to increase the activity by the modification of yeast translation consensus was not successful. The yeast cells harboring the empty vector, pYES2 (control) did not demonstrate desaturation activity on the added substrates (FIG. 3).

PiDes6 and PiDes5 expressions were induced in the presence of the main ω6 substrates for Δ6 or Δ5 fatty acid desaturases, 18:2ω6 and 20:3ω6, respectively. New peaks corresponding to 18:3ω6 and 20:4ω6, respectively, were detected, confirming the predicted function of PiDes6 and PiDes5. The expression of PiDes6 in the presence of 18:3ω3 resulted in the appearance of the corresponding Δ6 desaturation product 18:4ω3 (FIG. 3). PiDes6 desaturase was neither active on endogenous yeast fatty acids nor on external 18:1. PiDes6 was not active on 20:3ω3 either, whereas PiDes5 desaturated it to the non-methylene-interrupted $20:4^{\Delta 5,11,14,17}$. PiDes5 converted 20:4ω3 into the respective Δ5 product, 20:5ω3 (EPA) as well as the added 18:1 into the non-methylene-interrupted $18:2^{\Delta 5,9}$ (FIG. 3). The Δ5 position on $18:2^{\Delta 5,9}$ was determined by a characteristic peak of m/z=180 on the GC-MS spectra of its pyrrolidine derivative (not shown). The presence of $18:2^{\Delta 5,9}$ was also observed in the chromatograms of the PiDes5 transformant supplied with C20 fatty acids. In addition, a tiny peak, tentatively identified as $18:4^{\Delta 5,9,12,15}$ was present on the chromatogram of the PiDes5 transformant fed with 18:30 (Table 4).

TABLE 4

Conversion percent of the supplied fatty acids by PiDes6 and PiDes5 in S. cerevisiae

| Fatty acid substrate | Desaturase product and conversion (%)* | |
|---|---|---|
| | PiDesΔ6 | PiDesΔ5 |
| $18:1^{\Delta 9}$ | — | $18:2^{\Delta 5,9}$ (4.2) |
| $18:2^{\Delta 9,12}$ | $18:2^{\Delta 6,9,12}$ (5.1) | — |
| $18:3^{\Delta 9,12,15}$ | $18:4^{\Delta 6,9,12,15}$ (4.5) | $18:4^{\Delta 5,9,12,15}$** (1.4) |
| $18:3^{\Delta 6,9,12}$ | | |
| $20:3^{\Delta 11,14,17}$ | — | $20:4^{\Delta 5,11,14,17}$ (10.0) |
| $20:3^{\Delta 8,11,14}$ | — | $20:4^{\Delta 5,8,11,14}$ (16.4) |
| $20:4^{\Delta 8,11,14,17}$ | | $20:5^{\Delta 5,8,11,14,17}$ (17.1) |

*calculated as the ratio of product/(substrate + product)
**tentative identification A kinetic analysis of ARA emergence was conducted in total fatty acids of the PiDes5 transformant during 24 h following the addition of DGLA. Results showed that ARA peak was evident already after 3 h (corresponding to 10.9% substrate conversion) with a gradual but slow increase (up to 15.1% conversion) after 24 h. Fatty acid analysis of the major polar and neutral lipids of the yeast transformed with pYPiDes5 was performed 24 h after feeding with 20:3ω6 to study the pattern of distribution of ARA within individual lipids. In the transformed yeast, ARA appeared in all major phospholipids (Table 4), with the highest proportion detected in PC. It was also present in the neutral lipids, TAG, free fatty acids (FFA), diacylglycerol (DAG) and sterol esters (SE). Taking into account that PC, a major phospholipid of S. cerevisiae, constituted for about 16% of total lipids (Table 5), it is obvious that PC allocated the main part of ARA attached to phospholipids.

TABLE 5

Fatty acid composition and distribution of individual lipid classes of S. cerevisiae expressing the PiDes5 ORF.

| Lipid | Fatty acid composition (% of total fatty acids) | | | | | | | % conversion | % of TL* | 0:4ω6 % TL |
|---|---|---|---|---|---|---|---|---|---|---|
| | 16:0 | 16:1 | 18:0 | 18:1ω9 | $18:2^{\Delta 5,9}$ | 20:3ω6 | 20:4ω6 | | | |
| TAG | 17.4 | 27.6 | 9.6 | 23.0 | 0.4 | 19.6 | 2.0 | 9.3 | 61.3 | 55.2 |
| SE | 10.5 | 38.5 | 7.1 | 30.4 | 0.0 | 12.2 | 1.1 | 8.4 | 3.6 | 1.8 |
| DAG | 27.9 | 16.3 | 21.9 | 24.3 | 0.1 | 7.2 | 2.0 | 24.0 | 1.6 | 1.4 |
| FFA | 26.1 | 20.3 | 23.5 | 8.9 | 0.2 | 17.2 | 3.6 | 17.2 | 5.5 | 9.1 |
| PC | 19.7 | 30.1 | 9.3 | 24.3 | 0.7 | 11.6 | 3.6 | 24.2 | 15.7 | 25.7 |
| PE | 21.7 | 34.9 | 2.8 | 32.8 | 0.5 | 5.0 | 1.6 | 24.6 | 3.2 | 2.3 |
| PI + PS | 34.0 | 20.8 | 12.4 | 26.5 | 0.2 | 4.6 | 1.1 | 18.1 | 9.0 | 4.4 |

*TL—total lipids

Example 3

Figure 4:
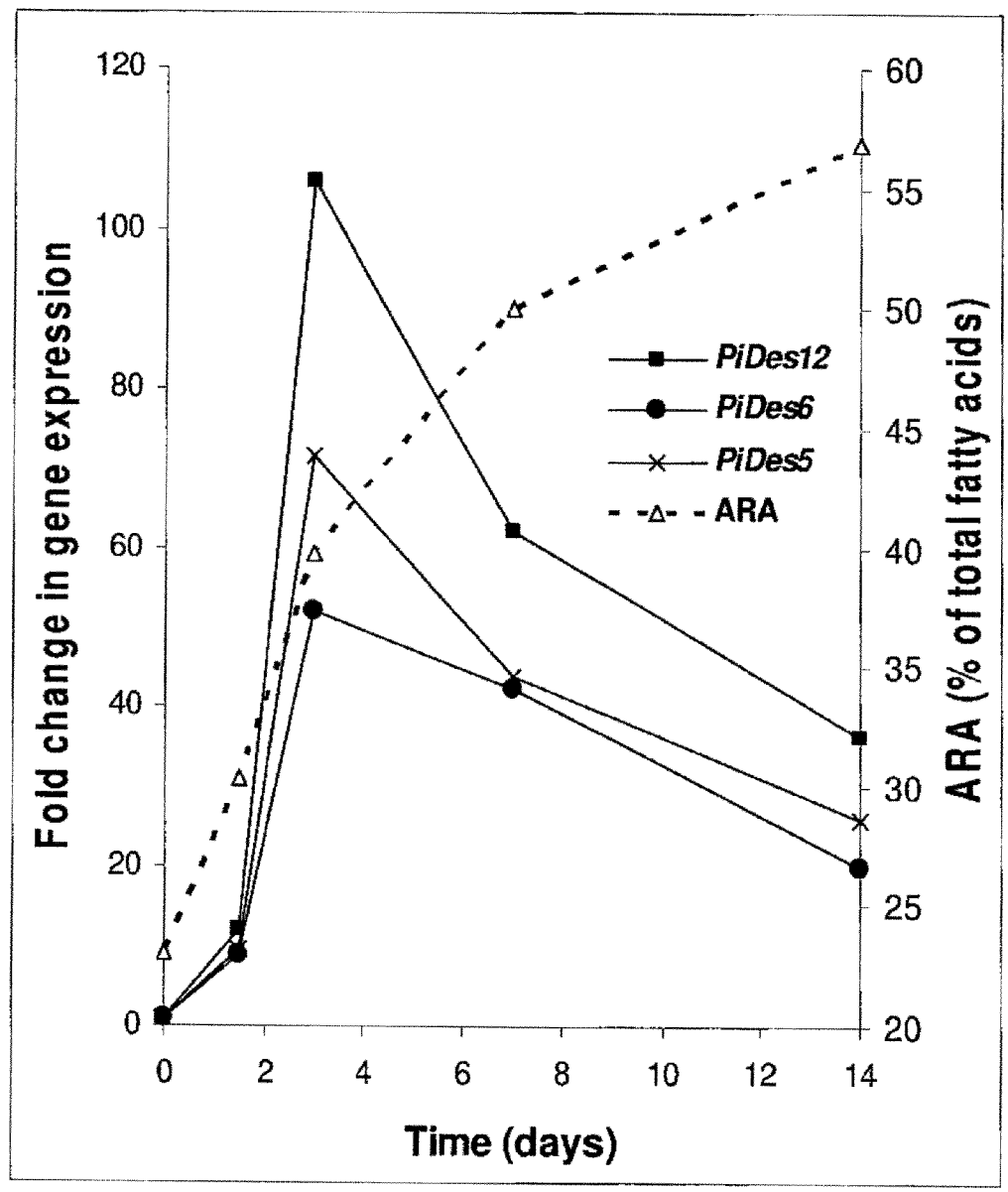
FIG. 4 is a graph showing the changes in expression of the PiDes12, PiDes6, and PiDes5 genes under N-starvation and ARA percent share in total fatty acids. The transcript abundance of the genes was normalized to that of the actin gene.

Expression Profiles of PiDes12, PiDes6, and PiDes5 Under Nitrogen Starvation To use actin as a house-keeping gene in quantitative real-time PCR experiments, a partial fragment (503 bp) of the *P. incisa* actin gene was amplified using the primers whose design was based on the *C. reinhardtii* actin cDNA (XM_001699016). Indeed, the expression level of the actin gene did not significantly change throughout the nitrogen starvation. PiDes12, PiDes6, and PiDes5 were upregulated following the transfer to Nitrogen starvation, reaching the highest expression level on day 3 and decreasing thereafter to a level about 15 to 20 fold higher than that at time 0 (FIG. 4). Both the PiDes12 and PiDes5 genes were expressed at levels approximately 65 to 70 fold higher on day 3 than at time 0, while the PiDes6 transcript was about 45 fold higher (FIG. 4). The expression patterns of PiDes12, PiDes6, and PiDes5 correlated with the enhanced biosynthesis of ARA in *P. incisa* cells (Table 6).

Figure 6:
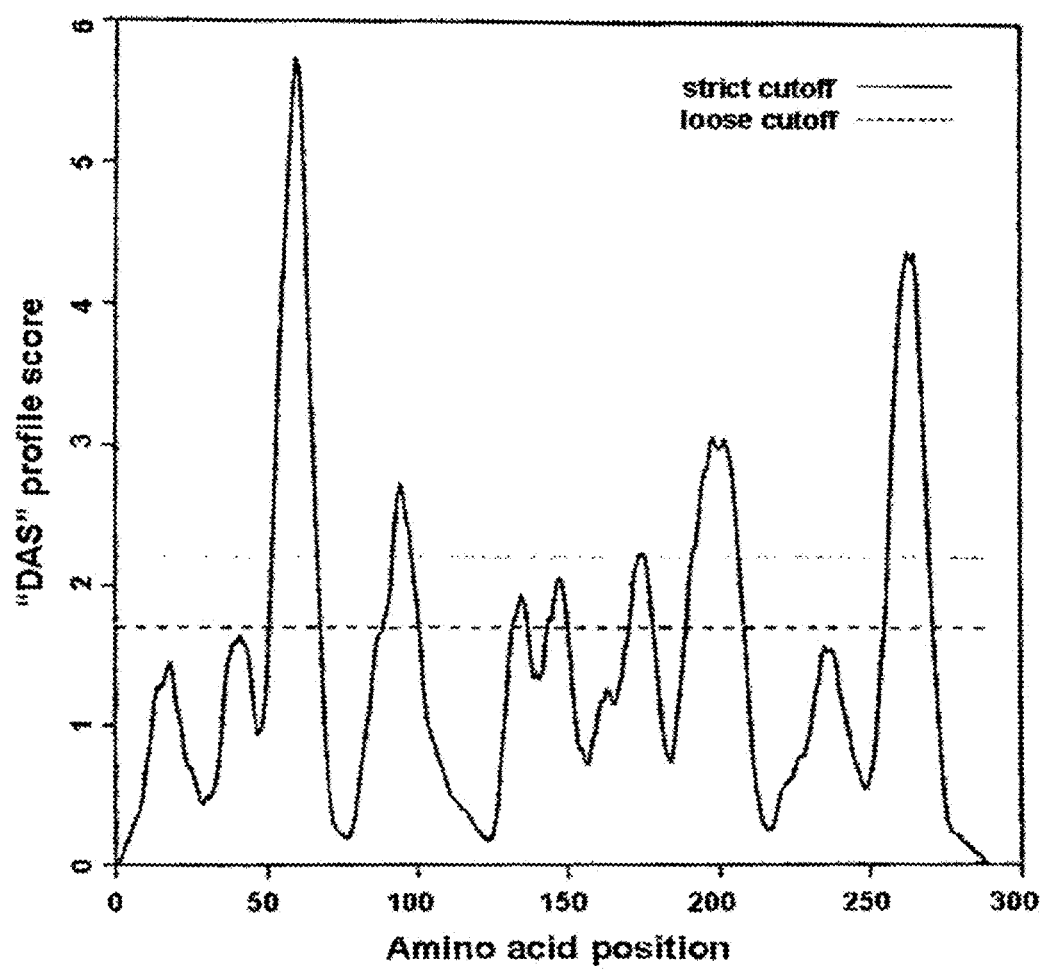
FIG. 6 is a hydropathy plot of the amino acid sequence of PiELO1. The lower dashed line and the upper line represent the loose transmembrane region cutoff and the strict transmembrane region cutoff, respectively.

PiELO1 deduced amino acid sequences was obtained using the algorithm available in the DAS transmembrane prediction server (http://www.sbc.su.se/.about.miklos/DAS/). The two strictly hydrophobic transmembrane domains were found about 50 amino acids downstream and upstream from the N and C termini, respectively, while the two less hydrophobic domains were located about 100 amino acids downstream and upstream from the N and C termini, respectively (FIG. 6).

Example 2

Phylogenetic Analysis

An unrooted phylogenetic tree of the PiELO1 and several functionally characterized PUFA elongases was constructed to identify their functional and phylogenetic relationships by the neighbor-joining program in MEGA4. According to FIG. 7 one can see that PiELO1 falls into a group of PUFA elongases of lower eukaryotes. Although the group contains mostly PUFA elongases with Δ6 activity, some Δ5 elongases, e.g., that of *M. polymorpha* and *Leishmania infantum*, are

TABLE 6

Major fatty acid composition of *P. incisa* cells grown under N-starvation

| Time (d) | Fatty acid composition (% of total fatty acids) | | | | | | | | | | | | TFA (% DW) |
|---|---|---|---|---|---|---|---|---|---|---|---|---|---|
| | 16:0 | 16:1 | 16:2 | 16:3 | 18:0 | 18:1 | 18:2 | 18:3ω6 | 18:3ω3 | 20:3ω6 | 20:4ω6 | 20:5ω3 | |
| 0 | 19.1 | 5.6 | 4.1 | 2.9 | 3.1 | 9.1 | 20.1 | 1.2 | 6.0 | 0.5 | 23.0 | 0.7 | 6.4 |
| 1.5 | 15.9 | 3.1 | 2.3 | 2.1 | 3.8 | 15.6 | 15.6 | 2.1 | 2.9 | 1.0 | 30.3 | 0.6 | 8.7 |
| 3 | 12.7 | 2.3 | 1.5 | 1.9 | 3.8 | 15.2 | 13.5 | 1.6 | 2.0 | 0.9 | 39.7 | 0.6 | 11.0 |
| 7 | 10.7 | 1.0 | 0.6 | 1.1 | 3.5 | 14.9 | 10.0 | 1.1 | 0.9 | 1.0 | 50.0 | 0.5 | 21.2 |
| 14 | 9.0 | 0.2 | 0.3 | 0.8 | 3.1 | 13.4 | 8.8 | 0.9 | 0.6 | 0.9 | 56.9 | 0.6 | 29.0 |

Example 4

Identification and Characterization of PiELO1

The BLASTX analysis (http://www.ncbi.nlm.nih.gov/blast) of clones obtained through subtractive hybridization revealed a clone of 141 bp whose putative amino acid sequence was highly homological to the C-terminal region of PUFA elongases. Using GSP primers, the 870 by 5'-end fragment was amplified and the sequence information was used to obtain the 3' end fragment from the 3' RACE Ready cDNA. Alignment of the 800 by 3'-end sequence with that of the 5'-end fragment provided an overlapping nucleotide sequence and included the partial 141 bp sequence, thus confirming the amplification of both ends of the expected gene. The assembled complete 867 by cDNA sequence, designated as PiELO1, preceded and followed by 22 and 150 by nucleotides at 5' and 3' UTR, respectively. PiELO1 contained an ORF of 289 predicted amino acid residues consistent with functionally characterized PUFA elongase ORFs from fungi, lower plants and algae (FIG. 5). The deduced amino acid sequence of the PiELO1 was 50% identical to *O. tauri* and *M. polymorpha* Δ6 PUFA elongase, while sharing 48 and 44% identity with *P. patens* Δ6 elongase and *M. polymorpha* Δ5 elongase, respectively. The PiELO1 is also similar, yet with a lower score, to Δ6 elongases of fungal origin. It shares 40 and 36% identity with the Δ6 PUFA elongases of *Thraustochytrium* and *M. alpina* (not included in the alignment), respectively.

The predicted amino acid sequence of the PiELO1 contained four conserved motifs that are characteristic for PUFA elongases (FIG. 5, highlighted). The hydropathy plot of the more related to Δ6 elongases of lower eukaryotes than to Δ5 elongases of higher eukaryotes. PiELO1 makes a closely related subgroup with OtELO1, MpELO1, MpELO2 and PpELO1, the OtELO1 being the closest one.

Functional Expression of PiELO1 in *S. Cerevisiae*

Figure 8A:
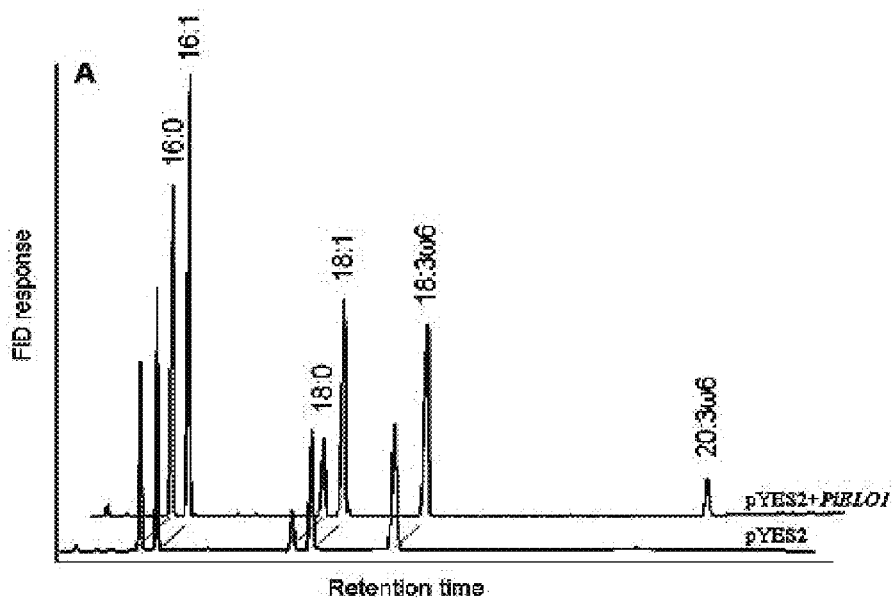
FIGS. 8A and 8B are a GC plot of FAMES of recombinant yeast harboring pYES2 and PiELO1 fed with 18:3ω6 (A) and 18:4ω3 (B) CONTROL.
Figure 8B:
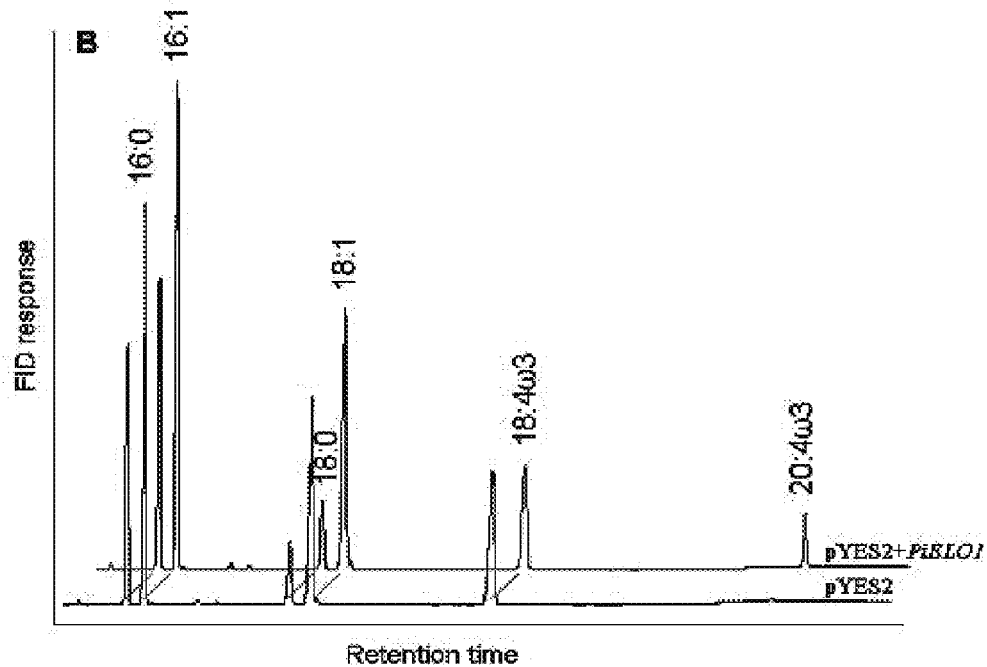

To characterize the enzymatic activity of PiELO1, the pYES2 plasmid containing the PiELO1 ORF downstream of the GAL1 promoter was transformed into *S. cerevisiae*. The PiELO1 was expressed in the presence of the Δ6 PUFA elongase substrates, 18:3ω6 (.gamma.-linolenic acid, GLA) and 18:4ω3 (stearidonic acid, STA). GC analysis of the FAMES of transformed yeast cells showed that PiELO1 elongated GLA and STA, converting them into dihomo-.gamma.-linoleic acid (DGLA, 20:3ω6) and eicosatetraenoic acid (20:4ω3), respectively (FIG. 8). The yeast cells harboring the empty vector alone did not demonstrate any elongation activity on the added substrates, confirming that the PiELO1 encoded enzyme has a Δ6 PUFA elongase activity. Feeding the PiELO1 transformants with the ω6 fatty acids, LA and ARA, did not result in their elongation (not shown).

Figure 9:
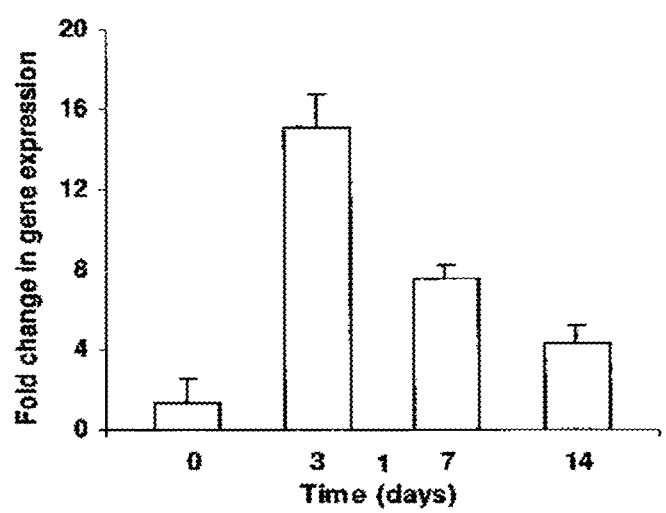
FIG. 9 is a bar graph summarizing the results of quantitative Real-time RT-PCR analysis of PiELO1 gene expression in log phase (Time 0) and N-starved (3, 7 & 14 d) cells of *P. incisa*. The transcript abundance of the gene was normalized to 18S SSU rRNA gene.

Real-time quantitative PCR was performed to quantitate the alterations in expression levels of the Δ6 PiELO1 in *P. incisa* cells under nitrogen starvation. The expression levels of the genes under nitrogen starvation were measured and normalized to the expression level of the endogenous control gene 18S SSU rRNA. The fold change in the expression level of the target genes in *P. incisa* cells grown for 3, 7 and 14 d on N-free medium was calculated relative to the expression level of the target genes in the log phase (time 0). The results showed that during nitrogen starvation the mRNA of the PiELO1 gene was induced to its highest level at day 3 (14 fold increase over time 0), decreasing thereafter to a level still higher than that of day 0 (FIG. 9). After 7 and 14 d, the expression level of the PiELO1 gene was still 7.5 and 4.3 fold higher, respectively. The level of expression of the PiELO1 gene correlated with the increase in the share of ARA and the C20/(C16+C18) elongation ratio (Table 7). The share of the elongation product, DGLA, increased sharply at day 3 (50% increase over time 0) and decreased thereafter.

TABLE 7

Major fatty acid composition of *P. incisa* cells grown under N-starvation

| Time (days) | Fatty acid composition (% of total fatty acids) | | | | | | | | | | | | | Elo. ratio[a] |
|---|---|---|---|---|---|---|---|---|---|---|---|---|---|---|
| | 16:0 | 16:1 | 16:2 | 16:3 | 18:0 | 18:1 | 18:2 | 18:3ω6 | 18:3ω3 | 20:3ω6 | 20:4ω6 | 20:5ω3 | |
| 0 | 19.1 | 5.6 | 4.1 | 2.9 | 3.1 | 9.1 | 20.1 | 1.2 | 6.0 | 0.5 | 23.0 | 0.7 | 0.34 |
| 3 | 12.7 | 2.3 | 1.5 | 1.9 | 3.8 | 15.2 | 13.5 | 1.6 | 2.0 | 0.9 | 39.7 | 0.6 | 0.74 |
| 7 | 10.7 | 1.0 | 0.6 | 1.1 | 3.5 | 14.9 | 10.0 | 1.1 | 0.9 | 1.0 | 50.0 | 0.5 | 1.10 |
| 14 | 9.0 | 0.2 | 0.3 | 0.8 | 3.1 | 13.4 | 8.8 | 0.9 | 0.6 | 0.9 | 56.9 | 0.6 | 1.44 |

[a]Elongation ratio, C20/(C18 + C16)

The capacity of *P. incisa* to accumulate large quantities of ARA-rich TAG under nitrogen starvation, suggested that it would be of great interest to study its genes and enzymes involved in the accumulation of VLC-PUFA. In the present work, *P. incisa* Δ12, Δ6, and Δ5 desaturases were cloned and studied, which in conjunction with a recently cloned Δ6 specific PUFA elongase [U. Iskandarov, I. Khozin-Goldberg, R. Ofir, Z. Cohen, Cloning and Characterization of the Δ6 Polyunsaturated Fatty Acid Elongase from the Green Microalga *Parietochloris incisa*, Lipids 44 (2009) 545-554.], represent a set of *P. incisa* genes involved in the biosynthesis of ARA. U. Iskandarov et al., 2009 is incorporated by reference as if fully set forth herein.

The his-boxes of Δ12, Δ6 and Δ5 desaturases including PiDes12, PiDes6, and PiDes5 are detailed in Table 8.

TABLE 8

Conserved histidine rich motifs of Δ12, Δ6, and Δ5 desaturases

| Des Δ12 | HECxH | HxxHH | HxxHH |
| Des Δ6 | HD$_{(E)}$xxH | HxxHH | QxxHH |
| Des Δ5 | HDxxH | QHxxxHH | QxxHH |

Notably, cysteine (C) in the first his-box and the first histidine (H) in the third his-boxes, respectively, are conserved only in Δ12 desaturases. The second residue in the first his-box of the all three types of desaturases is acidic; in Δ6 and Δ5 desaturases it is mostly aspartic acid (D), and in Δ12 desaturases mostly glutamic acid (E). This indicates the importance of an acidic residue at this position for desaturation. Similarly to other Δ6 and Δ5 desaturases glutamine (Q) is found in the third his-box of PiDes6 and PiDes5 (FIG. 1; Table 8) and in the second his-box of Δ5 desaturases. The replacement of the H residue with Q in the third his-box of Δ6 and Δ5 desaturases points to the role of Q in PUFA desaturation. Indeed, replacing this Q with histidine or isoleucine eliminated the enzyme activity of the recombinant Δ6 desaturase in yeast cells. Glutamine was also found to be highly conserved in the third his-box of the Δ4 desaturases *Pavlova lutheri* (AY332747), *Euglena gracilis* (AY278558), and *Thraustochytrium* sp. (AF489589).

Heterologous expression of PiDes6 and PiDes5 in yeast cells confirmed their Δ6 and Δ5 activity by conversion of supplemented fatty acids to the corresponding desaturation products. PiDes12 demonstrated very low desaturation activity, which could not be enhanced by the 5' modification of the inserted sequence. A similar low activity in yeast was also demonstrated in some cases, such as for Δ5 and Δ12 desaturases of *O. tauri* and *Chlorella vulgaris* NJ-7, respectively.

PiDes6 and PiDes5 desaturated both ω3 and ω6 fatty acids with similar efficiency (FIG. 3; Table 4). Various results concerning ω3/ω6 substrate preference were reported for functionally characterized Δ6 and Δ5 desaturases from different organisms that were expressed in yeast. A front-end PiDes5 desaturated its principal substrate 20:3ω6 as well as 20:4ω3; in addition, non-methylene interrupted fatty acids were also produced as a result of its activity on 20:3ω3, and on both endogenous and exogenous 18:1, but with lower efficiency. PiDes5 produced 18:2.$^{Δ5,9}$ from 18:1 but was more active when 18:1 was exogenously supplied. CrDES did insert Δ5 double bond on both 18:1 and 18:2 producing the non-methylene interrupted 18:2$^{Δ5,9}$ and 18:3$^{Δ5,9,12}$, while adding a Δ7 double bond to 20:2ω6 and 20:3ω. Apparently, in addition to the fatty acid chain length, the location and number of double bond, and the form of the substrate (lipid- or CoA bound) are also crucial for Δ5 desaturation.

PiDes6 desaturated neither the yeast major monounsaturated fatty acids nor the exogenously supplied 18:1. PiDes6 did not act on 20:3ω3, indicating that it is specific for Δ9 C18 PUFA. It appears that not only the organisms being transformed, but also the gene origin, determine the substrate specificity of the recombinant Δ6 and Δ5 desaturase. Functional characterization of PiDes6 and PiDes5 confirmed the previously reported substrate specificities of these desaturases which were generally restricted to C18 and C20 substrates, respectively.

In *P. incisa* it was shown that PC and DGTS are used for lipid-linked C18 Δ6 desaturation whereas mostly PE is used for C20 Δ5 desaturation. PiDes5 featured higher substrate conversion rate in comparison to PiDes6. A relatively fast emergence of substantial percentage of ARA (10.6% conversion after 3 h of feeding) pursued us to study ARA distribution in individual lipid classes of the transformed yeast (24 h of feeding). ARA was detected in all analyzed phospho- and neutral lipid classes of *S. cerevisiae* expressing PiDes5 (Table 5). Similar conversion percentages were determined in all analyzed phospholipids, however, ARA distribution showed preference for the major phospholipids, PC, followed by PE. In *P. incisa*, PE was found to be the main site for lipid-linked Δ5 desaturation [C. Bigogno, I. Khozin-Goldberg, D. Adlerstein, Z. Cohen, Biosynthesis of arachidonic acid in the oleaginous microalga *Parietochloris incisa* (Chlorophyceae): Radiolabeling studies, Lipids 37 (2002) 209-216], while PC, a major Δ6 acyl lipid desaturation substrate in this organism, was assumed to be utilized for Δ5 desaturation, too.

The quantitative RT-PCR results revealed that the gene expression levels of PiDes12, PiDes6, and PiDes5 followed a similar pattern during the course of nitrogen starvation. The major transcriptional activation of the all three desaturases occurred on day 3 coinciding with a sharp rise in the percentage of ARA, which almost doubled (FIG. 4, Table 6). The same expression pattern featured the *P. incisa* Δ6 PUFA elongase, however, at lower level. It was shown in radiolabeling and inhibitor studies, that ARA biosynthesis in *P. incisa* follows the ω6 pathway. The concerted transcriptional activation of the PiDes12, PiDes6, PiDes5 and PiELO1 genes was accompanied by an increase in the percent share of 18:1, a main chloroplast-derived fatty acid exported to ER and substrate of Δ12 desaturase. High expression of ARA biosynthetic genes was accompanied by enhanced Δ5 and Δ6 desaturations (Table 6).

In conclusion, the Δ12, Δ6 and Δ5 fatty acid desaturases involved in ARA biosynthesis in *P. incisa* were identified and functionally characterized. The corresponding ORFs PiDes12, PiDes6, and PiDes5, expressed in yeast confirmed their favorable enzymatic activity. Nitrogen starvation led to an increased transcription of the cloned genes reaching maximum on day 3 and enhanced accumulation of ARA thereafter. Understanding the mechanisms underlying gene transcription regulation in metabolic pathways and characteristics of enzymes involved in ARA and lipid biosynthesis in *P. incisa* is a prerequisite for manipulating algal species to produce sustainable oils of pharmaceutical and nutraceutical values.

A cDNA (PiELOJ) of an elongase encoding for a deduced protein was isolated from *P. incisa*, structurally similar to Δ6 PUFA elongase gene products from microalgae, lower plants and fungi (FIG. 5). The deduced amino acid sequence of the PiElO1 ORF was about 50% identical to that of Δ6 elongases from the liverwort *M. polymorphs* (AAT85662), the green marine microalga *O. tauri* (AAV67797) and the moss *P. patens* (AAL84174). In similarity to recently cloned PUFA elongases, the predicted protein is highly hydrophobic and has two strongly hydrophobic transmembrane regions, the first one located about 50 amino acids downstream of the N-terminus and the second one in the vicinity of the C-terminus. The PiELO1 sequence was identified in a C-terminal lysine-rich motif, important for the endoplamic reticulum targeting, as well as four conserved motifs FYxSKxxEFxDT (SEQ ID NO: 62), QxxxLHVYHHxxI (SEQ ID NO: 63), NSxxHVxMYxYY (SEQ ID NO: 64) and TxxQxxQF (SEQ ID NO: 65), including a highly conserved histidine box suggested to be functionally important for PUFA elongation (FIG. 5). These conserved motifs were not found in other classes of plant microsomal elongases, 0 ketoacyl CoA synthases and fatty acid elongases (FAE) involved in extraplastidial elongation of saturated and monounsaturated fatty acids. A variant histidine box QAFHH with three replacements in C18-Δ9-PUFA elongase IgASE1 from *I. galbana* is thought to be important for enzymatic activity rather then for substrate specificity.

PiELO1 is another example of a single step Δ6 PUFA elongases cloned from an algal species. Similarly to GLELO of *M. alpina*, PiELO1 prefers the Δ6 C18 PUFA substrates, GLA and STA. Only these Δ6 fatty acids were, when exogenously added, elongated to the respective products by *S. cerevisiae* cells transformed with PiELO1 (FIG. 8). Transformation of a higher plant so as to render it to produce Δ6 PUFA requires that the elongase used will have a high selectivity for Δ6 PUFA, thereby reducing the appearance of side products in the transformed plant. Bifunctional invertebrate PUFA elongases with both Δ6 and Δ5 activities (OmELO, XiELO, and CiELO) are less desirable in plant transformations.

Figure 7:
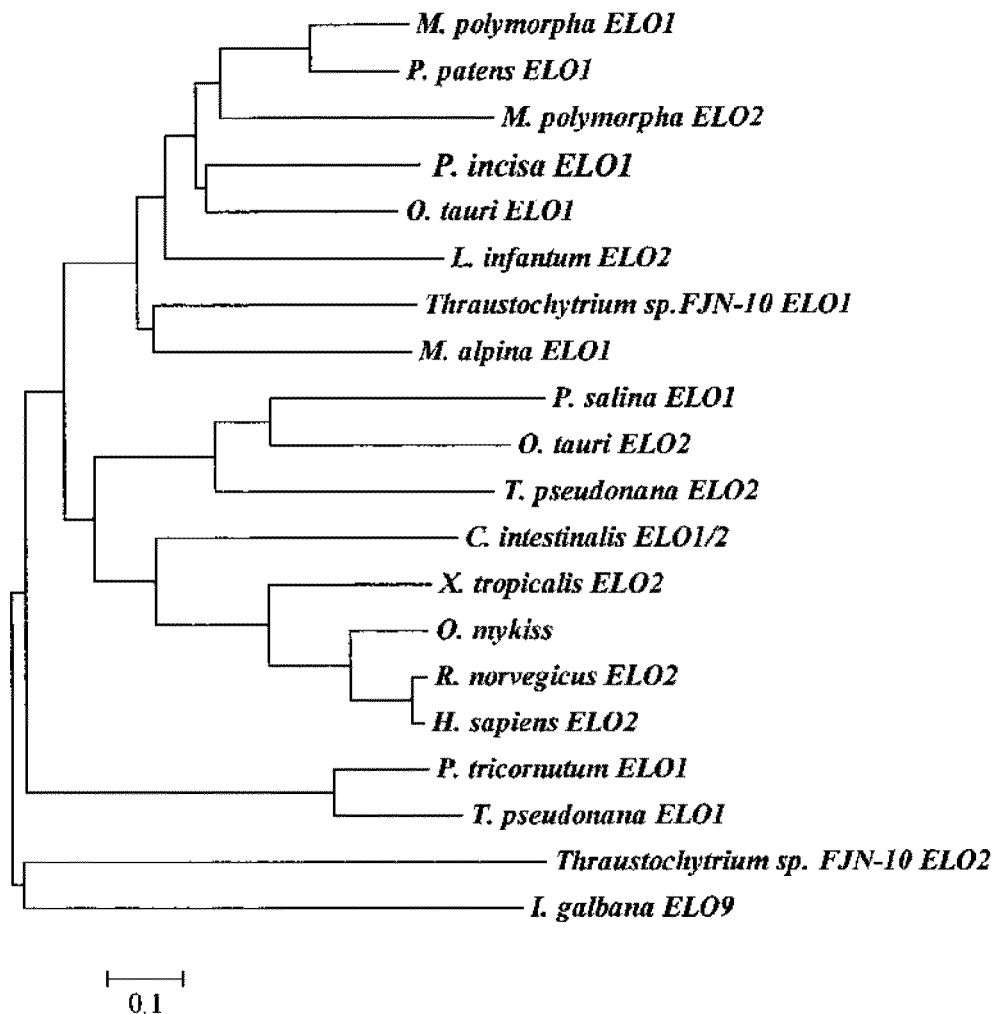
FIG. 7 is an unrooted phylogram of PiELO1 and some other functionally characterized PUFA elongases. The alignment was generated by the CLUSTAL W program and the unrooted phylogram was constructed by the neighbor-joining method using the MEGA4 software. GeneBank accession numbers for the PUFA elongases are: ACK99719 (Δ6, *P. incisa*), AAV67797 (Δ6, *O. tauri*), AAV67798 (Δ5, *O. tauri*), AAT85662 (Δ6, *M. polymorpha*), BAE71129 (Δ5, *M. polymorpha*), AAL84174 (Δ6, *P. patens*), CAJ 30819 (Δ6, *Thraustochytrium* sp.), CAM55873 (Δ5, *Thraustochytrium* sp.), AAF70417 (Δ6, *M. alpina*), XP_001467802 (*L. infantum*), AAV67803 (Δ6/Δ5, *O. mykiss*), NP_001029014 (Δ6/Δ5, *C. intestinalis*), NP_068586 (Δ6/Δ5, *H. sapiens*), AAY15135 (Δ5, *P. salina*), CAM55851 (Δ6 *P. tricornutum*), AAL37626 (Δ9, *I. galbana*), AAV67799 (Δ6, *T. pseudonana*), AAV67800 (Δ5, *T. pseudonana*), CAΔ92958 (Δ6, *C. elegans*), NP_599209 (Δ6/Δ5, *R. norvegicus*).

Phylogenetic analysis showed (FIG. 6) that the PUFA elongases are not strictly divided according to their substrate specificity. The Δ6 elongases of algal (OtELO1, TpELO1, PiELO1) and moss (PpELO1) origin are functionally restricted to the elongation of Δ6-C18-PUFAs, however these elongases are placed in separate groups on the phylogenetic tree (FIG. 7). PiELO1 is closely related to OtELO1 isolated from a chloropyte and a lower plant rather than to ELO1 genes isolated from a diatom, although both are specific for the elongation of Δ6-C18-PUFAs (FIG. 7). PiELO1 is highly similar to and is placed in the same group with both Δ6 and Δ5 elongases of the liverwort *M. polymorpha*. Kajikawa et al. suggested that MpELO2, a Δ5 elongase, is likely to have originated through gene duplication of the MpELO1 gene. The algal Δ5 PUFA elongases, OtELO2, TpELO2 and the *P. salina* ELO1 are more likely to share a common branch with the mammalian and animal Δ5 PUFA elongases, OmELO and HsELO2, while they are also similar to bifunctional PUFA elongases such as CiELO1/2.

Quantitative real timed PCR studies revealed that the expression level of the PiELO1 gene was up regulated during the time course of N-starvation (FIG. 9). Nitrogen starvation led to a continuous increase in the share of ARA and the C20/(C16+C18) elongation ratio (Table 7). However, a major transcriptional activation of PiELO1 which occurred on day 3 (14-fold increase in transcript level) coincided with the steep rise in AA accumulation and elongation ratio (Table 7). The increase in PiELO1 transcription level followed by enhanced biosynthesis of ARA may be interpreted as an increase in PiELO1 enzyme level and/or enzymatic activity. The importance of the transcriptional activation of PiELO1 is supported by the fact that PUFA elongase was the only ARA biosynthesis related gene that was obtained from the subtractive library.

The significance of the coordinated transcription and action of desaturases and elongases in ARA biosynthesis in *P. incisa* is yet to be elucidated. Possibly, the elongation of GLA by PiELO1 could be rate-limiting in ARA biosynthesis as it is in *M. alpina*. Abbadi et al. (2004) speculated that in transgenic plants modified with VLC-PUFA biosynthesis genes, substrate availability rather than enzymatic activity is rate-limiting in the Δ6 elongation of PUFA.

The invention claimed is:

1. A transgenic plant, a transgenic seed, an alga transformed cell, a transfected or a transgenic alga, comprising a polynucleotide having a coding portion encoding a protein comprising the amino acid sequence set forth in any one of SEQ ID NOs: 1-3.

2. The transgenic plant, the transgenic seed, the transformed cell, the transfected alga or the transgenic alga of claim 1, wherein said coding portion comprises a nucleic acid sequence set forth in SEQ ID NO: 4.

3. The transgenic plant, the transgenic seed, the transformed cell, the transfected alga or the transgenic alga of claim 1, wherein said coding portion comprises a nucleic acid sequence set forth in SEQ ID NO: 5.

4. The transgenic plant, the transgenic seed, the transformed cell, the transfected alga or the transgenic alga of claim 1, wherein said coding portion comprises a nucleic acid sequence set forth in SEQ ID NO: 6.

5. A composition comprising the transgenic plant, the transgenic seed, the transformed cell, the transfected alga or the transgenic alga of claim 1 and a carrier.

6. The transgenic plant, the transgenic seed, the transformed cell, the transfected alga or the transgenic alga of claim 1, wherein said polynucleotide having a coding portion encoding a protein comprising the amino acid sequence set forth in any one of SEQ ID NOs: 1-3 is an expression vector comprising a coding portion encoding a protein comprising the amino acid sequence set forth in any one of SEQ ID NOs: 1-3.

7. The transgenic plant, the transgenic seed, the transformed cell, the transfected alga or the transgenic alga of claim 1, comprising linoleic acid (LA; 18:2ω6), α-linolenic acid (ALA; 18:3ω3), oleic acid (18:1), dihomo-gamma-linolenic acid (20:3ω6), phosphatidylcholine (PC), diacylglyceroltrimethylhomoserine (DGTS), phosphatidylethanolamine (PE), or any combination thereof.

8. The transgenic plant, the transgenic seed, the transformed cell, the transfected alga or the transgenic alga of claim 1, comprising eicosapentaenoic acid (EPA, 20:5ω3), docosahexaenoic acid (DHA, 22:6ω3), dihomo-gamma-linolenic acid (DGLA), arachidonic acid (ARA, 20:4ω6), or any combination thereof.

9. The transgenic plant, the transgenic seed, the transformed cell, the transfected alga or the transgenic alga of claim 1, grown under oleogenic conditions, under nitrogen starvation conditions, or a combination thereof.

10. The transgenic plant, the transgenic seed, the transformed cell, the transfected alga or the transgenic alga of claim 1, further comprising a polynucleotide having a coding portion encoding a PUFA-specific elongase.

11. A method of producing very long-chain polyunsaturated fatty acid (VLC-PUFA) comprising, making the transgenic plant, the transgenic seed, the transformed cell, the transfected alga or the transgenic alga of claim 1.

12. The method of claim 11, wherein the transgenic plant, the transgenic seed, the transformed cell, the transfected alga or the transgenic alga is grown under oleogenic conditions, under nitrogen starvation conditions, or a combination thereof.

13. The method of claim 11, wherein said producing VLC-PUFA is enhancing oil storage, arachidonic acid accumulation, eicosapentaenoic acid accumulation, docosahexaenoic acid accumulation, dihomo-gamma-linolenic acid accumulation, or a combination thereof.

* * * * *

SEQUENCE LISTING

```
<160> NUMBER OF SEQ ID NOS: 65

<210> SEQ ID NO 1
<211> LENGTH: 379
<212> TYPE: PRT
<213> ORGANISM: Parietochloris incisa

<400> SEQUENCE: 1

Met Gly Lys Gly Gly Cys Tyr Gln Ala Gly Pro Pro Ser Ala Lys Lys
1               5                   10                  15

Trp Glu Ser Arg Val Pro Thr Ala Lys Pro Glu Phe Thr Ile Gly Thr
            20                  25                  30
```

```
Leu Arg Lys Ala Ile Pro Val His Cys Phe Glu Arg Ser Ile Pro Arg
        35                  40                  45

Ser Phe Ala Tyr Leu Ala Ala Asp Leu Ala Ala Ile Ala Val Met Tyr
 50                  55                  60

Tyr Leu Ser Thr Phe Ile Asp His Pro Ala Val Pro Arg Val Leu Ala
 65                  70                  75                  80

Trp Gly Leu Leu Trp Pro Ala Tyr Trp Tyr Phe Gln Gly Ala Val Ala
                 85                  90                  95

Thr Gly Val Trp Val Ile Ala His Glu Cys Gly His Gln Ala Phe Ser
            100                 105                 110

Pro Tyr Gln Trp Leu Asn Asp Ala Val Gly Leu Val Leu His Ser Cys
        115                 120                 125

Leu Leu Val Pro Tyr Tyr Ser Trp Lys His Ser His Arg His His
    130                 135                 140

Ser Asn Thr Gly Ser Thr Thr Lys Asp Glu Val Phe Val Pro Arg Glu
145                 150                 155                 160

Ala Ala Met Val Glu Ser Asp Phe Ser Leu Met Gln Thr Ala Pro Ala
                165                 170                 175

Arg Phe Leu Val Ile Phe Val Ser Leu Thr Ala Gly Trp Pro Ala Tyr
            180                 185                 190

Leu Phe Ala Asn Ala Ser Gly Arg Lys Tyr Gly Lys Trp Ala Asn His
        195                 200                 205

Phe Asp Pro Tyr Ser Pro Ile Phe Thr Lys Arg Glu Arg Ser Glu Ile
    210                 215                 220

Val Val Ser Asp Val Ala Leu Thr Val Val Ile Ala Gly Leu Tyr Ser
225                 230                 235                 240

Leu Gly Lys Ala Phe Gly Trp Ala Trp Leu Val Lys Glu Tyr Val Ile
                245                 250                 255

Pro Tyr Leu Ile Val Asn Met Trp Leu Val Met Ile Thr Leu Leu Gln
            260                 265                 270

His Thr His Pro Glu Leu Pro His Tyr Ala Asp Lys Glu Trp Asp Trp
        275                 280                 285

Leu Arg Gly Ala Leu Ala Thr Cys Asp Arg Ser Tyr Gly Gly Met Pro
    290                 295                 300

Asp His Leu His His His Ile Ala Asp Thr His Val Ala His His Leu
305                 310                 315                 320

Phe Ser Thr Met Pro His Tyr His Ala Gln Glu Ala Thr Glu Ala Ile
                325                 330                 335

Lys Pro Ile Leu Gly Lys Tyr Tyr Lys Gln Asp Lys Arg Asn Val Trp
            340                 345                 350

Ala Ala Leu Trp Glu Asp Phe Ser Leu Cys Arg Tyr Val Ala Pro Asp
        355                 360                 365

Thr Ala Gly Ser Gly Ile Leu Trp Phe Arg Ala
    370                 375

<210> SEQ ID NO 2
<211> LENGTH: 480
<212> TYPE: PRT
<213> ORGANISM: Parietochloris incisa

<400> SEQUENCE: 2

Met Cys Gln Gly Gln Ala Val Gln Gly Leu Arg Arg Arg Ser Ser Phe
1               5                   10                  15

Leu Lys Leu Thr Gly Asp Ala Ile Lys Gly Ala Val Ala Ala Ile Ser
            20                  25                  30
```

-continued

```
Asp Phe Asn Lys Leu Pro Ala Ala Thr Pro Val Phe Ala Arg Arg Ser
         35                  40                  45

Leu Ser Asp Ser Ala Leu Gln Gln Arg Asp Gly Pro Arg Ser Lys Gln
 50                  55                  60

Gln Val Thr Leu Glu Glu Leu Ala Gln His Asn Thr Pro Glu Asp Cys
 65                  70                  75                  80

Trp Leu Val Ile Lys Asn Lys Val Tyr Asp Val Ser Gly Trp Gly Pro
                 85                  90                  95

Gln His Pro Gly Gly His Val Ile Tyr Thr Tyr Ala Gly Lys Asp Ala
             100                 105                 110

Thr Asp Val Phe Ala Cys Phe His Ala Gln Thr Thr Trp Ser Gln Leu
             115                 120                 125

Arg Pro Phe Cys Ile Gly Asp Ile Val Glu Glu Pro Met Pro Ala
 130                 135                 140

Leu Leu Lys Asp Phe Arg Glu Leu Arg Thr Arg Leu Gln Gln Gln Gly
 145                 150                 155                 160

Leu Phe Arg Ser Asn Lys Leu Tyr Tyr Leu Tyr Lys Val Ala Ser Thr
                 165                 170                 175

Leu Ser Leu Leu Ala Ala Ala Leu Ala Val Leu Ile Thr Gln Arg Asp
             180                 185                 190

Ser Trp Leu Gly Leu Val Gly Gly Ala Phe Leu Leu Gly Leu Phe Trp
             195                 200                 205

Gln Gln Ser Gly Trp Leu Ala His Asp Phe Leu His His Gln Val Phe
 210                 215                 220

Thr Asp Arg Gln Trp Asn Asn Val Met Gly Tyr Phe Leu Gly Asn Val
 225                 230                 235                 240

Cys Gln Gly Phe Ser Thr Asp Trp Trp Lys Ser Lys His Asn Val His
                 245                 250                 255

His Ala Val Pro Asn Glu Leu Asp Ser Asp Ser Lys Ala Ala Arg Asp
             260                 265                 270

Pro Asp Ile Asp Thr Leu Pro Leu Leu Ala Trp Ser Ser Glu Met Leu
             275                 280                 285

Asp Ser Met Ser Asn Ser Gly Ala Arg Leu Phe Val Arg Met Gln His
 290                 295                 300

Tyr Phe Phe Phe Pro Ile Leu Leu Phe Ala Arg Met Ser Trp Cys Gln
 305                 310                 315                 320

Gln Ser Val Ala His Ala Ser Asp Leu Ser Arg Thr Ser Lys Ala Gly
                 325                 330                 335

Val Tyr Glu Leu Ala Tyr Leu Ala Leu His Tyr Ala Trp Phe Leu Gly
             340                 345                 350

Ala Ala Phe Ser Val Leu Pro Pro Leu Lys Ala Val Val Phe Ala Leu
             355                 360                 365

Leu Ser Gln Met Phe Ser Gly Phe Leu Leu Ser Ile Val Phe Gln
 370                 375                 380

Ser His Asn Gly Met Glu Val Tyr Ser Asp Thr Lys Asp Phe Val Thr
 385                 390                 395                 400

Ala Gln Ile Val Ser Thr Arg Asp Ile Leu Ser Asn Val Trp Asn Asp
                 405                 410                 415

Trp Phe Thr Gly Gly Leu Asn Tyr Gln Ile Glu His His Leu Phe Pro
             420                 425                 430

Thr Leu Pro Arg His Asn Leu Gly Lys Val Gln Lys Ser Ile Met Glu
             435                 440                 445
```

```
Leu Cys His Lys His Gly Leu Val Tyr Glu Asn Cys Gly Met Ala Thr
        450                 455                 460

Gly Thr Tyr Arg Val Leu Gln Arg Leu Ala Asn Val Ala Ala Glu Ala
465                 470                 475                 480

<210> SEQ ID NO 3
<211> LENGTH: 481
<212> TYPE: PRT
<213> ORGANISM: Parietochloris incisa

<400> SEQUENCE: 3

Met Met Ala Val Thr Glu Gly Ala Gly Gly Val Thr Ala Glu Val Gly
1               5                   10                  15

Leu His Lys Arg Ser Ser Gln Pro Arg Pro Ala Ala Pro Arg Ser Lys
            20                  25                  30

Leu Phe Thr Leu Asp Glu Val Ala Lys His Asp Ser Pro Thr Asp Cys
        35                  40                  45

Trp Val Val Ile Arg Arg Val Tyr Asp Val Thr Ala Trp Val Pro
    50                  55                  60

Gln His Pro Gly Gly Asn Leu Ile Phe Val Lys Ala Gly Arg Asp Cys
65                  70                  75                  80

Thr Gln Leu Phe Asp Ser Tyr His Pro Leu Ser Ala Arg Ala Val Leu
                85                  90                  95

Asp Lys Phe Tyr Ile Gly Glu Val Asp Val Arg Pro Gly Asp Glu Gln
            100                 105                 110

Phe Leu Val Ala Phe Glu Glu Asp Thr Glu Glu Gly Gln Phe Tyr Thr
        115                 120                 125

Val Leu Lys Lys Arg Val Glu Lys Tyr Phe Arg Glu Asn Lys Leu Asn
130                 135                 140

Pro Arg Ala Thr Gly Ala Met Tyr Ala Lys Ser Leu Thr Ile Leu Ala
145                 150                 155                 160

Gly Leu Ala Leu Ser Phe Tyr Gly Thr Phe Phe Ala Phe Ser Ser Ala
                165                 170                 175

Pro Ala Ser Leu Leu Ser Ala Val Leu Leu Gly Ile Cys Met Ala Glu
            180                 185                 190

Val Gly Val Ser Ile Met His Asp Ala Asn His Gly Ala Phe Ala Arg
        195                 200                 205

Asn Thr Trp Ala Ser His Ala Leu Gly Ala Thr Leu Asp Ile Val Gly
210                 215                 220

Ala Ser Ser Phe Met Trp Arg Gln Gln His Val Val Gly His His Ala
225                 230                 235                 240

Tyr Thr Asn Val Asp Gly Gln Asp Pro Asp Leu Arg Val Lys Asp Pro
                245                 250                 255

Asp Val Arg Arg Val Thr Lys Phe Gln Pro Gln Ser Tyr Gln Ala
            260                 265                 270

Tyr Gln His Ile Tyr Leu Ala Phe Leu Tyr Gly Leu Leu Ala Ile Lys
        275                 280                 285

Ser Val Leu Leu Asp Asp Phe Met Ala Leu Ser Ser Gly Ala Ile Gly
    290                 295                 300

Ser Val Lys Val Ala Lys Leu Thr Pro Gly Glu Lys Leu Val Phe Trp
305                 310                 315                 320

Gly Gly Lys Ala Leu Trp Leu Gly Tyr Phe Val Leu Pro Val Val
                325                 330                 335

Lys Ser Arg His Ser Trp Pro Leu Leu Ala Ala Cys Trp Leu Leu Ser
            340                 345                 350
```

```
Glu Phe Val Thr Gly Trp Met Leu Ala Phe Met Phe Gln Val Ala His
            355                 360                 365

Val Thr Ser Asp Val Ser Tyr Leu Glu Ala Asp Lys Thr Gly Lys Val
    370                 375                 380

Pro Arg Gly Trp Ala Ala Ala Gln Ala Ala Thr Thr Ala Asp Phe Ala
385                 390                 395                 400

His Gly Ser Trp Phe Trp Thr Gln Ile Ser Gly Leu Asn Tyr Gln
                405                 410                 415

Val Val His His Leu Phe Pro Gly Ile Cys His Leu His Tyr Pro Ala
            420                 425                 430

Ile Ala Pro Ile Val Leu Asp Thr Cys Lys Glu Phe Asn Val Pro Tyr
            435                 440                 445

His Val Tyr Pro Thr Phe Val Arg Ala Leu Ala Ala His Phe Lys His
            450                 455                 460

Leu Lys Asp Met Gly Ala Pro Thr Ala Ile Pro Ser Leu Ala Thr Val
465                 470                 475                 480

Gly

<210> SEQ ID NO 4
<211> LENGTH: 1140
<212> TYPE: DNA
<213> ORGANISM: Parietochloris incisa

<400> SEQUENCE: 4
atggggaaag gaggctgtta ccaggccggg cctcctagcg caaagaaatg ggagagtagg      60
gtgcccactg ccaaacccga gttcacgatc ggaaccctcc gcaaagctat accggtccac     120
tgcttcgaac ggtccatccc tcggtccttt gcctaccttg cggcagacct ggcggctatt     180
gcggtcatgt actacctgag cactttcatc gatcatcccg ccgtgccgcg gtcctggcc      240 tggggtttgc tgtggcctgc ctactggtac ttccaaggtg ctgtggcgac aggcgtctgg     300
gtgattgctc acgagtgcgg ccaccaggcg ttctcgccct accagtggct caacgacgct     360
gtggggcttg tgctgcactc ctgcttgctg tgccctatt actcctggaa gcactcacac      420
agacggcacc actccaacac cggaagcacc accaaggatg aggtgtttgt ccccggggaa     480
gcagccatgg tggagtcgga cttctccttg atgcagacag ctcccgcgcg gttcctggtc     540
atcttcgtct cgctgaccgc tggctggcct gcctacctgt ttgccaatgc atctggccgc     600
aagtatggca gtgggccaa ccactttgac ccctactcac ccatcttcac caagcgcgag     660
cgcagcgaga tcgttgtcag cgatgtcgcg ctgacggtgg tcatcgcggg gctctactcg     720
ctgggcaagg cgtttggctg ggcctggctg gtcaaggagt atgtgatccc ctacctcatc     780
gtcaacatgt ggctggtcat gatcacgctg ctgcagcaca cgcaccccga gctgccgcac     840
tacgccgaca aggagtggga ctggctgcgc ggcgcgctgg ccacctgcga tcgcagctac     900
ggcggcatgc cggaccacct gcaccaccac atcgccgaca cgcacgtcgc tcaccacctg     960
ttctccacca tgccgcacta ccatgcgcag gaggcgactg aggcgatcaa gcccatcctg    1020
ggcaagtact acaagcagga caagcgcaac gtctgggcag cgctctggga ggatttcagc    1080
ctgtgccgct atgtggcgcc tgacacagca ggctcgggca tcctgtggtt ccgcgcttga    1140

<210> SEQ ID NO 5
<211> LENGTH: 1443
<212> TYPE: DNA
<213> ORGANISM: Parietochloris incisa
```

<400> SEQUENCE: 5

```
atgtgccagg gacaggcagt ccagggtctg aggcgccgga gttcattctt gaagctcacc      60
ggggacgcta tcaaaggggc cgttgccgca atatcagact caacaagct cccggccgca      120
acgccagtgt tcgccaggcg gtcactttcc gacagcgctc tgcagcagcg agatggcccg      180
cgcagcaagc agcaggtcac cctggaagag ctagcgcagc ataatacgcc tgaggattgc      240
tggctggtca tcaagaacaa ggtgtacgac gtcagcggtt ggggaccgca gcaccccggt      300
gggcacgtga tctatacgta tgctggcaaa gacgccacgg acgttttgc ctgcttccat       360
gcccagacca cttggtcgca gttgagaccc ttctgcatcg gggacattgt ggaggaggag      420
ccaatgccgg cgctgctcaa agacttccgc gagctgcgca cccggctgca gcagcagggc      480
ctgtttcgca gcaacaagct gtactacctg tacaaggtgg ccagcacgct gagcctactg      540
gcggccgcgc tggcagtgct gatcacgcag cgcgactcct ggctgggtct cgtcggcggc      600
gcgttcctgc tgggcctctt ctggcagcag tcggctggc tggcgcacga cttcctgcac       660
caccaggtct tcaccgaccg ccagtggaac aacgtgatgg gctacttcct gggcaacgtc      720
tgccagggct tcagcacgga ctggtggaag agcaagcaca acgtgcacca cgcggtgccc      780
aacgagctcg acgcgacag caaggcggcg cgggaccccg acatcgacac gctgcccctg       840
ctggcctgga gctcggagat gctggacagc atgagcaact cgggcgcgcg cctgtttgtg      900
cgcatgcagc actacttctt cttccccatc ctgctcttcg cgcgcatgtc ctggtgccag      960
cagtctgtcg cgcacgcctc ggacctgtcc aggacctcaa aggcgggcgt gtatgagctg     1020
gcgtatcttg cgctgcatta tgcctggttc ctgggcgcgg ccttcagcgt gctcccgccc     1080
ctcaaggcgg tcgtgttcgc gctgctcagc cagatgtttt ccggcttcct gctctccatc     1140
gtctttgtgc agagccacaa cggcatggag gtgtacagcg acacaaagga ctttgtgacg     1200
gcccagattg tgtccacgcg cgacatattg tcaaacgtct ggaacgactg gttcacaggc     1260
gggctgaact accagatcga gcaccacctg ttccccacgc tgccgcgcca caacctgggc     1320
aaggtccaga agtccatcat ggagctgtgc acaagcatg gcctggtgta cgaaaactgc      1380
ggcatggcta ctggcaccta tcgtgtgctg cagcgcctgg caaacgtggc agctgaggcc     1440
tag                                                                   1443
```

<210> SEQ ID NO 6
<211> LENGTH: 1445
<212> TYPE: DNA
<213> ORGANISM: Parietochloris incisa

<400> SEQUENCE: 6

```
atgatggctg taacagaggg cgctgggggt gtaacggccg aggttggttt gcacaaacgc      60
agttctcagc cgcgtcccgc agctccccgc agcaagctgt tcacgttgga tgaggttgca     120
aagcacgaca gcccgactga ctgctgggtg gtcattcggc ggagggttta cgacgtgacg     180
cgtgggtgcc gcagcatcct ggcggaaacc tgatctttgt gaaagctggc cgcgactgta     240
cccagctgtt cgattcctac cacccttaa gtgccagggc tgtgctagac aagttctaca      300
tcggtgaagt cgatgtaagg cctggggacg agcagttcct tgtggctttc gaagaggaca     360
cagaggaggg tcagttctac acggtcctca gaagcgtgt ggagaagtac ttcagggaga      420
acaagctcaa cccgcgggca acaggcgcca tgtacgccaa gtcgctgacc atcctggcgg     480
gcctggcgtt gagcttctat ggtacgttct ttgccttcag cagcgcaccg gcctcgctgc     540
tcagcgctgt gctgctcggc atttgcatgg cggaggtggg cgtgtccatc atgcacgatg     600
```

```
ccaaccacgg cgcatttgcc cgcaacacgt gggcctcgca tgccctgggc gccacgctgg    660
acatcgtggg ggcatcctcc ttcatgtggc gccagcagca tgtcgtgggc caccatgcat    720
acaccaacgt ggacggtcag gacccagacc tgcgagttaa ggaccccgac gttcgccgcg    780
tgaccaagtt ccagcccag cagtcgtacc aggcgtacca gcacatctac ctggccttcc    840
tgtacggcct gctggccatc aagagcgtgc tgctggacga ctttatggcc ctcagctccg    900
gcgccatcgg ctccgtgaaa gtggccaagc tgacgcccgg cgagaagctc gtgttctggg    960
gcggcaaggc gctctggctc ggctactttg tgctgctgcc ggtggtgaag agccgccact   1020
cctggccgct gctggcggcc tgctggctgc tgagcgagtt tgtcacgggc tggatgctgg   1080
ccttcatgtt ccaggtggcg cacgtgacca gcgatgtgag ctacctggag gctgacaaga   1140
caggcaaggt cccgaggggc tgggctgccg cacaggccgc caccaccgcc gactttgcgc   1200
atggctcctg gttctggacc caaatttctg gcggccttaa ctaccaggtg gtgcaccatc   1260
tgttcccggg catctgccat ctgcactacc cggccatcgc ccccatcgtg ctggacacct   1320
gcaaggagtt taacgtgccc taccatgtgt accccacgtt tgtcagggca ctcgccgcac   1380
acttcaagca tctcaaggac atgggcgccc caactgccat cccttcgctg gccaccgtgg   1440
gatag                                                              1445
```

<210> SEQ ID NO 7
<211> LENGTH: 288
<212> TYPE: PRT
<213> ORGANISM: Parietochloris incisa

<400> SEQUENCE: 7

```
Met Ala Leu Thr Ala Ala Trp His Lys Tyr Asp Ala Ile Val Ser Arg
1               5                   10                  15

Phe Val Phe Asp Gly Leu Arg Arg Val Gly Leu Gln Glu Ile Gln Gly
                20                  25                  30

His Pro Ser Val Ile Thr Ala His Leu Pro Phe Ile Ala Ser Pro Thr
            35                  40                  45

Pro Gln Val Thr Phe Val Leu Ala Tyr Leu Leu Ile Val Val Cys Gly
        50                  55                  60

Val Ala Ala Leu Arg Thr Arg Lys Ser Ser Ala Pro Arg Glu Asp Pro
65                  70                  75                  80

Ala Trp Leu Arg Leu Leu Val Gln Ala His Asn Leu Val Leu Ile Ser
                85                  90                  95

Leu Ser Ala Tyr Met Ser Ser Ala Ala Cys Tyr Tyr Ala Trp Lys Tyr
            100                 105                 110

Gly Tyr Arg Phe Trp Gly Thr Asn Tyr Ser Pro Lys Glu Arg Asp Met
        115                 120                 125

Gly Gly Leu Ile Tyr Thr Phe Tyr Val Ser Lys Leu Tyr Glu Phe Val
    130                 135                 140

Asp Thr Leu Ile Met Leu Leu Lys Gly Lys Val Glu Gln Val Ser Phe
145                 150                 155                 160

Leu His Val Tyr His His Ala Ser Ile Ser Thr Ile Trp Trp Ala Ile
                165                 170                 175

Ala Tyr Val Ala Pro Gly Gly Asp Ala Trp Tyr Cys Cys Phe Leu Asn
            180                 185                 190

Ser Leu Val His Val Leu Met Tyr Thr Tyr Tyr Leu Leu Ala Thr Leu
        195                 200                 205

Leu Gly Lys Asp Ala Lys Ala Arg Arg Lys Tyr Leu Trp Trp Gly Arg
    210                 215                 220
```

Tyr Leu Thr Gln Phe Gln Met Phe Gln Phe Val Thr Met Met Leu Glu
225                 230                 235                 240

Ala Ala Tyr Thr Trp Ala Tyr Ser Pro Tyr Pro Lys Phe Leu Ser Lys
            245                 250                 255

Leu Leu Phe Phe Tyr Met Ile Thr Leu Leu Ala Leu Phe Ala Asn Phe
        260                 265                 270

Tyr Ala Gln Lys His Gly Ser Ser Arg Ala Ala Lys Gln Lys Leu Gln
    275                 280                 285

<210> SEQ ID NO 8
<211> LENGTH: 867
<212> TYPE: DNA
<213> ORGANISM: Parietochloris incisa

<400> SEQUENCE: 8

```
atggcattga cggcggcctg gcacaagtac gacgctatcg ttagtcgctt tgttttcgat     60
ggcttgcgca gggttggcct gcaagagatt caaggccacc cctcggtgat caccgcccac    120
cttcccttca tagcctcccc aacgccacaa gtgacgttcg tgctggccta tctgctgatt    180
gttgtctgcg gggttgccgc tctgcgtacg agaaagtcgt ccgcacctcg cgaggatccg    240
gcgtggctgc gactgcttgt gcaagcgcac aacttggtgc taatcagcct tagcgcctac    300
atgtcctctg ccgcctgcta ctatgcttgg aaatacggct ataggttttg gggcacaaac    360
tatagcccca aggagcggga catgggaggg ctcatctata ccttttacgt gtccaagctg    420
tacgagtttg tggatacgct gatcatgctg ctcaagggca aggtggagca ggtttctttt    480
ttgcacgtct accaccacgc ttccatatcc acgatctggt gggcaatcgc atacgtcgca    540
cctggtggtg acgcctggta ctgctgcttc ctgaactcgc tggtccacgt actcatgtac    600
acatactacc tgcttgcgac gctgctggga aaggacgcca aggcgcggcg caagtatttg    660
tggtggggac gctacctcac tcagttccag atgttccagt ttgtgacgat gatgctcgag    720
gcagcgtaca cttgggccta ctctccctac cccaagtttt tatcaaagct gctgttcttt    780
tacatgatca ctctgttggc cctgtttgca aacttctatg cacagaagca tggcagcagc    840
cgggcagcca agcaaaagct gcagtaa                                        867
```

<210> SEQ ID NO 9
<211> LENGTH: 24
<212> TYPE: DNA
<213> ORGANISM: Parietochloris incisa

<400> SEQUENCE: 9

```
agatctggca ccacaccttc ttca                                            24
```

<210> SEQ ID NO 10
<211> LENGTH: 24
<212> TYPE: DNA
<213> ORGANISM: Parietochloris incisa

<400> SEQUENCE: 10

```
tgttgttgta gaggtccttg cgga                                            24
```

<210> SEQ ID NO 11
<211> LENGTH: 25
<212> TYPE: DNA
<213> ORGANISM: Parietochloris incisa

<400> SEQUENCE: 11
ccacatagcg gcacaggctg aaatc                                              25

<210> SEQ ID NO 12
<211> LENGTH: 25
<212> TYPE: DNA
<213> ORGANISM: Parietochloris incisa

<400> SEQUENCE: 12
gctctgggag gatttcagcc tgtgc                                              25

<210> SEQ ID NO 13
<211> LENGTH: 26
<212> TYPE: DNA
<213> ORGANISM: Parietochloris incisa

<400> SEQUENCE: 13
gacacaatct gggccgtcac aaagtc                                             26

<210> SEQ ID NO 14
<211> LENGTH: 27
<212> TYPE: DNA
<213> ORGANISM: Parietochloris incisa

<400> SEQUENCE: 14
ggactttgtg acggcccaga ttgtgtc                                            27

<210> SEQ ID NO 15
<211> LENGTH: 26
<212> TYPE: DNA
<213> ORGANISM: Parietochloris incisa

<400> SEQUENCE: 15
actgaccctc ctctgtgtcc tcttcg                                             26

<210> SEQ ID NO 16
<211> LENGTH: 24
<212> TYPE: DNA
<213> ORGANISM: Parietochloris incisa

<400> SEQUENCE: 16
tgtacgccaa gtcgctgacc atcc                                               24

<210> SEQ ID NO 17
<211> LENGTH: 28
<212> TYPE: DNA
<213> ORGANISM: Parietochloris incisa

<400> SEQUENCE: 17
tggaattcaa aatggggaaa ggaggctg                                           28

<210> SEQ ID NO 18
<211> LENGTH: 28
<212> TYPE: DNA
<213> ORGANISM: Parietochloris incisa

<400> SEQUENCE: 18
ctgtctagat caagcgcgga accacagg                                           28

<210> SEQ ID NO 19
<211> LENGTH: 27
<212> TYPE: DNA
<213> ORGANISM: Parietochloris incisa

```
<400> SEQUENCE: 19
tcgaattcaa aatgtgccag ggacagg                                        27

<210> SEQ ID NO 20
<211> LENGTH: 28
<212> TYPE: DNA
<213> ORGANISM: Parietochloris incisa

<400> SEQUENCE: 20
ggctctagac taggcctcag ctgccacg                                       28

<210> SEQ ID NO 21
<211> LENGTH: 29
<212> TYPE: DNA
<213> ORGANISM: Parietochloris incisa

<400> SEQUENCE: 21
ccaaagctta aatgatggc tgtaacaga                                       29

<210> SEQ ID NO 22
<211> LENGTH: 25
<212> TYPE: DNA
<213> ORGANISM: Parietochloris incisa

<400> SEQUENCE: 22
gctctagact atcccacggt ggcca                                          25

<210> SEQ ID NO 23
<211> LENGTH: 24
<212> TYPE: DNA
<213> ORGANISM: Parietochloris incisa

<400> SEQUENCE: 23
cccggctgct gccatgcttc tgtg                                           24

<210> SEQ ID NO 24
<211> LENGTH: 25
<212> TYPE: DNA
<213> ORGANISM: Parietochloris incisa

<400> SEQUENCE: 24
tggggtaggg agagtaggcc caagt                                          25

<210> SEQ ID NO 25
<211> LENGTH: 26
<212> TYPE: DNA
<213> ORGANISM: Parietochloris incisa

<400> SEQUENCE: 25
gcctacatgt cctctgccgc ctgcta                                         26

<210> SEQ ID NO 26
<211> LENGTH: 28
<212> TYPE: DNA
<213> ORGANISM: Parietochloris incisa

<400> SEQUENCE: 26
gcgggacatg ggagggctca tctatacc                                       28

<210> SEQ ID NO 27
<211> LENGTH: 30
<212> TYPE: DNA
<213> ORGANISM: Parietochloris incisa
```

<400> SEQUENCE: 27
aggaattcaa aatggcattg acggcggcct                              30

<210> SEQ ID NO 28
<211> LENGTH: 33
<212> TYPE: DNA
<213> ORGANISM: Parietochloris incisa

<400> SEQUENCE: 28
cattctagat tactgcagct tttgcttggc tgc                          33

<210> SEQ ID NO 29
<211> LENGTH: 26
<212> TYPE: DNA
<213> ORGANISM: Parietochloris incisa

<400> SEQUENCE: 29
aagctgtacg agtttgtgga tacgct                                  26

<210> SEQ ID NO 30
<211> LENGTH: 23
<212> TYPE: DNA
<213> ORGANISM: Parietochloris incisa

<400> SEQUENCE: 30
ggatatggaa gcgtggtggt aga                                     23

<210> SEQ ID NO 31
<211> LENGTH: 25
<212> TYPE: DNA
<213> ORGANISM: Parietochloris incisa

<400> SEQUENCE: 31
tgaaagacga acttctgcga aagca                                   25

<210> SEQ ID NO 32
<211> LENGTH: 24
<212> TYPE: DNA
<213> ORGANISM: Parietochloris incisa

<400> SEQUENCE: 32
agtcggcatc gtttatggtt gaga                                    24

<210> SEQ ID NO 33
<211> LENGTH: 22
<212> TYPE: DNA
<213> ORGANISM: Parietochloris incisa

<400> SEQUENCE: 33
gaagcaccac caaggatgag gt                                      22

<210> SEQ ID NO 34
<211> LENGTH: 23
<212> TYPE: DNA
<213> ORGANISM: Parietochloris incisa

<400> SEQUENCE: 34
agcgagacga agatgaccag gaa                                     23

<210> SEQ ID NO 35
<211> LENGTH: 23
<212> TYPE: DNA
<213> ORGANISM: Parietochloris incisa -continued

```
<400> SEQUENCE: 35
acttcctgca ccaccaggtc ttc                                            23

<210> SEQ ID NO 36
<211> LENGTH: 22
<212> TYPE: DNA
<213> ORGANISM: Parietochloris incisa

<400> SEQUENCE: 36
tcgtgcttgc tcttccacca gt                                             22

<210> SEQ ID NO 37
<211> LENGTH: 22
<212> TYPE: DNA
<213> ORGANISM: Parietochloris incisa

<400> SEQUENCE: 37
taagtgccag ggctgtgcta ga                                             22

<210> SEQ ID NO 38
<211> LENGTH: 23
<212> TYPE: DNA
<213> ORGANISM: Parietochloris incisa

<400> SEQUENCE: 38
gaactgaccc tcctctgtgt cct                                            23

<210> SEQ ID NO 39
<211> LENGTH: 24
<212> TYPE: DNA
<213> ORGANISM: Parietochloris incisa

<400> SEQUENCE: 39
cgtccagctc cacgattgag aaga                                           24

<210> SEQ ID NO 40
<211> LENGTH: 22
<212> TYPE: DNA
<213> ORGANISM: Parietochloris incisa

<400> SEQUENCE: 40
atggagttga aggcggtctc gt                                             22

<210> SEQ ID NO 41
<211> LENGTH: 376
<212> TYPE: PRT
<213> ORGANISM: Chlorella vulgaris

<400> SEQUENCE: 41

Met Ala Ala Thr Arg Arg Ala Pro Ser Ala Glu Gly Trp Thr Arg Gln
1               5                   10                  15

Pro Val Asn Thr Lys Pro Ala Phe Ser Val Ser Thr Leu Arg Lys Ala
            20                  25                  30

Ile Pro Ala His Cys Trp Gln Arg Ser Leu Pro Arg Ser Cys Ala Tyr
        35                  40                  45

Leu Ala Ala Asp Leu Leu Ala Leu Ala Ala Leu Val Trp Ala Ser Thr
    50                  55                  60

Phe Ile Asp Ala Ala Pro Val Pro Ala Ala Val Arg Trp Leu Ala Leu
65                  70                  75                  80

Trp Pro Ala Tyr Trp Tyr Leu Ala Gly Ala Val Ala Thr Gly Ile Trp
                85                  90                  95
```

```
Val Ile Ala His Glu Cys Gly His Gln Ala Phe Ser Asp Tyr Gln Ala
                100                 105                 110

Val Asn Asp Gly Val Gly Leu Val Leu His Ser Leu Leu Leu Val Pro
            115                 120                 125

Tyr Tyr Ser Trp Lys His Ser His Arg Arg His His Ser Asn Thr Gly
130                 135                 140

Asn Val Val Lys Asp Glu Val Phe Val Pro Pro Thr Arg Glu Glu Val
145                 150                 155                 160

Ser Asp Lys Trp Glu Leu Glu Gln Ala Trp Pro Ile Arg Leu Val Lys
                165                 170                 175

Leu Phe Ile Thr Leu Thr Leu Gly Trp Pro Leu Tyr Leu Ala Phe Asn
            180                 185                 190

Val Ala Ser Arg Pro Tyr Glu Lys Ser Trp Val Asn His Phe Asp Pro
        195                 200                 205

Trp Ser Pro Ile Phe Ser Lys Arg Glu Leu Val Glu Val Ala Val Ser
    210                 215                 220

Asp Ala Ala Leu Val Ala Val Leu Cys Gly Leu Arg Gln Leu Ala Ala
225                 230                 235                 240

Ser Phe Gly Trp Ala Trp Leu Val Lys Thr Trp Leu Val Pro Tyr Leu
                245                 250                 255

Val Val Asn Phe Trp Leu Val Thr Ile Thr Met Leu Gln His Ser His
            260                 265                 270

Pro Glu Leu Pro His Tyr Gly Glu Asp Glu Trp Asp Trp Leu Arg Gly
        275                 280                 285

Ala Leu Thr Thr Val Asp Arg Asp Tyr Gly Trp Leu Leu Asn Ser Leu
    290                 295                 300

His His Ile Ala Asp Thr His Val Ala His His Leu Phe Ser Gln
305                 310                 315                 320

Met Pro His Tyr His Ala Gln Glu Ala Thr Glu Ala Leu Lys Pro Val
                325                 330                 335

Leu Gly Asp Tyr Tyr Arg Ser Asp Ser Arg Pro Leu Leu Gln Ala Ile
            340                 345                 350

Trp Gln Asp Phe Gly Ser Cys Arg Tyr Val Ala Pro Asp Thr Pro Gly
        355                 360                 365

Asp Gly Val Leu Trp Phe Arg Lys
370                 375

<210> SEQ ID NO 42
<211> LENGTH: 383
<212> TYPE: PRT
<213> ORGANISM: Chlamydomonas reinhardtii

<400> SEQUENCE: 42

Met Thr Val Thr Arg Arg Lys Gly Val Asn Ile Gln Ala Asp Ala Thr
1               5                   10                  15

Asp Ser Ala Gly Glu Lys Gln Arg Tyr Pro Ala Ala Pro Thr Phe
            20                  25                  30

Ser Leu Gly Asp Ile Arg Lys Ala Ile Pro Ala His Cys Phe Glu Lys
        35                  40                  45

Ser Ala Leu Arg Ser Phe Ala His Leu Ala Val Asp Val Thr Val Cys
    50                  55                  60

Ala Trp Leu Trp Tyr Gly Ser Thr Phe Ile Asp His Pro Ala Val Pro
65                  70                  75                  80

Arg Tyr Leu Ala Trp Phe Val Leu Trp Pro Leu Tyr Trp Phe Trp Gln
                85                  90                  95
```

Gly Ala Phe Met Thr Gly Ile Trp Val Ile Ala His Glu Cys Gly His
            100                 105                 110

Gly Ala Phe Ser Asn Ser Glu Ala Leu Asn Asp Gly Val Gly Leu Val
            115                 120                 125

Met His Ser Leu Leu Val Pro Tyr Tyr Ser Trp Lys His Ser His
        130                 135                 140

Arg Arg His His Gln Asn Thr Gly Ser Thr Ala Lys Asp Glu Val Phe
145                 150                 155                 160

Val Pro Ala Val Lys Pro Ala Gly Thr Lys Ala Pro Trp Tyr His Arg
                165                 170                 175

Asn Pro Val Tyr Arg Leu Gly His Ile Leu Phe Gln Gln Leu Leu Gly
            180                 185                 190

Trp Pro Leu Tyr Leu Leu Phe Asn Val Ser Gly His Glu Tyr Pro Arg
        195                 200                 205

Trp Ala Asn His Phe Asp Pro Phe Ser Pro Ile Phe Thr Lys Arg Glu
    210                 215                 220

Arg Ile Glu Val Leu Val Ser Asp Ile Ala Leu Ala Val Val Val Ala
225                 230                 235                 240

Gly Leu Ala Ala Ile Ser Arg Thr Trp Gly Phe Met Phe Leu Leu Lys
                245                 250                 255

Thr Tyr Leu Ile Pro Tyr Leu Val Val Asn His Trp Leu Val Met Ile
            260                 265                 270

Thr Phe Leu Gln His Thr His Pro Lys Leu Pro His Tyr Gly Asp Gly
        275                 280                 285

Glu Trp Asp Trp Leu Arg Gly Ala Met Ala Thr Val Asp Arg Ser Tyr
    290                 295                 300

Gly Val Leu Asp His Val Phe His His Ile Ala Asp Thr His Val Ala
305                 310                 315                 320

His His Leu Phe Ser Tyr Met Pro His Tyr His Ala Glu Glu Ala Thr
                325                 330                 335

Glu Ala Ile Lys Lys Val Leu Gly Asp Tyr Tyr Ala Tyr Asp Ser Arg
            340                 345                 350

Asn Val Phe Arg Ala Leu Trp Asp Glu Val Gly Gly Cys Ala Val Val
        355                 360                 365

Ala Pro Asp Thr Asn Gly Pro Glu Gln Val Tyr Trp Tyr His Arg
    370                 375                 380

<210> SEQ ID NO 43
<211> LENGTH: 384
<212> TYPE: PRT
<213> ORGANISM: Gossypium hirsutum

<400> SEQUENCE: 43

Met Gly Ala Gly Gly Arg Met Ser Val Pro Pro Ser Gln Arg Lys Gln
1               5                   10                  15

Glu Ser Gly Ser Met Lys Arg Val Pro Ile Ser Lys Pro Pro Phe Thr
            20                  25                  30

Leu Ser Glu Ile Lys Lys Ala Ile Pro Pro His Cys Phe Gln Arg Ser
        35                  40                  45

Leu Ile Arg Ser Phe Ser Tyr Leu Val Tyr Asp Phe Ile Leu Val Ser
    50                  55                  60

Ile Phe Tyr Tyr Val Ala Thr Thr Tyr Phe His Asn Leu Pro Gln Pro
65                  70                  75                  80

Leu Ser Phe Val Ala Trp Pro Ile Tyr Trp Thr Leu Gln Gly Ser Val
                85                  90                  95

```
Leu Thr Gly Val Trp Val Ile Ala His Glu Cys Gly His His Ala Phe
                100                 105                 110

Ser Asp Tyr Gln Trp Ile Asp Asp Thr Val Gly Leu Ile Leu His Ser
            115                 120                 125

Ser Leu Leu Val Pro Tyr Phe Ser Trp Lys Tyr Ser His Arg Arg His
        130                 135                 140

His Ser Asn Thr Gly Ser Leu Glu Arg Asp Glu Val Phe Val Pro Lys
145                 150                 155                 160

Lys Arg Ser Ser Ile Arg Trp Trp Ala Lys Tyr Leu Asn Asn Pro Pro
                165                 170                 175

Gly Arg Phe Val Thr Val Thr Ile Gln Leu Thr Leu Gly Trp Pro Leu
            180                 185                 190

Tyr Leu Ala Phe Asn Val Ala Gly Arg Pro Tyr Glu Gly Leu Ala Cys
        195                 200                 205

His Tyr Asn Pro Tyr Gly Pro Ile Tyr Asn Asp Arg Glu Arg Leu Gln
210                 215                 220

Ile Tyr Ile Ser Asp Val Gly Val Leu Ala Val Thr Tyr Gly Leu Tyr
225                 230                 235                 240

Arg Leu Val Leu Ala Lys Gly Leu Ala Trp Val Ile Cys Val Tyr Gly
                245                 250                 255

Val Pro Leu Leu Ile Val Asn Ala Phe Leu Val Met Ile Thr Tyr Leu
            260                 265                 270

Gln His Thr His Pro Ala Leu Pro His Tyr Asp Ser Glu Trp Asp
        275                 280                 285

Trp Leu Arg Gly Ala Leu Ala Thr Val Asp Arg Asp Tyr Gly Ile Leu
290                 295                 300

Asn Lys Val Phe His Asn Ile Thr Asp Thr His Val Ala His His Leu
305                 310                 315                 320

Phe Ser Thr Met Pro His Tyr His Ala Met Glu Ala Thr Lys Ala Ile
                325                 330                 335

Lys Pro Ile Leu Gly Glu Tyr Tyr Ser Phe Asp Gly Thr Pro Val Tyr
            340                 345                 350

Lys Ala Ile Phe Arg Glu Ala Lys Glu Cys Ile Tyr Val Glu Pro Asp
        355                 360                 365

Glu Gly Glu Gln Ser Ser Lys Gly Val Phe Trp Phe Arg Asn Lys Ile
370                 375                 380

<210> SEQ ID NO 44
<211> LENGTH: 381
<212> TYPE: PRT
<213> ORGANISM: Olea europaea

<400> SEQUENCE: 44

Met Gly Ala Gly Gly Arg Leu Ser Val Pro Ala Thr Lys Ala Glu Glu
1               5                   10                  15

Lys Lys Asn Pro Leu Lys Arg Val Pro Tyr Leu Lys Pro Pro Phe Thr
            20                  25                  30

Val Gly Asp Ile Lys Lys Thr Ile Pro Pro His Cys Phe Lys Arg Ser
        35                  40                  45

Leu Leu Arg Ser Phe Ser Tyr Val Val Tyr Asp Leu Phe Leu Val Phe
    50                  55                  60

Leu Phe Tyr Tyr Ile Ala Thr Ser Tyr Phe His Leu Leu Pro Ser Pro
65              70                  75                  80

Phe Ser Tyr Leu Gly Trp Ser Val Tyr Trp Ile Leu Gln Gly Cys Val
                85                  90                  95
```

```
Cys Thr Gly Val Trp Val Ile Ala His Glu Cys Gly His His Ala Phe
                100                 105                 110

Ser Asp Tyr Gln Trp Val Asp Asp Thr Val Gly Leu Ile Leu His Ser
            115                 120                 125

Thr Leu Leu Val Pro Tyr Phe Ser Trp Lys Tyr Ser His Arg Arg His
        130                 135                 140

His Ser Asn Thr Gly Ser Leu Glu Arg Asp Glu Val Phe Val Pro Lys
145                 150                 155                 160

Pro Lys Ser Lys Leu Ser Trp Phe Thr Lys Tyr Leu Asn Asn Pro Pro
                165                 170                 175

Gly Arg Val Met Thr Leu Val Ile Thr Leu Thr Leu Gly Trp Pro Leu
            180                 185                 190

Tyr Leu Ala Leu Asn Val Ser Gly Arg Pro Tyr Asp Arg Phe Ala Cys
        195                 200                 205

His Tyr Asp Pro His Gly Pro Ile Tyr Asn Asp Arg Glu Arg Leu Gln
210                 215                 220

Ile Tyr Ile Ser Asp Val Cys Val Ile Ala Thr Ser Tyr Ile Leu Tyr
225                 230                 235                 240

Arg Val Ala Leu Ala Gln Gly Leu Val Trp Leu Thr Cys Val Tyr Gly
            245                 250                 255

Val Pro Leu Leu Ile Val Asn Gly Phe Leu Val Leu Ile Thr Tyr Leu
        260                 265                 270

Gln His Thr His Pro Leu Pro His Tyr Asp Ser Glu Trp Asp
            275                 280                 285

Trp Leu Arg Gly Ala Leu Ala Thr Val Asp Arg Asp Tyr Gly Val Leu
            290                 295                 300

Asn Asn Val Phe His Asn Ile Thr Asp Thr His Val Ala His His Leu
305                 310                 315                 320

Phe Ser Thr Met Pro His Tyr His Ala Met Glu Ala Thr Lys Ala Ile
                325                 330                 335

Lys Pro Leu Leu Gly Glu Tyr Tyr Gln Ser Asp Gly Thr Pro Phe Tyr
            340                 345                 350

Lys Ala Met Trp Arg Glu Ala Lys Glu Cys Leu Tyr Val Glu Pro Asp
            355                 360                 365

Glu Pro Asn Lys Gly Val Phe Trp Tyr Lys Asn Lys Phe
        370                 375                 380

<210> SEQ ID NO 45
<211> LENGTH: 382
<212> TYPE: PRT
<213> ORGANISM: Spinacia oleracea

<400> SEQUENCE: 45

Met Gly Ala Gly Gly Arg Ser Ile Pro Pro Ser Ala Arg Lys Glu Lys
1               5                   10                  15

Ser Asp Ala Leu Asn Arg Val Pro Tyr Glu Lys Pro Pro Phe Thr Leu
            20                  25                  30

Gly Gln Ile Lys Lys Ala Ile Pro Pro His Cys Phe Lys Arg Ser Val
        35                  40                  45

Leu Arg Ser Phe Ser Tyr Val Val Tyr Asp Phe Thr Ile Ala Phe Leu
    50                  55                  60

Leu Tyr Tyr Val Ala Thr Asn Tyr Ile His Leu Leu Pro Lys Pro Phe
65              70                  75                  80

Asn Tyr Leu Ala Trp Pro Val Tyr Gly Phe Val Gln Gly Cys Val Leu
                85                  90                  95
```

```
Thr Gly Val Trp Val Ile Ala His Glu Cys Gly His His Ala Phe Ser
            100                 105                 110

Asp Tyr Gln Trp Leu Asp Asp Thr Val Gly Leu Val Leu His Ser Phe
            115                 120                 125

Leu Leu Val Pro Tyr Phe Ser Trp Lys Tyr Ser His Arg Arg His His
        130                 135                 140

Ser Asn Thr Gly Ser Met Glu Lys Asp Glu Val Phe Val Pro Gln Arg
145                 150                 155                 160

Lys Glu Asn Met Ser Trp Phe Ser Lys Tyr Leu Ser Asn Pro Pro Gly
                165                 170                 175

Arg Ile Leu Thr Leu Val Val Thr Leu Thr Leu Gly Trp Pro Leu Tyr
            180                 185                 190

Leu Leu Phe Asn Val Ser Gly Arg Lys Tyr Glu Arg Phe Ala Cys His
        195                 200                 205

Tyr Asp Pro Ser Ser Pro Ile Tyr Ser Asp Arg Glu Arg Leu Gln Ile
210                 215                 220

Phe Ile Ser Asp Val Gly Ile Ser Ile Val Ala Phe Gly Leu Tyr His
225                 230                 235                 240

Leu Ala Ala Lys Gly Ile Ser Trp Val Leu Cys Val Tyr Gly Gly
            245                 250                 255

Pro Leu Val Val Asn Gly Phe Leu Val Leu Ile Thr Phe Leu Gln
        260                 265                 270

His Thr His Pro Ser Leu Pro His Tyr Asp Thr Ser Glu Trp Asp Trp
            275                 280                 285

Leu Arg Gly Ala Leu Ala Thr Ala Asp Arg Asp Tyr Gly Ile Leu Asn
    290                 295                 300

Lys Val Phe His Asn Ile Thr Asp Thr His Val Ala His His Leu Ile
305                 310                 315                 320

Ser Thr Met Pro His Tyr His Ala Met Glu Ala Thr Lys Ala Ile Lys
            325                 330                 335

Pro Ile Leu Gly Lys Tyr Tyr Arg Leu Asp Ser Thr Pro Val Phe Lys
        340                 345                 350

Ala Met Trp Arg Glu Ala Lys Glu Cys Met Tyr Val Glu Ala Asp Glu
            355                 360                 365

Asp Asp Gln Asn Lys Gly Val Leu Trp Tyr Arg Asn Lys Leu
        370                 375                 380

<210> SEQ ID NO 46
<211> LENGTH: 481
<212> TYPE: PRT
<213> ORGANISM: Marchantia polymorpha

<400> SEQUENCE: 46

Met Ala Ser Ser Thr Thr Thr Ala Val Lys Gln Ser Ser Gly Gly Leu
1               5                   10                  15

Trp Ser Lys Trp Gly Thr Gly Ser Asn Leu Ser Phe Val Ser Arg Lys
            20                  25                  30

Glu Gln Gln Gln Gln Gln Gln Ser Ser Pro Glu Ala Ser Thr Pro
        35                  40                  45

Ala Ala Gln Gln Glu Lys Ser Ile Ser Arg Glu Ser Ile Pro Glu Gly
    50                  55                  60

Phe Leu Thr Val Glu Glu Val Ser Lys His Asp Asn Pro Ser Asp Cys
65                  70                  75                  80

Trp Ile Val Ile Asn Asp Lys Val Tyr Asp Val Ser Ala Phe Gly Lys
                85                  90                  95
```

Thr His Pro Gly Gly Pro Val Ile Phe Thr Gln Ala Gly Arg Asp Ala
            100                 105                 110

Thr Asp Ser Phe Lys Val Phe His Ser Ala Lys Ala Trp Gln Phe Leu
        115                 120                 125

Gln Asp Leu Tyr Ile Gly Asp Leu Tyr Asn Ala Glu Pro Val Ser Glu
130                 135                 140

Leu Val Lys Asp Tyr Arg Asp Leu Arg Thr Ala Phe Met Arg Ser Gln
145                 150                 155                 160

Leu Phe Lys Ser Ser Lys Met Tyr Tyr Val Thr Lys Cys Val Thr Asn
                165                 170                 175

Phe Ala Ile Leu Ala Ala Ser Leu Ala Val Ile Ala Trp Ser Gln Thr
            180                 185                 190

Tyr Leu Ala Val Leu Cys Ser Ser Phe Leu Leu Ala Leu Phe Trp Gln
        195                 200                 205

Gln Cys Gly Trp Leu Ser His Asp Phe Leu His His Gln Val Thr Glu
210                 215                 220

Asn Arg Ser Leu Asn Thr Tyr Phe Gly Gly Leu Phe Trp Gly Asn Phe
225                 230                 235                 240

Ala Gln Gly Tyr Ser Val Gly Trp Trp Lys Thr Lys His Asn Val His
                245                 250                 255

His Ala Ala Thr Asn Glu Cys Asp Asp Lys Tyr Gln Pro Ile Asp Pro
            260                 265                 270

Asp Ile Asp Thr Val Pro Leu Leu Ala Trp Ser Lys Glu Ile Leu Ala
        275                 280                 285

Thr Val Asp Asp Gln Phe Phe Arg Ser Ile Ser Val Gln His Leu
290                 295                 300

Leu Phe Phe Pro Leu Leu Phe Leu Ala Arg Phe Ser Trp Leu His Ser
305                 310                 315                 320

Ser Trp Ala His Ala Ser Asn Phe Glu Met Pro Arg Tyr Met Arg Trp
                325                 330                 335

Ala Glu Lys Ala Ser Leu Leu Gly His Tyr Gly Ala Ser Ile Gly Ala
            340                 345                 350

Ala Phe Tyr Ile Leu Pro Ile Pro Gln Ala Ile Cys Trp Leu Phe Leu
        355                 360                 365

Ser Gln Leu Phe Cys Gly Ala Leu Leu Ser Ile Val Phe Val Ile Ser
370                 375                 380

His Asn Gly Met Asp Val Tyr Asn Asp Pro Arg Asp Phe Val Thr Ala
385                 390                 395                 400

Gln Val Thr Ser Thr Arg Asn Ile Glu Gly Asn Phe Phe Asn Asp Trp
                405                 410                 415

Phe Thr Gly Gly Leu Asn Arg Gln Ile Glu His His Leu Phe Pro Ser
            420                 425                 430

Leu Pro Arg His Asn Leu Ala Lys Val Ala Pro His Val Lys Ala Leu
        435                 440                 445

Cys Ala Lys His Gly Leu His Tyr Glu Glu Leu Ser Leu Gly Thr Gly
450                 455                 460

Val Cys Arg Val Phe Asn Arg Leu Val Glu Val Ala Tyr Ala Ala Lys
465                 470                 475                 480

Val

<210> SEQ ID NO 47
<211> LENGTH: 477
<212> TYPE: PRT
<213> ORGANISM: Phaeodactylum tricornutum

```
<400> SEQUENCE: 47

Met Gly Lys Gly Gly Asp Ala Arg Ala Ser Lys Gly Ser Thr Ala Ala
1               5                   10                  15

Arg Lys Ile Ser Trp Gln Glu Val Lys Thr His Ala Ser Pro Glu Asp
            20                  25                  30

Ala Trp Ile Ile His Ser Asn Lys Val Tyr Asp Val Ser Asn Trp His
        35                  40                  45

Glu His Pro Gly Gly Ala Val Ile Phe Thr His Ala Gly Asp Asp Met
    50                  55                  60

Thr Asp Ile Phe Ala Ala Phe His Ala Pro Gly Ser Gln Ser Leu Met
65                  70                  75                  80

Lys Lys Phe Tyr Ile Gly Glu Leu Leu Pro Glu Thr Thr Gly Lys Glu
                85                  90                  95

Pro Gln Gln Ile Ala Phe Glu Lys Gly Tyr Arg Asp Leu Arg Ser Lys
            100                 105                 110

Leu Ile Met Met Gly Met Phe Lys Ser Asn Lys Trp Phe Tyr Val Tyr
        115                 120                 125

Lys Cys Leu Ser Asn Met Ala Ile Trp Ala Ala Ala Cys Ala Leu Val
130                 135                 140

Phe Tyr Ser Asp Arg Phe Trp Val His Leu Ala Ser Ala Val Met Leu
145                 150                 155                 160

Gly Thr Phe Phe Gln Gln Ser Gly Trp Leu Ala His Asp Phe Leu His
                165                 170                 175

His Gln Val Phe Thr Lys Arg Lys His Gly Asp Leu Gly Leu Phe
            180                 185                 190

Trp Gly Asn Leu Met Gln Gly Tyr Ser Val Gln Trp Trp Lys Asn Lys
        195                 200                 205

His Asn Gly His His Ala Val Pro Asn Leu His Cys Ser Ser Ala Val
210                 215                 220

Ala Gln Asp Gly Asp Pro Asp Ile Asp Thr Met Pro Leu Leu Ala Trp
225                 230                 235                 240

Ser Val Gln Gln Ala Gln Ser Tyr Arg Glu Leu Gln Ala Asp Gly Lys
                245                 250                 255

Asp Ser Gly Leu Val Lys Phe Met Ile Arg Asn Gln Ser Tyr Phe Tyr
            260                 265                 270

Phe Pro Ile Leu Leu Leu Ala Arg Leu Ser Trp Leu Asn Glu Ser Phe
        275                 280                 285

Lys Cys Ala Phe Gly Leu Gly Ala Ala Ser Glu Asn Ala Ala Leu Glu
290                 295                 300

Leu Lys Ala Lys Gly Leu Gln Tyr Pro Leu Leu Glu Lys Ala Gly Ile
305                 310                 315                 320

Leu Leu His Tyr Ala Trp Met Leu Thr Val Ser Ser Gly Phe Gly Arg
                325                 330                 335

Phe Ser Phe Ala Tyr Thr Ala Phe Tyr Phe Leu Thr Ala Thr Ala Ser
            340                 345                 350

Cys Gly Phe Leu Leu Ala Ile Val Phe Gly Leu Gly His Asn Gly Met
        355                 360                 365

Ala Thr Tyr Asn Ala Asp Ala Arg Pro Asp Phe Trp Lys Leu Gln Val
370                 375                 380

Thr Thr Thr Arg Asn Val Thr Gly Gly His Gly Phe Pro Gln Ala Phe
385                 390                 395                 400

Val Asp Trp Phe Cys Gly Gly Leu Gln Tyr Gln Val Asp His His Leu
            405                 410                 415
```

Phe Pro Ser Leu Pro Arg His Asn Leu Ala Lys Thr His Ala Leu Val
                420                 425                 430

Glu Ser Phe Cys Lys Glu Trp Gly Val Gln Tyr His Glu Ala Asp Leu
            435                 440                 445

Val Asp Gly Thr Met Glu Val Leu His His Leu Gly Ser Val Ala Gly
450                 455                 460

Glu Phe Val Val Asp Phe Val Arg Asp Gly Pro Ala Met
465                 470                 475

<210> SEQ ID NO 48
<211> LENGTH: 484
<212> TYPE: PRT
<213> ORGANISM: Thalassiosira pseudonana

<400> SEQUENCE: 48

Met Gly Lys Gly Gly Asp Ala Ala Ala Thr Lys Arg Ser Gly Ala
1               5                   10                  15

Leu Lys Leu Ala Glu Lys Pro Gln Lys Tyr Thr Trp Gln Glu Val Lys
            20                  25                  30

Lys His Ile Thr Pro Asp Asp Ala Trp Val Val His Gln Asn Lys Val
        35                  40                  45

Tyr Asp Val Ser Asn Trp Tyr Asp His Pro Gly Gly Ala Val Val Phe
    50                  55                  60

Thr His Ala Gly Asp Asp Met Thr Asp Ile Phe Ala Ala Phe His Ala
65                  70                  75                  80

Gln Gly Ser Gln Ala Met Met Lys Phe Tyr Ile Gly Asp Leu Ile
                85                  90                  95

Pro Glu Ser Val Glu His Lys Asp Gln Arg Gln Leu Asp Phe Glu Lys
            100                 105                 110

Gly Tyr Arg Asp Leu Arg Ala Lys Leu Val Met Met Gly Met Phe Lys
        115                 120                 125

Ser Ser Lys Met Tyr Tyr Ala Tyr Lys Cys Ser Phe Asn Met Cys Met
    130                 135                 140

Trp Leu Val Ala Val Ala Met Val Tyr Tyr Ser Asp Ser Leu Ala Met
145                 150                 155                 160

His Ile Gly Ser Ala Leu Leu Leu Gly Leu Phe Trp Gln Gln Cys Gly
                165                 170                 175

Trp Leu Ala His Asp Phe Leu His His Gln Val Phe Lys Gln Arg Lys
            180                 185                 190

Tyr Gly Asp Leu Val Gly Ile Phe Trp Gly Asp Leu Met Gln Gly Phe
        195                 200                 205

Ser Met Gln Trp Trp Lys Asn Lys His Asn Gly His His Ala Val Pro
    210                 215                 220

Asn Leu His Asn Ser Ser Leu Asp Ser Gln Asp Gly Asp Pro Asp Ile
225                 230                 235                 240

Asp Thr Met Pro Leu Leu Ala Trp Ser Leu Lys Gln Ala Gln Ser Phe
                245                 250                 255

Arg Glu Ile Asn Lys Gly Lys Asp Ser Thr Phe Val Lys Tyr Ala Ile
            260                 265                 270

Lys Phe Gln Ala Phe Thr Tyr Phe Pro Ile Leu Leu Leu Ala Arg Ile
        275                 280                 285

Ser Trp Leu Asn Glu Ser Phe Lys Thr Ala Phe Gly Leu Gly Ala Ala
    290                 295                 300

Ser Glu Asn Ala Lys Leu Glu Leu Glu Lys Arg Gly Leu Gln Tyr Pro
305                 310                 315                 320

```
Leu Leu Glu Lys Leu Gly Ile Thr Leu His Tyr Thr Trp Met Phe Val
            325                 330                 335

Leu Ser Ser Gly Phe Gly Arg Trp Ser Leu Pro Tyr Ser Ile Met Tyr
        340                 345                 350

Phe Phe Thr Ala Thr Cys Ser Ser Gly Leu Phe Leu Ala Leu Val Phe
            355                 360                 365

Gly Leu Gly His Asn Gly Met Ser Val Tyr Asp Ala Thr Thr Arg Pro
370                 375                 380

Asp Phe Trp Gln Leu Gln Val Thr Thr Thr Arg Asn Ile Ile Gly Gly
385                 390                 395                 400

His Gly Ile Pro Gln Phe Phe Val Asp Trp Phe Cys Gly Gly Leu Gln
                405                 410                 415

Tyr Gln Val Asp His His Leu Phe Pro Met Met Pro Arg Asn Asn Ile
                420                 425                 430

Ala Lys Cys His Lys Leu Val Glu Ser Phe Cys Lys Glu Trp Gly Val
                435                 440                 445

Lys Tyr His Glu Ala Asp Met Trp Asp Gly Thr Val Glu Val Leu Gln
450                 455                 460

His Leu Ser Lys Val Ser Asp Asp Phe Leu Val Glu Met Val Lys Asp
465                 470                 475                 480

Phe Pro Ala Met

<210> SEQ ID NO 49
<211> LENGTH: 449
<212> TYPE: PRT
<213> ORGANISM: Mantoniella squamata

<400> SEQUENCE: 49

Met Cys Pro Pro Lys Glu Ser Thr Arg Lys Asn Ala Gly Gly Pro Leu
1               5                   10                  15

Thr Arg Gly Lys Leu Ser Ala Asp Leu Ala Lys Leu Glu Pro His Lys
            20                  25                  30

Leu Ala Gln Thr Phe Asp Thr Arg Trp Val Arg Val Gly Asp Val Glu
        35                  40                  45

Tyr Asp Val Thr Asn Phe Lys His Pro Gly Gly Ser Val Ile Phe Tyr
    50                  55                  60

Met Leu Ser Asn Thr Gly Ala Asp Ala Thr Glu Ala Phe Asn Glu Phe
65                  70                  75                  80

His Met Arg Ser Pro Lys Ala Trp Lys Met Leu Lys Ala Leu Pro Asn
                85                  90                  95

Arg Pro Ala Glu Thr Pro Arg Ser Gln Asp Pro Asp Gly Pro Met Leu
            100                 105                 110

Glu Asp Phe Ala Lys Trp Arg Ala Gln Leu Glu Lys Glu Gly Phe Phe
        115                 120                 125

Lys Pro Ser Ile Ala His Val Ala Tyr Arg Ile Ala Glu Leu Ala Ala
    130                 135                 140

Met Phe Ala Leu Gly Cys Tyr Ile Met Ser Leu Gly Tyr Pro Val Val
145                 150                 155                 160

Ala Ser Ile Val Phe Gly Ala Phe Phe Gly Ala Arg Cys Gly Trp Val
                165                 170                 175

Gln His Glu Gly Gly His Asn Ser Leu Thr Gly Asn Ile Trp Leu Asp
            180                 185                 190

Lys Arg Ile Gln Ala Ala Thr Cys Gly Phe Gly Leu Ser Thr Ser Gly
        195                 200                 205
```

Asp Met Trp Asn Gln Met His Asn Lys His His Ala Thr Pro Gln Lys
    210                 215                 220

Val Arg His Asp Met Asp Leu Asp Thr Thr Pro Ala Val Ala Phe Phe
225                 230                 235                 240

Lys Thr Ala Val Glu Asp Asn Arg Pro Arg Gly Phe Ser Arg Ala Trp
                245                 250                 255

Ser Arg Ala Gln Ala Trp Thr Phe Val Pro Val Thr Ser Gly Leu Leu
            260                 265                 270

Val Gln Met Phe Trp Ile Tyr Val Leu His Pro Arg Gln Val Ala Arg
        275                 280                 285

Lys Lys Asn Tyr Glu Glu Ala Ser Trp Met Ile Leu Ser His Val Leu
290                 295                 300

Arg Thr Ala Thr Ile Lys Tyr Ala Gly Gly Tyr Ser Trp Pro Val Ala
305                 310                 315                 320

Tyr Leu Trp Phe Ser Phe Gly Asn Trp Ile Ala Tyr Met Tyr Leu Phe
                325                 330                 335

Ala His Phe Ser Thr Ser His Thr His Leu Glu Val Val Pro Ser Asp
            340                 345                 350

Lys His Ile Ser Trp Val Asn Tyr Ala Val Asp His Thr Val Asp Ile
        355                 360                 365

Asp Pro Ser Lys Gly Tyr Val Asn Trp Leu Met Gly Tyr Leu Asn Cys
370                 375                 380

Gln Val Ile His His Leu Phe Pro Asp Met Pro Gln Phe Arg Gln Pro
385                 390                 395                 400

Glu Val Ser Arg Arg Phe Val Ala Phe Ala Lys Lys Trp Asn Leu Asn
                405                 410                 415

Tyr Lys Val Leu Thr Tyr Tyr Gly Ala Trp Lys Ala Thr Phe Thr Asn
            420                 425                 430

Leu Asp Thr Val Gly Gln His Tyr Tyr Lys His Gly Lys Ala His Ala
        435                 440                 445

His

<210> SEQ ID NO 50
<211> LENGTH: 456
<212> TYPE: PRT
<213> ORGANISM: Ostreococcus tauri

<400> SEQUENCE: 50

Met Cys Val Glu Thr Glu Asn Asn Asp Gly Ile Pro Thr Val Glu Ile
1               5                   10                  15

Ala Phe Asp Gly Glu Arg Glu Arg Ala Glu Ala Asn Val Lys Leu Ser
            20                  25                  30

Ala Glu Lys Met Glu Pro Ala Ala Leu Ala Lys Thr Phe Ala Arg Arg
        35                  40                  45

Tyr Val Val Ile Glu Gly Val Glu Tyr Asp Val Thr Asp Phe Lys His
    50                  55                  60

Pro Gly Gly Thr Val Ile Phe Tyr Ala Leu Ser Asn Thr Gly Ala Asp
65                  70                  75                  80

Ala Thr Glu Ala Phe Lys Glu Phe His His Arg Ser Arg Lys Ala Arg
                85                  90                  95

Lys Ala Leu Ala Ala Leu Pro Ser Arg Pro Ala Lys Thr Ala Lys Val
            100                 105                 110

Asp Asp Ala Glu Met Leu Gln Asp Phe Ala Lys Trp Arg Lys Glu Leu
        115                 120                 125

```
Glu Arg Asp Gly Phe Phe Lys Pro Ser Pro Ala His Val Ala Tyr Arg
130                 135                 140

Phe Ala Glu Leu Ala Ala Met Tyr Ala Leu Gly Thr Tyr Leu Met Tyr
145                 150                 155                 160

Ala Arg Tyr Val Ser Ser Val Leu Val Tyr Ala Cys Phe Phe Gly
        165                 170                 175

Ala Arg Cys Gly Trp Val Gln His Glu Gly His Ser Ser Leu Thr
        180                 185                 190

Gly Asn Ile Trp Trp Asp Lys Arg Ile Gln Ala Phe Thr Ala Gly Phe
        195                 200                 205

Gly Leu Ala Gly Ser Gly Asp Met Trp Asn Ser Met His Asn Lys His
        210                 215                 220

His Ala Thr Pro Gln Lys Val Arg His Asp Met Asp Leu Asp Thr Thr
225                 230                 235                 240

Pro Ala Val Ala Phe Phe Asn Thr Ala Val Glu Asp Asn Arg Pro Arg
                245                 250                 255

Gly Phe Ser Lys Tyr Trp Leu Arg Leu Gln Ala Trp Thr Phe Ile Pro
            260                 265                 270

Val Thr Ser Gly Leu Val Leu Leu Phe Trp Met Phe Phe Leu His Pro
        275                 280                 285

Ser Lys Ala Leu Lys Gly Gly Lys Tyr Glu Glu Leu Val Trp Met Leu
290                 295                 300

Ala Ala His Val Ile Arg Thr Trp Thr Ile Lys Ala Val Thr Gly Phe
305                 310                 315                 320

Thr Ala Met Gln Ser Tyr Gly Leu Phe Leu Ala Thr Ser Trp Val Ser
                325                 330                 335

Gly Cys Tyr Leu Phe Ala His Phe Ser Thr Ser His Thr His Leu Asp
            340                 345                 350

Val Val Pro Ala Asp Glu His Leu Ser Trp Val Arg Tyr Ala Val Asp
        355                 360                 365

His Thr Ile Asp Ile Asp Pro Ser Gln Gly Trp Val Asn Trp Leu Met
370                 375                 380

Gly Tyr Leu Asn Cys Gln Val Ile His His Leu Phe Pro Ser Met Pro
385                 390                 395                 400

Gln Phe Arg Gln Pro Glu Val Ser Arg Arg Phe Val Ala Phe Ala Lys
                405                 410                 415

Lys Trp Asn Leu Asn Tyr Lys Val Met Thr Tyr Tyr Ala Gly Ala Trp Lys
            420                 425                 430

Ala Thr Leu Gly Asn Leu Asp Asn Val Gly Lys His Tyr Tyr Val His
        435                 440                 445

Gly Gln His Ser Gly Lys Thr Ala
    450                 455

<210> SEQ ID NO 51
<211> LENGTH: 482
<212> TYPE: PRT
<213> ORGANISM: Mantoniella squamata

<400> SEQUENCE: 51

Met Pro Pro Arg Glu Thr Thr Pro Ser Val Asp Pro Val Met
1               5                   10                  15

Asp Arg Ile Thr Ser Leu Thr Gly Gly Ala Gly Ala Gly Val Pro Arg
            20                  25                  30

Lys Tyr Thr Thr Ala Asp Val Glu Lys His Ser Thr Pro Asp Asp Cys
        35                  40                  45
```

```
Trp Leu Ile Val His Gly Lys Val Tyr Asp Val Thr Ser Phe Val Pro
 50                  55                  60

Arg His Pro Gly Gly Asn Met Ile Trp Val Lys Ala Gly Gly Asp Cys
 65                  70                  75                  80

Thr Gln Leu Phe Asp Ser Tyr His Pro Ile Lys Thr Gln Ala Val Leu
                 85                  90                  95

Asp Lys Tyr Tyr Ile Gly Glu Val Gln Arg Val Ser Gly Asp Glu Lys
                100                 105                 110

Lys Ile Ile Glu Tyr Asn Asp Asp Met Lys Lys Gly Lys Phe Tyr Met
            115                 120                 125

Asp Cys Lys Val Ala Val Glu Lys Tyr Phe Lys Asp Thr Lys Gln Asp
130                 135                 140

Pro Arg Val His Val Glu Met Tyr Val Lys Thr Phe Val Ile Leu Ala
145                 150                 155                 160

Gly Val Ala Val Cys His Tyr Cys Ser Phe Phe Leu Thr Ser Ser Phe
                165                 170                 175

Leu Val Ser Ala Val Phe Ala Ala Leu His Gly Met Trp Lys Ala Glu
            180                 185                 190

Val Gly Val Ser Ile Gln His Asp Ala Asn His Gly Ala Tyr Gly Lys
    195                 200                 205

Ser Arg Gly Phe Leu His Ala Met Gln Leu Thr Leu Asp Val Val Gly
210                 215                 220

Ala Ser Ser Phe Met Trp Arg Gln Gln His Val Val Gly His His Ala
225                 230                 235                 240

Tyr Thr Asn Val Glu Gly Val Asp Pro Asp Ile Arg Cys Ala Pro Glu
                245                 250                 255

Lys Asp Ile Arg Arg Val Asn Glu His Gln Pro His Glu Ser Tyr His
            260                 265                 270

Pro Leu Gln His Val Tyr Leu Phe Phe Ala Tyr Gly Leu Leu Ser Phe
    275                 280                 285

Lys Ser Cys Phe Ala Asp Asp Phe Asn Ala Trp Ala Ser Gly Arg Ile
290                 295                 300

Gly Trp Val Lys Val Ala Lys Phe Thr Arg Gly Glu Ala Val Ser Phe
305                 310                 315                 320

Trp Gly Ser Lys Val Leu Trp Ala Phe Tyr Tyr Leu Tyr Leu Pro Ala
                325                 330                 335

Thr Tyr Ser Pro His Ser Gly Leu Arg Ile Val Ala Leu Val Thr Ile
            340                 345                 350

Thr Glu Val Ile Thr Gly Trp Leu Leu Ala Phe Met Phe Gln Val Ala
    355                 360                 365

His Val Val Gly Asp Val Arg Phe Phe Lys Leu Ser Glu Glu Gly Lys
    370                 375                 380

Leu Asn Leu Gly Trp Gly Glu Ser Gln Leu Tyr Ser Ser Ala Asp Phe
385                 390                 395                 400

Ala His Gly Ser Lys Phe Trp Met His Phe Ser Gly Gly Leu Asn Tyr
                405                 410                 415

Gln Val Ala His His Leu Phe Pro Gly Val Cys His Cys His Tyr Pro
            420                 425                 430

Ala Ile Ala Pro Ile Ile Met Lys Val Ala Lys Glu Tyr Gly Leu Glu
    435                 440                 445

Tyr Ala Val Tyr Pro Thr Phe Trp Ser Ala Leu Ser Ala His Phe Thr
450                 455                 460
```

```
His Leu Lys Asn Val Gly Gln Lys Thr Tyr Val Pro Ser Leu Gln Thr
465                 470                 475                 480

Ile Gly

<210> SEQ ID NO 52
<211> LENGTH: 491
<212> TYPE: PRT
<213> ORGANISM: Ostreococcus tauri

<400> SEQUENCE: 52

Met Gly Thr Thr Ala Arg Asp Ala Gly Ala Val Thr Thr Arg Ala Arg
1               5                   10                  15

Arg Arg Gly Thr Gly Ala Thr Ser Glu Ala Ser Arg Val Val His Ala
            20                  25                  30

Val Asp Ala Asp Ala Arg Thr Tyr Thr Ala Ala Glu Val Ala Thr His
        35                  40                  45

Ala Arg Ala Asp Asp Cys Trp Val Ile Val Arg Gly Gly Val Tyr Asp
    50                  55                  60

Val Thr Ala Phe Val Pro Arg His Pro Gly Gly Asn Met Ile Tyr Val
65                  70                  75                  80

Lys Ala Gly Gly Glu Cys Thr Ala Leu Phe Asp Ser Tyr His Pro Glu
                85                  90                  95

Lys Ala Arg Gly Val Leu Glu Lys Tyr Arg Ile Gly Asp Leu Thr Arg
            100                 105                 110

Glu Glu Gly Ser Ala Ala Asp Gly Asp Ile Val Glu Tyr Ala Lys Asp
        115                 120                 125

Asp Leu Lys Asp Gly Ala Phe Phe Ala Asp Cys Lys Ala Gly Ala Ala
    130                 135                 140

Lys Tyr Phe Lys Glu Asn Lys Leu Asp Pro Arg Val His Trp Glu Met
145                 150                 155                 160

Tyr Ala Lys Thr Ala Ala Ile Leu Val Gly Ile Val Val Gly His Tyr
                165                 170                 175

Tyr Ser Phe Phe Ala Pro Gly Val Ser Phe Gly Ala Ala Leu Ala Phe
            180                 185                 190

Ala Ala Leu His Gly Thr Cys Lys Ala Glu Val Gly Val Ser Ile Gln
        195                 200                 205

His Asp Ala Asn His Gly Ala Tyr Gly Asn Ser Arg Thr Trp Leu His
    210                 215                 220

Ala Met Gln Leu Thr Leu Asp Val Val Gly Ala Ser Ser Phe Met Trp
225                 230                 235                 240

Lys Gln Gln His Val Ala Gly His His Ala Tyr Thr Asn Val Glu Gly
                245                 250                 255

Ile Asp Pro Asp Ile Arg Cys Ser Glu Lys Asp Ile Arg Arg Val Asn
            260                 265                 270

Glu His Gln Pro His Glu Pro Tyr His Val Phe Gln His Val Tyr Leu
        275                 280                 285

Ala Phe Met Tyr Gly Leu Leu Ser Leu Lys Ser Cys Phe Val Asp Asp
    290                 295                 300

Phe Asn Ala Tyr Phe Ser Gly Arg Ile Gly Trp Val Lys Val Met Lys
305                 310                 315                 320

Phe Thr Arg Gly Glu Ala Ile Ala Phe Trp Gly Thr Lys Leu Leu Trp
                325                 330                 335

Ala Ala Tyr Tyr Leu Ala Leu Pro Leu Lys Met Ser His Arg Pro Leu
            340                 345                 350
```

```
Gly Glu Leu Leu Ala Leu Trp Ala Val Thr Glu Phe Val Thr Gly Trp
            355                 360                 365

Leu Leu Ala Phe Met Phe Gln Val Ala His Val Val Gly Glu Val His
    370                 375                 380

Phe Phe Thr Leu Asp Ala Lys Asn Arg Val Asn Leu Gly Trp Gly Glu
385                 390                 395                 400

Ala Gln Leu Met Ser Ser Ala Asp Phe Ala His Gly Ser Lys Phe Trp
                405                 410                 415

Thr His Phe Ser Gly Gly Leu Asn Tyr Gln Val Val His Leu Phe
                420                 425                 430

Pro Gly Val Cys His Val His Tyr Pro Ala Leu Ala Pro Ile Ile Lys
                435                 440                 445

Ala Ala Ala Glu Lys His Gly Leu His Tyr Gln Ile Tyr Pro Thr Phe
450                 455                 460

Trp Ser Ala Leu Arg Ala His Phe Arg His Leu Ala Asn Val Gly Arg
465                 470                 475                 480

Ala Ala Tyr Val Pro Ser Leu Gln Thr Val Gly
                485                 490

<210> SEQ ID NO 53
<211> LENGTH: 484
<212> TYPE: PRT
<213> ORGANISM: Marchantia polymorpha

<400> SEQUENCE: 53

Met Pro Pro His Ala Pro Asp Ser Thr Gly Leu Gly Pro Glu Val Phe
1               5                   10                  15

Arg Leu Pro Asp Asp Ala Ile Pro Ala Gln Asp Arg Arg Ser Thr Gln
                20                  25                  30

Lys Lys Tyr Ser Leu Ser Asp Val Ser Lys His Asn Thr Pro Asn Asp
            35                  40                  45

Cys Trp Leu Val Ile Trp Gly Lys Val Tyr Asp Val Thr Ser Trp Val
    50                  55                  60

Lys Val His Pro Gly Gly Ser Leu Ile Phe Val Lys Ala Gly Gln Asp
65                  70                  75                  80

Ser Thr Gln Leu Phe Asp Ser Tyr His Pro Leu Tyr Val Arg Lys Leu
                85                  90                  95

Leu Ala Gln Phe Cys Ile Gly Glu Leu Gln Thr Ser Ala Gly Asp Glu
            100                 105                 110

Lys Phe Lys Ser Ser Thr Leu Glu Tyr Ala Gly Glu Glu His Glu Val
        115                 120                 125

Phe Tyr His Thr Leu Lys Gln Arg Val Glu Thr Tyr Phe Arg Lys Gln
    130                 135                 140

Lys Ile Asn Pro Arg Tyr His Pro Gln Met Leu Val Lys Ser Ala Val
145                 150                 155                 160

Ile Ile Gly Thr Leu Leu Cys Tyr Phe Gly Phe Phe Trp Ser
                165                 170                 175

Gln Asn Val Leu Leu Ser Met Phe Leu Ala Ser Ile Met Gly Phe Cys
            180                 185                 190

Thr Ala Glu Val Gly Met Ser Ile Met His Asp Gly Asn His Gly Ser
        195                 200                 205

Tyr Thr Gln Ser Thr Leu Leu Gly Tyr Val Met Gly Ala Thr Leu Asp
    210                 215                 220

Leu Val Gly Ala Ser Ser Phe Met Trp Arg Gln Gln His Val Ala Gly
225                 230                 235                 240
```

```
His His Ser Phe Thr Asn Ile Asp His Tyr Asp Pro Asp Ile Arg Val
                245                 250                 255

Lys Asp Pro Asp Leu Arg Arg Val Thr Ser Gln Gln Pro Arg Arg Trp
        260                 265                 270

Phe His Glu Tyr Gln His Ile Tyr Leu Gly Val Leu Tyr Gly Val Leu
            275                 280                 285

Ala Leu Lys Ser Val Leu Ile Asp Asp Phe Ser Ala Phe Phe Ser Gly
        290                 295                 300

Ala Ile Gly Pro Val Lys Ile Ala Gln Met Thr Pro Leu Glu Met Gly
305                 310                 315                 320

Val Phe Trp Gly Gly Lys Val Val Tyr Ala Leu Tyr Met Phe Leu Leu
                325                 330                 335

Pro Met Met Tyr Gly Gln Tyr Asn Ile Leu Thr Phe Ile Gly Leu Tyr
            340                 345                 350

Ile Leu Ser Gln Leu Val Ala Gly Trp Thr Leu Ala Leu Phe Phe Gln
        355                 360                 365

Val Ala His Val Val Asp Asp Ala Val Phe Pro Val Ala Glu Thr Asp
            370                 375                 380

Gly Gly Lys Ala Lys Ile Pro Ser Gly Trp Ala Glu Met Gln Val Arg
385                 390                 395                 400

Thr Thr Thr Asn Phe Ser Ser Arg Ser Met Phe Trp Thr His Ile Ser
                405                 410                 415

Gly Gly Leu Asn His Gln Ile Glu His His Leu Phe Pro Gly Val Cys
            420                 425                 430

His Val His Tyr Pro Ser Ile Gln Pro Ile Val Lys Ala Thr Cys Asp
        435                 440                 445

Glu Phe Asn Val Pro Tyr Thr Ser Tyr Pro Thr Phe Trp Ala Ala Leu
    450                 455                 460

Arg Ala His Phe Gln His Leu Lys Asn Val Gly Leu Gln Asp Gly Leu
465                 470                 475                 480

Arg Leu Asp Gly

<210> SEQ ID NO 54
<211> LENGTH: 467
<212> TYPE: PRT
<213> ORGANISM: Dictyostelium discoideum

<400> SEQUENCE: 54

Met Met Glu Thr Asn Asn Glu Asn Lys Glu Lys Leu Lys Leu Tyr Thr
1               5                   10                  15

Trp Asp Glu Val Ser Lys His Asn Gln Lys Asn Asp Leu Trp Ile Ile
            20                  25                  30

Val Asp Gly Lys Val Tyr Asn Ile Thr Lys Trp Val Pro Leu His Pro
        35                  40                  45

Gly Gly Glu Asp Ile Leu Leu Leu Ser Ala Gly Arg Asp Ala Thr Asn
    50                  55                  60

Leu Phe Glu Ser Tyr His Pro Met Thr Asp Lys His Tyr Ser Leu Ile
65                  70                  75                  80

Lys Gln Tyr Glu Ile Gly Tyr Ile Ser Ser Tyr Glu Pro Lys Tyr
            85                  90                  95

Val Glu Lys Ser Glu Phe Tyr Ser Thr Leu Gln Arg Val Arg Lys
        100                 105                 110

His Phe Gln Thr Ser Ser Gln Asp Pro Lys Val Ser Val Gly Val Phe
            115                 120                 125
```

Thr Arg Met Val Leu Ile Tyr Leu Phe Leu Phe Val Thr Tyr Tyr Leu
130                 135                 140

Ser Gln Phe Ser Thr Asp Arg Phe Trp Leu Asn Cys Ile Phe Ala Val
145                 150                 155                 160

Leu Tyr Gly Val Ala Asn Ser Leu Phe Gly Leu His Thr Met His Asp
            165                 170                 175

Ala Cys His Thr Ala Ile Thr His Asn Pro Met Thr Trp Lys Ile Leu
            180                 185                 190

Gly Ala Thr Phe Asp Leu Phe Ala Gly Ala Ser Phe Tyr Ala Trp Cys
            195                 200                 205

His Gln His Val Ile Gly His His Leu Tyr Thr Asn Val Arg Asn Ala
210                 215                 220

Asp Pro Asp Leu Gly Gln Gly Glu Ile Asp Phe Arg Val Val Thr Pro
225                 230                 235                 240

Tyr Gln Ala Arg Ser Trp Tyr His Lys Tyr Gln His Ile Tyr Ala Pro
            245                 250                 255

Ile Leu Tyr Gly Val Tyr Ala Leu Lys Tyr Arg Ile Gln Asp His Glu
            260                 265                 270

Ile Phe Thr Lys Lys Ser Asn Gly Ala Ile Arg Tyr Ser Pro Ile Ser
            275                 280                 285

Thr Ile Asp Thr Ala Ile Phe Ile Leu Gly Lys Leu Val Phe Ile Ile
290                 295                 300

Ser Arg Phe Ile Leu Pro Leu Ile Tyr Asn His Ser Phe Ser His Leu
305                 310                 315                 320

Ile Cys Phe Phe Leu Ile Ser Glu Leu Val Leu Gly Trp Tyr Leu Ala
            325                 330                 335

Ile Ser Phe Gln Val Ser His Val Val Glu Asp Leu Gln Phe Met Ala
            340                 345                 350

Thr Pro Glu Ile Phe Asp Gly Ala Asp His Pro Leu Pro Thr Thr Phe
            355                 360                 365

Asn Gln Asp Trp Ala Ile Leu Gln Val Lys Thr Thr Gln Asp Tyr Ala
370                 375                 380

Gln Asp Ser Val Leu Ser Thr Phe Phe Ser Gly Gly Leu Asn Leu Gln
385                 390                 395                 400

Val Ile His His Cys Phe Pro Thr Ile Ala Gln Asp Tyr Tyr Pro Gln
            405                 410                 415

Ile Val Pro Ile Leu Lys Glu Val Cys Lys Glu Tyr Asn Val Thr Tyr
            420                 425                 430

His Tyr Lys Pro Thr Phe Thr Glu Ala Ile Lys Ser His Ile Asn Tyr
            435                 440                 445

Leu Tyr Lys Met Gly Asn Asp Pro Asp Tyr Val Arg Lys Pro Val Asn
450                 455                 460

Lys Asn Asp
465

<210> SEQ ID NO 55
<211> LENGTH: 446
<212> TYPE: PRT
<213> ORGANISM: Mortierella alpina

<400> SEQUENCE: 55

Met Gly Thr Asp Gln Gly Lys Thr Phe Thr Trp Glu Glu Leu Ala Ala
1               5                   10                  15

His Asn Thr Lys Asp Asp Leu Leu Leu Ala Ile Arg Gly Arg Val Tyr
            20                  25                  30

-continued

```
Asp Val Thr Lys Phe Leu Ser Arg His Pro Gly Val Asp Thr Leu
         35                  40                  45
Leu Leu Gly Ala Gly Arg Asp Val Thr Pro Val Phe Glu Met Tyr His
 50                  55                  60
Ala Phe Gly Ala Ala Asp Ala Ile Met Lys Lys Tyr Tyr Val Gly Thr
 65                  70                  75                  80
Leu Val Ser Asn Glu Leu Pro Ile Phe Pro Glu Pro Thr Val Phe His
                 85                  90                  95
Lys Thr Ile Lys Thr Arg Val Glu Gly Tyr Phe Thr Asp Arg Asn Ile
                100                 105                 110
Asp Pro Lys Asn Arg Pro Glu Ile Trp Gly Arg Tyr Ala Leu Ile Phe
                115                 120                 125
Gly Ser Leu Ile Ala Ser Tyr Tyr Ala Gln Leu Phe Val Pro Phe Val
                130                 135                 140
Val Glu Arg Thr Trp Leu Gln Val Val Phe Ala Ile Ile Met Gly Phe
145                 150                 155                 160
Ala Cys Ala Gln Val Gly Leu Asn Pro Leu His Asp Ala Ser His Phe
                165                 170                 175
Ser Val Thr His Asn Pro Thr Val Trp Lys Ile Leu Gly Ala Thr His
                180                 185                 190
Asp Phe Phe Asn Gly Ala Ser Tyr Leu Val Trp Met Tyr Gln His Met
                195                 200                 205
Leu Gly His His Pro Tyr Thr Asn Ile Ala Gly Ala Asp Pro Asp Val
                210                 215                 220
Ser Thr Ser Glu Pro Asp Val Arg Arg Ile Lys Pro Asn Gln Lys Trp
225                 230                 235                 240
Phe Val Asn His Ile Asn Gln His Met Phe Val Pro Phe Leu Tyr Gly
                245                 250                 255
Leu Leu Ala Phe Lys Val Arg Ile Gln Asp Ile Asn Ile Leu Tyr Phe
                260                 265                 270
Val Lys Thr Asn Asp Ala Ile Arg Val Asn Pro Ile Ser Thr Trp His
                275                 280                 285
Thr Val Met Phe Trp Gly Gly Lys Ala Phe Phe Val Trp Tyr Arg Leu
                290                 295                 300
Ile Val Pro Leu Gln Tyr Leu Pro Leu Gly Lys Val Leu Leu Leu Phe
305                 310                 315                 320
Thr Val Ala Asp Met Val Ser Ser Tyr Trp Leu Ala Leu Thr Phe Gln
                325                 330                 335
Ala Asn His Val Val Glu Glu Val Gln Trp Pro Leu Pro Asp Glu Asn
                340                 345                 350
Gly Ile Ile Gln Lys Asp Trp Ala Ala Met Gln Val Glu Thr Thr Gln
                355                 360                 365
Asp Tyr Ala His Asp Ser His Leu Trp Thr Ser Ile Thr Gly Ser Leu
                370                 375                 380
Asn Tyr Gln Ala Val His His Leu Phe Pro Asn Val Ser Gln His His
385                 390                 395                 400
Tyr Pro Asp Ile Leu Ala Ile Ile Lys Asn Thr Cys Ser Glu Tyr Lys
                405                 410                 415
Val Pro Tyr Leu Val Lys Asp Thr Phe Trp Gln Ala Phe Ala Ser His
                420                 425                 430
Leu Glu His Leu Arg Val Leu Gly Leu Arg Pro Lys Glu Glu
                435                 440                 445
```

```
<210> SEQ ID NO 56
<211> LENGTH: 469
<212> TYPE: PRT
<213> ORGANISM: Phaeodactylum tricornutum

<400> SEQUENCE: 56
```

| | | | | | | | | | | | | | | |
|---|---|---|---|---|---|---|---|---|---|---|---|---|---|---|
| Met | Ala | Pro | Asp | Ala | Asp | Lys | Leu | Arg | Gln | Arg | Gln | Thr | Thr | Ala | Val |
| 1 | | | | 5 | | | | | 10 | | | | | 15 | |
| Ala | Lys | His | Asn | Ala | Ala | Thr | Ile | Ser | Thr | Gln | Glu | Arg | Leu | Cys | Ser |
| | | | 20 | | | | | 25 | | | | | 30 | | |
| Leu | Ser | Ser | Leu | Lys | Gly | Glu | Glu | Val | Cys | Ile | Asp | Gly | Ile | Ile | Tyr |
| | | 35 | | | | | 40 | | | | | 45 | | | |
| Asp | Leu | Gln | Ser | Phe | Asp | His | Pro | Gly | Gly | Glu | Thr | Ile | Lys | Met | Phe |
| 50 | | | | | 55 | | | | | 60 | | | | | |
| Gly | Gly | Asn | Asp | Val | Thr | Val | Gln | Tyr | Lys | Met | Ile | His | Pro | Tyr | His |
| 65 | | | | 70 | | | | | 75 | | | | | 80 | |
| Thr | Glu | Lys | His | Leu | Glu | Lys | Met | Lys | Arg | Val | Gly | Lys | Val | Thr | Asp |
| | | | | 85 | | | | | 90 | | | | | 95 | |
| Phe | Val | Cys | Glu | Tyr | Lys | Phe | Asp | Thr | Glu | Phe | Glu | Arg | Glu | Ile | Lys |
| | | | 100 | | | | | 105 | | | | | 110 | | |
| Arg | Glu | Val | Phe | Lys | Ile | Val | Arg | Arg | Gly | Lys | Asp | Phe | Gly | Thr | Leu |
| | | | 115 | | | | | 120 | | | | | 125 | | |
| Gly | Trp | Phe | Phe | Arg | Ala | Phe | Cys | Tyr | Ile | Ala | Ile | Phe | Phe | Tyr | Leu |
| | 130 | | | | | 135 | | | | | 140 | | | | |
| Gln | Tyr | His | Trp | Val | Thr | Thr | Gly | Thr | Ser | Trp | Leu | Leu | Ala | Val | Ala |
| 145 | | | | | 150 | | | | | 155 | | | | | 160 |
| Tyr | Gly | Ile | Ser | Gln | Ala | Met | Ile | Gly | Met | Asn | Val | Gln | His | Asp | Ala |
| | | | | 165 | | | | | 170 | | | | | 175 | |
| Asn | His | Gly | Ala | Thr | Ser | Lys | Arg | Pro | Trp | Val | Asn | Asp | Met | Leu | Gly |
| | | | 180 | | | | | 185 | | | | | 190 | | |
| Leu | Gly | Ala | Asp | Phe | Ile | Gly | Gly | Ser | Lys | Trp | Leu | Trp | Gln | Glu | Gln |
| | | | 195 | | | | | 200 | | | | | 205 | | |
| His | Trp | Thr | His | His | Ala | Tyr | Thr | Asn | His | Ala | Glu | Met | Asp | Pro | Asp |
| | 210 | | | | | 215 | | | | | 220 | | | | |
| Ser | Phe | Gly | Ala | Glu | Pro | Met | Leu | Leu | Phe | Asn | Asp | Tyr | Pro | Leu | Asp |
| 225 | | | | | 230 | | | | | 235 | | | | | 240 |
| His | Pro | Ala | Arg | Thr | Trp | Leu | His | Arg | Phe | Gln | Ala | Phe | Phe | Tyr | Met |
| | | | | 245 | | | | | 250 | | | | | 255 | |
| Pro | Val | Leu | Ala | Gly | Tyr | Trp | Leu | Ser | Ala | Val | Phe | Asn | Pro | Gln | Ile |
| | | | 260 | | | | | 265 | | | | | 270 | | |
| Leu | Asp | Leu | Gln | Gln | Arg | Gly | Ala | Leu | Ser | Val | Gly | Ile | Arg | Leu | Asp |
| | | 275 | | | | | 280 | | | | | 285 | | | |
| Asn | Ala | Phe | Ile | His | Ser | Arg | Arg | Lys | Tyr | Ala | Val | Phe | Trp | Arg | Ala |
| | 290 | | | | | 295 | | | | | 300 | | | | |
| Val | Tyr | Ile | Ala | Val | Asn | Val | Ile | Ala | Pro | Phe | Tyr | Thr | Asn | Ser | Gly |
| 305 | | | | | 310 | | | | | 315 | | | | | 320 |
| Leu | Glu | Trp | Ser | Trp | Arg | Val | Phe | Gly | Asn | Ile | Met | Leu | Met | Gly | Val |
| | | | | 325 | | | | | 330 | | | | | 335 | |
| Ala | Glu | Ser | Leu | Ala | Leu | Ala | Val | Leu | Phe | Ser | Leu | Ser | His | Asn | Phe |
| | | | 340 | | | | | 345 | | | | | 350 | | |
| Glu | Ser | Ala | Asp | Arg | Asp | Pro | Thr | Ala | Pro | Leu | Lys | Lys | Thr | Gly | Glu |
| | | | 355 | | | | | 360 | | | | | 365 | | |
| Pro | Val | Asp | Trp | Phe | Lys | Thr | Gln | Val | Glu | Thr | Ser | Cys | Thr | Tyr | Gly |
| | 370 | | | | | 375 | | | | | 380 | | | | |

```
Gly Phe Leu Ser Gly Cys Phe Thr Gly Gly Leu Asn Phe Gln Val Glu
385                 390                 395                 400

His His Leu Phe Pro Arg Met Ser Ser Ala Trp Tyr Pro Tyr Ile Ala
                405                 410                 415

Pro Lys Val Arg Glu Ile Cys Ala Lys His Gly Val His Tyr Ala Tyr
            420                 425                 430

Tyr Pro Trp Ile His Gln Asn Phe Leu Ser Thr Val Arg Tyr Met His
        435                 440                 445

Ala Ala Gly Thr Gly Ala Asn Trp Arg Gln Met Ala Arg Glu Asn Pro
450                 455                 460

Leu Thr Gly Arg Ala
465

<210> SEQ ID NO 57
<211> LENGTH: 292
<212> TYPE: PRT
<213> ORGANISM: Ostreococcus tauri

<400> SEQUENCE: 57

Met Ser Gly Leu Arg Ala Pro Asn Phe Leu His Arg Phe Trp Thr Lys
1               5                   10                  15

Trp Asp Tyr Ala Ile Ser Lys Val Val Phe Thr Cys Ala Asp Ser Phe
            20                  25                  30

Gln Trp Asp Ile Gly Pro Val Ser Ser Thr Ala His Leu Pro Ala
        35                  40                  45

Ile Glu Ser Pro Thr Pro Leu Val Thr Ser Leu Leu Phe Tyr Leu Val
50                  55                  60

Thr Val Phe Leu Trp Tyr Gly Arg Leu Thr Arg Ser Ser Asp Lys Lys
65                  70                  75                  80

Ile Arg Glu Pro Thr Trp Leu Arg Arg Phe Ile Ile Cys His Asn Ala
                85                  90                  95

Phe Leu Ile Val Leu Ser Leu Tyr Met Cys Leu Gly Cys Val Ala Gln
            100                 105                 110

Ala Tyr Gln Asn Gly Tyr Thr Leu Trp Gly Asn Glu Phe Lys Ala Thr
        115                 120                 125

Glu Thr Gln Leu Ala Leu Tyr Ile Tyr Ile Phe Tyr Val Ser Lys Ile
130                 135                 140

Tyr Glu Phe Val Asp Thr Tyr Ile Met Leu Leu Lys Asn Asn Leu Arg
145                 150                 155                 160

Gln Val Ser Phe Leu His Ile Tyr His His Ser Thr Ile Ser Phe Ile
                165                 170                 175

Trp Trp Ile Ile Ala Arg Arg Ala Pro Gly Gly Asp Ala Tyr Phe Ser
            180                 185                 190

Ala Ala Leu Asn Ser Trp Val His Val Cys Met Tyr Thr Tyr Tyr Leu
        195                 200                 205

Leu Ser Thr Leu Ile Gly Lys Glu Asp Pro Lys Arg Ser Asn Tyr Leu
210                 215                 220

Trp Trp Gly Arg His Leu Thr Gln Met Gln Met Leu Gln Phe Phe
225                 230                 235                 240

Asn Val Leu Gln Ala Leu Tyr Cys Ala Ser Phe Ser Thr Tyr Pro Lys
                245                 250                 255

Phe Leu Ser Lys Ile Leu Leu Val Tyr Met Met Ser Leu Leu Gly Leu
            260                 265                 270
```

```
Phe Gly His Phe Tyr Tyr Ser Lys His Ile Ala Ala Ala Lys Leu Gln
            275                 280                 285

Lys Lys Gln Gln
    290

<210> SEQ ID NO 58
<211> LENGTH: 290
<212> TYPE: PRT
<213> ORGANISM: Marchantia polymorpha

<400> SEQUENCE: 58

Met Glu Ala Tyr Glu Met Val Asp Ser Phe Val Ser Lys Thr Val Phe
1               5                   10                  15

Glu Thr Leu Gln Arg Leu Arg Gly Gly Val Val Leu Thr Glu Ser Ala
            20                  25                  30

Ile Thr Lys Gly Leu Pro Cys Val Asp Ser Pro Thr Pro Ile Val Leu
        35                  40                  45

Gly Leu Ser Ser Tyr Leu Thr Phe Val Phe Leu Gly Leu Ile Val Ile
    50                  55                  60

Lys Ser Leu Asp Leu Lys Pro Arg Ser Lys Glu Pro Ala Ile Leu Asn
65                  70                  75                  80

Leu Phe Val Ile Phe His Asn Phe Val Cys Phe Ala Leu Ser Leu Tyr
                85                  90                  95

Met Cys Val Gly Ile Val Arg Gln Ala Ile Leu Asn Arg Tyr Ser Leu
            100                 105                 110

Trp Gly Asn Ala Tyr Asn Pro Lys Glu Val Gln Met Gly His Leu Leu
        115                 120                 125

Tyr Ile Phe Tyr Met Ser Lys Tyr Ile Glu Phe Met Asp Thr Val Ile
    130                 135                 140

Met Ile Leu Lys Arg Asn Thr Arg Gln Ile Thr Val Leu His Val Tyr
145                 150                 155                 160

His His Ala Ser Ile Ser Phe Ile Trp Trp Ile Ile Ala Tyr His Ala
                165                 170                 175

Pro Gly Gly Glu Ala Tyr Phe Ser Ala Ala Leu Asn Ser Gly Val His
            180                 185                 190

Val Leu Met Tyr Leu Tyr Tyr Leu Leu Ala Ala Thr Leu Gly Lys Asn
        195                 200                 205

Glu Lys Ala Arg Arg Lys Tyr Leu Trp Trp Gly Lys Tyr Leu Thr Gln
    210                 215                 220

Leu Gln Met Phe Gln Phe Val Leu Asn Met Ile Gln Ala Tyr Tyr Asp
225                 230                 235                 240

Ile Lys Asn Asn Ser Pro Tyr Pro Gln Phe Leu Ile Gln Ile Leu Phe
                245                 250                 255

Tyr Tyr Met Ile Ser Leu Leu Ala Leu Phe Gly Asn Phe Tyr Val His
            260                 265                 270

Lys Tyr Val Ser Ala Pro Ala Lys Pro Ala Lys Ile Lys Ser Lys Lys
        275                 280                 285

Ala Glu
    290

<210> SEQ ID NO 59
<211> LENGTH: 290
<212> TYPE: PRT
<213> ORGANISM: Physcomitrella patens
```

<400> SEQUENCE: 59

Met Glu Val Val Glu Arg Phe Tyr Gly Glu Leu Asp Gly Lys Val Ser
1               5                   10                  15

Gln Gly Val Asn Ala Leu Leu Gly Ser Phe Gly Val Glu Leu Thr Asp
            20                  25                  30

Thr Pro Thr Thr Lys Gly Leu Pro Leu Val Asp Ser Pro Thr Pro Ile
        35                  40                  45

Val Leu Gly Val Ser Val Tyr Leu Thr Ile Val Ile Gly Gly Leu Leu
    50                  55                  60

Trp Ile Lys Ala Arg Asp Leu Lys Pro Arg Ala Ser Glu Pro Phe Leu
65                  70                  75                  80

Leu Gln Ala Leu Val Leu Val His Asn Leu Phe Cys Phe Ala Leu Ser
                85                  90                  95

Leu Tyr Met Cys Val Gly Ile Ala Tyr Gln Ala Ile Thr Trp Arg Tyr
            100                 105                 110

Ser Leu Trp Gly Asn Ala Tyr Asn Pro Lys His Lys Glu Met Ala Ile
        115                 120                 125

Leu Val Tyr Leu Phe Tyr Met Ser Lys Tyr Val Glu Phe Met Asp Thr
    130                 135                 140

Val Ile Met Ile Leu Lys Arg Ser Thr Arg Gln Ile Ser Phe Leu His
145                 150                 155                 160

Val Tyr His His Ser Ser Ile Ser Leu Ile Trp Trp Ala Ile Ala His
                165                 170                 175

His Ala Pro Gly Gly Glu Ala Tyr Trp Ser Ala Ala Leu Asn Ser Gly
            180                 185                 190

Val His Val Leu Met Tyr Ala Tyr Tyr Phe Leu Ala Ala Cys Leu Arg
        195                 200                 205

Ser Ser Pro Lys Leu Lys Asn Lys Tyr Leu Phe Trp Gly Arg Tyr Leu
    210                 215                 220

Thr Gln Phe Gln Met Phe Gln Phe Met Leu Asn Leu Val Gln Ala Tyr
225                 230                 235                 240

Tyr Asp Met Lys Thr Asn Ala Pro Tyr Pro Gln Trp Leu Ile Lys Ile
                245                 250                 255

Leu Phe Tyr Tyr Met Ile Ser Leu Leu Phe Leu Phe Gly Asn Phe Tyr
            260                 265                 270

Val Gln Lys Tyr Ile Lys Pro Ser Asp Gly Lys Gln Lys Gly Ala Lys
        275                 280                 285

Thr Glu
    290

<210> SEQ ID NO 60
<211> LENGTH: 348
<212> TYPE: PRT
<213> ORGANISM: Marchantia polymorpha

<400> SEQUENCE: 60

Met Ala Thr Lys Ser Gly Ser Gly Leu Leu Glu Trp Ile Ala Val Ala
1               5                   10                  15

Ala Lys Met Lys Gln Ala Arg Ser Ser Pro Glu Gly Glu Ile Val Gly
            20                  25                  30

Gly Asn Arg Met Gly Ser Gly Asn Gly Ala Glu Trp Thr Thr Ser Leu
        35                  40                  45

Ile His Ala Phe Leu Asn Ala Thr Asn Gly Lys Ser Gly Gly Ala Ser
    50                  55                  60

```
Lys Val Arg Pro Leu Glu Glu Arg Ile Gly Glu Ala Val Phe Arg Val
 65                  70                  75                  80

Leu Glu Asp Val Val Gly Val Asp Ile Arg Lys Pro Asn Pro Val Thr
                 85                  90                  95

Lys Asp Leu Pro Met Val Glu Ser Pro Val Pro Val Leu Ala Cys Ile
            100                 105                 110

Ser Leu Tyr Leu Leu Val Val Trp Leu Trp Ser Ser His Ile Lys Ala
        115                 120                 125

Ser Gly Gln Lys Pro Arg Lys Glu Asp Pro Leu Ala Leu Arg Cys Leu
    130                 135                 140

Val Ile Ala His Asn Leu Phe Leu Cys Cys Leu Ser Leu Phe Met Cys
145                 150                 155                 160

Val Gly Leu Ile Ala Ala Ala Arg His Tyr Gly Tyr Ser Val Trp Gly
                165                 170                 175

Asn Tyr Tyr Arg Glu Arg Glu Pro Ala Met Asn Leu Leu Ile Tyr Val
            180                 185                 190

Phe Tyr Met Ser Lys Leu Tyr Glu Phe Met Asp Thr Ala Ile Met Leu
        195                 200                 205

Phe Arg Arg Asn Leu Arg Gln Val Thr Tyr Leu His Val Tyr His His
210                 215                 220

Ala Ser Ile Ala Met Ile Trp Trp Ile Ile Cys Tyr Arg Phe Pro Gly
225                 230                 235                 240

Ala Asp Ser Tyr Phe Ser Ala Ala Phe Asn Ser Cys Ile His Val Ala
                245                 250                 255

Met Tyr Leu Tyr Tyr Leu Leu Ala Ala Thr Val Ala Arg Asp Glu Lys
            260                 265                 270

Arg Arg Arg Lys Tyr Leu Phe Trp Gly Lys Tyr Leu Thr Ile Ile Gln
        275                 280                 285

Met Leu Gln Phe Leu Ser Phe Ile Gly Gln Ala Ile Tyr Ala Met Trp
    290                 295                 300

Lys Phe Glu Tyr Tyr Pro Lys Gly Phe Gly Arg Met Leu Phe Phe Tyr
305                 310                 315                 320

Ser Val Ser Leu Leu Ala Phe Phe Gly Asn Phe Phe Val Lys Lys Tyr
                325                 330                 335

Ser Asn Ala Ser Gln Pro Lys Thr Val Lys Val Glu
            340                 345

<210> SEQ ID NO 61
<211> LENGTH: 276
<212> TYPE: PRT
<213> ORGANISM: Thraustochytrium sp. FJN-10

<400> SEQUENCE: 61

Met Asp Val Val Glu Gln Gln Trp Arg Arg Phe Val Asp Ala Val Asp
  1               5                  10                  15

Asn Gly Ile Val Glu Phe Met Glu His Glu Glu Pro Asn Lys Leu Asn
             20                  25                  30

Glu Gly Lys Leu Ser Thr Ser Thr Glu Glu Met Met Ala Leu Ile Val
         35                  40                  45

Gly Tyr Leu Ala Phe Val Val Leu Gly Ser Ala Phe Met Lys Ala Phe
     50                  55                  60

Val Asp Lys Pro Phe Glu Leu Lys Phe Leu Lys Leu Val His Asn Ile
 65                  70                  75                  80

Phe Leu Thr Gly Leu Ser Met Tyr Met Ala Thr Glu Cys Ala Arg Gln
                 85                  90                  95
```

-continued

```
Ala Tyr Leu Gly Gly Tyr Lys Leu Phe Gly Asn Pro Met Glu Lys Gly
            100                 105                 110

Thr Glu Ser His Ala Pro Gly Met Ala Asn Ile Ile Tyr Ile Phe Tyr
        115                 120                 125

Val Ser Lys Phe Leu Glu Phe Leu Asp Thr Val Phe Met Ile Leu Gly
    130                 135                 140

Lys Lys Trp Lys Gln Leu Ser Phe Leu His Val Tyr His His Ala Ser
145                 150                 155                 160

Ile Ser Phe Ile Trp Gly Ile Ile Ala Arg Phe Ala Pro Gly Gly Asp
                165                 170                 175

Ala Tyr Phe Ser Thr Ile Leu Asn Ser Ser Val His Val Val Leu Tyr
            180                 185                 190

Gly Tyr Tyr Ala Ser Thr Thr Leu Gly Tyr Thr Phe Met Arg Pro Leu
        195                 200                 205

Arg Pro Tyr Ile Thr Thr Ile Gln Leu Thr Gln Phe Met Ala Met Val
    210                 215                 220

Val Gln Ser Val Tyr Asp Tyr Tyr Asn Pro Cys Asp Tyr Pro Gln Pro
225                 230                 235                 240

Leu Val Lys Leu Leu Phe Trp Tyr Met Leu Thr Met Leu Gly Leu Phe
                245                 250                 255

Gly Asn Phe Phe Val Gln Gln Tyr Leu Lys Pro Lys Ala Pro Lys Lys
            260                 265                 270

Gln Lys Thr Ile
        275
```

<210> SEQ ID NO 62
<211> LENGTH: 12
<212> TYPE: PRT
<213> ORGANISM: Articifical
<220> FEATURE:
<223> OTHER INFORMATION: Parietochloris incisa;Marchantia polymorpha;
      Ostreococcus tauri;Physcomitrella patens
<220> FEATURE:
<221> NAME/KEY: MISC_FEATURE
<222> LOCATION: (3)..(3)
<223> OTHER INFORMATION: Xaa at position 3 may be any naturally-
      occurring amino acid and up to one amino acid may be absent
<220> FEATURE:
<221> NAME/KEY: MISC_FEATURE
<222> LOCATION: (6)..(7)
<223> OTHER INFORMATION: Xaa at positions 6-7 may be any naturally-
      occurring amino acids and up to two of them may be absent
<220> FEATURE:
<221> NAME/KEY: MISC_FEATURE
<222> LOCATION: (10)..(10)
<223> OTHER INFORMATION: Xaa at position 10 may be any naturally-
      occurring amino acid and up to one amino acid may be absent

<400> SEQUENCE: 62

```
Phe Tyr Xaa Ser Lys Xaa Xaa Glu Phe Xaa Asp Thr
1               5                   10
```

<210> SEQ ID NO 63
<211> LENGTH: 13
<212> TYPE: PRT
<213> ORGANISM: Artificial
<220> FEATURE:
<223> OTHER INFORMATION: Parietochloris incisa;Marchantia polymorpha;
      Ostreococcus tauri;Physcomitrella patens
<220> FEATURE:
<221> NAME/KEY: MISC_FEATURE
<222> LOCATION: (2)..(4)
<223> OTHER INFORMATION: Xaa at positions 2-4 may be any naturally-
      occurring amino acids and up to three of them may be absent -continued

```
<220> FEATURE:
<221> NAME/KEY: MISC_FEATURE
<222> LOCATION: (11)..(12)
<223> OTHER INFORMATION: Xaa at positions 11-12 may be any naturally-
      occurring amino acids and up to two of them may be absent

<400> SEQUENCE: 63

Gln Xaa Xaa Xaa Leu His Val Tyr His His Xaa Xaa Ile
1               5                   10

<210> SEQ ID NO 64
<211> LENGTH: 12
<212> TYPE: PRT
<213> ORGANISM: Artificial
<220> FEATURE:
<223> OTHER INFORMATION: Parietochloris incisa;Marchantia polymorpha;
      Ostreococcus tauri;Physcomitrella patens
<220> FEATURE:
<221> NAME/KEY: MISC_FEATURE
<222> LOCATION: (3)..(4)
<223> OTHER INFORMATION: Xaa at positions 3-4 may be any naturally-
      occurring amino acids and up to two of them may be absent
<220> FEATURE:
<221> NAME/KEY: MISC_FEATURE
<222> LOCATION: (7)..(7)
<223> OTHER INFORMATION: Xaa at position 7 may be any naturally-
      occurring amino acid and up to one amino acid may be absent
<220> FEATURE:
<221> NAME/KEY: MISC_FEATURE
<222> LOCATION: (10)..(10)
<223> OTHER INFORMATION: Xaa at position 10 may be any naturally-
      occurring amino acid and up to one amino acid may be absent

<400> SEQUENCE: 64

Asn Ser Xaa Xaa His Val Xaa Met Tyr Xaa Tyr Tyr
1               5                   10

<210> SEQ ID NO 65
<211> LENGTH: 8
<212> TYPE: PRT
<213> ORGANISM: Artificial
<220> FEATURE:
<223> OTHER INFORMATION: Parietochloris incisa;Marchantia polymorpha;
      Ostreococcus tauri;Physcomitrella patens
<220> FEATURE:
<221> NAME/KEY: MISC_FEATURE
<222> LOCATION: (2)..(3)
<223> OTHER INFORMATION: Xaa at positions 2-3 may be any naturally-
      occurring amino acids and up to two of them may be absent
<220> FEATURE:
<221> NAME/KEY: MISC_FEATURE
<222> LOCATION: (5)..(6)
<223> OTHER INFORMATION: Xaa at positions 5-6 may be any naturally-
      occurring amino acids and up to two of them may be absent

<400> SEQUENCE: 65

Thr Xaa Xaa Gln Xaa Xaa Gln Phe
1               5
```